US011731946B2

United States Patent
Rahme et al.

(10) Patent No.: US 11,731,946 B2
(45) Date of Patent: Aug. 22, 2023

(54) BROAD SPECTRUM ANTIVIRULENCE, ANTI-PERSISTENCE COMPOUNDS

(71) Applicants: Francois Lepine, Lavaltrie (CA); The General Hospital Corporation, Boston, MA (US); Aptuit (Verona) SRL, An Evotec Company, Verona (IT)

(72) Inventors: Laurence Rahme, Brookline, MA (US); Francois Lepine, Lavaltrie (CA); Damien Maura, Somerville, MA (US); Carmela Napolitano, Verona (IT); Antonio Felici, Vigasio (IT); Michele Negri, Zevio (IT); Stefano Fontana, Pove del Grappa (IT); Daniele Andreotti, San Giovanni Lupatoto (IT)

(73) Assignees: The General Hospital Corporation, Boston, MA (US); Aptuit (Verona) SRL, An Evotec Company, Verona (IT)

( * ) Notice: Subject to any disclaimer, the term of this patent is extended or adjusted under 35 U.S.C. 154(b) by 0 days.

(21) Appl. No.: 16/757,096

(22) PCT Filed: Oct. 19, 2018

(86) PCT No.: PCT/US2018/056771
§ 371 (c)(1),
(2) Date: Apr. 17, 2020

(87) PCT Pub. No.: WO2019/079759
PCT Pub. Date: Apr. 25, 2019

(65) Prior Publication Data
US 2021/0130306 A1    May 6, 2021

Related U.S. Application Data

(60) Provisional application No. 62/663,105, filed on Apr. 26, 2018, provisional application No. 62/574,500, filed on Oct. 19, 2017.

(51) Int. Cl.
*C07D 263/58* (2006.01)
*C07C 237/42* (2006.01)
*C07C 255/60* (2006.01)
*C07C 327/42* (2006.01)
*C07D 209/08* (2006.01)

(52) U.S. Cl.
CPC .......... *C07D 263/58* (2013.01); *C07C 237/42* (2013.01); *C07C 255/60* (2013.01); *C07C 327/42* (2013.01); *C07D 209/08* (2013.01)

(58) Field of Classification Search
None
See application file for complete search history.

(56) References Cited

U.S. PATENT DOCUMENTS

| 5,492,915 | A  | 2/1996  | Dereu et al.   |
|-----------|----|---------|----------------|
| 8,877,940 | B2 | 11/2014 | Rahme et al.   |
| 11,407,760| B2 | 8/2022  | Zhang et al.   |
| 2008/0139534 | A1 | 6/2008 | Huang et al. |
| 2008/0280964 | A1 | 11/2008 | Schuren et al. |
| 2010/0267702 | A1 | 10/2010 | Huang et al. |
| 2020/0399285 | A1 | 12/2020 | Zhang et al. |

FOREIGN PATENT DOCUMENTS

| CN | 108503650      | 9/2018  |
| CN | 108929324      | 12/2018 |
| CN | 110156803      | 8/2019  |
| CN | 111788207      | 10/2020 |
| CN | 113024803      | 6/2021  |
| CN | 114605391      | 6/2022  |
| JP | 2021-512930    | 5/2021  |
| WO | WO 2008/070831 | 6/2008  |
| WO | WO 2018/153293 | 8/2018  |
| WO | WO 2019/154133 | 8/2019  |

OTHER PUBLICATIONS

CAS Registry No. 1898663-01-8, entered Apr. 27, 2016.*
CAS Registry No. 1898676-81-7, entered Apr. 27, 2016.*
CAS Registry No. 1908315-64-9, entered May 11, 2016.*
CAS Registry No. 1898663-01-8, Apr. 27, 2016.*
CAS Registry No. 1907775-60-3, May 11, 2016.*
Acosta et al., "The Evolving Cystic Fibrosis Microbiome: A Comparative Cohort Study Spanning 16 Years," Annals of the American Thoracic Society, Aug. 2017, 14(8):1288-1297.
Amato et al., "The role of metabolism in bacterial persistence," Frontiers in Microbiology, Mar. 2014, 5(70).
Anderson et al., "In vitro analysis of tobramycin-treated Pseudomonas aeruginosa biofilms on cystic fibrosis-derived airway epithelial cells," Infect. Immun., Apr. 2008, 76(4):1423-1433.
Barie, "Multidrug-resistant organisms and antibiotic management," P.S., Surg. Clin. North Am., Apr. 2012, 92(2):345-391.
Bigger, "Treatment of *Staphylococcal* Infections with Penicillin by Intermittent Sterilisation," Lancet, Oct. 1944, 244(6320):497-500.
Bjarnsholt et al., "Why chronic wounds will not heal: a novel hypothesis," Wound Repair Regen. Jan. 2008, 16(1):2-10.
Boucher et al., "Bad bugs, no drugs: no ESKAPE! An update from the Infectious Diseases Society of America," Clin. Infect. Dis. Jan. 2009, 48(1):1-12.
Chassaing et al., "The commensal microbiota and enteropathogens in the pathogenesis of inflammatory bowel diseases," Gastroenterology, 2011, 140(6):1720-1728.

(Continued)

*Primary Examiner* — Joseph R Kosack
(74) *Attorney, Agent, or Firm* — Fish & Richardson P.C.

(57) ABSTRACT

The present application provides malonamide compounds, and derivatives thereof (e.g., N-aryl malonamides (NAM), acetamides, oxalamides, and the like), that are useful, for example, for the treatment of acute, chronic/persistent, and/or relapsing infections. Pharmaceutical compositions, methods of treating diseases (e.g., bacterial infections), and methods of reducing bacterial virulence are also provided.

14 Claims, 32 Drawing Sheets

(56) References Cited

OTHER PUBLICATIONS

Costerton & Stewart., "Bacterial biofilms: a common cause of persistent infections," Science, May 1999, 284(5418):1318-1322.
Deziel et al., "The contribution of MvfR to Pseudomonas aeruginosa pathogenesis and quorum sensing circuitry regulation: multiple quorum sensing-regulated genes are modulated without affecting lasRI, rhlRI or tire production of N-acyl-L-homoserine lactones," Mol. Microbiol., Feb. 2005, 55(4):998-1014.
Diacon et al., "The diarylquinoline TMC207 for multidrug-resistant tuberculosis," N. Engl. J. Med., Jun. 2009, 360(23):2397-2405.
Fauvart et al.. "Role of persister cells in chronic infections: clinical relevance and perspectives on anti-persister therapies," Journal of Medical Microbiology, Jun. 2011, 60(6):699-709.
Frangolias et al., "*Burkholderia cepacia* in cystic fibrosis: variable disease course," Am J. Respir. Crit. Care Med., Nov. 1999, 160(5):1572-1577.
Fux et al., "Survival strategies of infectious biofilms," Trends Microbiol., Jan. 2005, 13(1):34-40.
Gandhi & Gandhi., "Single-pill combination regimens for treatment of HIV-1 infection," N. Engl. J. Med., Jul. 2014, 371(3):248-259.
Ganesan & Sajjan, "Host evasion by Burkholderia cenocepacia," Front Cell Infect. Microbiol., Jan. 2012, 1:25, 9 pages.
Gasink & Brennan, "Isolation precautions for antibiotic-resistant bacteria in healthcare settings," Curr. Opin. Infect. Dis., Aug. 2009, 22(4):339-344.
Gellatly & Hancock, "*Pseudomonas aeruginosa*: new insights into pathogenesis and host defenses," Pathog. Dis., Apr. 2013, 67(3):159-173.
Hampton et al.. "Does the ΔF508-CFTR mutation induce a proinflammatory response in human airway epithelial cells?," Am. J. Physiol. Lung Cell Mol. Physiol., Sep. 2012, 303(6):509-518.
Harun et al., "A systematic review of studies examining the rate of lung function decline in patients with cystic fibrosis," Paediatric Respiratory Reviews, Sep. 2016, 100(20):55-66.
Hazan et al., "Auto poisoning of the respiratory chain by a quorum-sensing-regulated molecule favors biofilm formation and antibiotic tolerance," Current Biology, Jan. 2016, 26(2):195-206.
Hilf et al., "Antibiotic therapy for *Pseudomonas aeruginosa* bacteremia: outcome correlations in a prospective study of 200 patients," Am. J. Med., Nov. 1989, 87(5):540-546.
Hogardt & Heesemann, "Adaptation of *Pseudomonas aeruginosa* during persistence in the cystic fibrosis lung," Int. J. Med. Microbiol., Dec. 2010, 300(8):557-562.
Kefala et al., "Purification, crystallization and preliminary X-ray diffraction analysis of the C-terminal fragment of the MvfR protein from *Pseudomonas aeruginosa*" Acta. Crvstallogr. Sect. F. Struct. Biol. Cryst. Commun., Jun. 2012, 68(6):695-697.
Keren et al., "Persister cells and tolerance to antimicrobials." FEMS Microbiol. Lett., Jan. 2004, 230(1):13-18.
Kerr & Snelling, "*Pseudomonas aeruginosa*: a formidable and ever-present adversary," J. Hosp. Infect. Dec. 2009, 73(4):338-344.
Kerstjens et al., "Tiotropium in asthma poorly controlled with standard combination therapy." New Engl. J. Med., Sep. 2012, 367(13):1198-1207.
Kesarwani et al., "A quorum sensing regulated small volatile molecule reduces acute virulence and promotes chronic infection phenotypes," Plos Pathogens. Aug. 2011, 7(8):e1002192.
Kopacova et al., "Small Intestinal Bacterial Overgrowth Syndrome" World J. Gastroenterol., Jun. 2010, 16(24):2978-2990.
Kukavica-Ibrulj et al., "Assessing Pseudomonas aeruginosa virulence and the host response using murine models of acute and chronic lung infection," Methods Mol. Biol., Jan. 2014, 1149:757-771.
Lebeaux et al., "Biofilm-related infections: bridging the gap between clinical management and fundamental aspects of recalcitrance toward antibiotics," Microbiol. Mol. Biol. Rev., Sep. 2014, 78(3):510-543.
Lewis & Torres, "The art of persistence-the secrets to *Burkholderia* chronic infections," Pathog. Dis., 2016, 74(6), 11 pages.
Lewis, "Persister cells, dormancy and infectious disease," Nat. rev. Microbiol., Jan. 2007, 5(1):48-56.
Lewis. "Persister cells," Annual Review of Microbiology, Jun. 2010, 64:357-375.
Lister et al., "Antibacterial-resistant *Pseudomonas aeruginosa*: clinical impact and complex regulation of chromosomally encoded resistance mechanisms," Clin. Microbiol. Rev., Oct. 2009, 22(4):582-610.
Livermore, "Current epidemiology and growing resistance of gram-negative pathogens." Korean J. Intern. Med., Jun. 2012, 27(2):128-142.
Lund-Palau et al., "*Pseudomonas aeruginosa* infection in cystic fibrosis: pathophysiological mechanisms and therapeutic approaches," Expert Rev. Respir. Med., May 2016, 10(6):685-697.
Maura et al., "Evidence for direct control of virulence and defense gene circuits by the *Pseudomonas aeruginosa* quorum sensing regulator, MvfR," Sci. Rep., Sep. 2016, 6(1):34083, 14 pages.
Maura et al., "Polypharmacology Approaches against the *Pseudomonas aeruginosa* MvfR Regulon and Their Application in Blocking Virulence and Antibiotic Tolerance," ACS Chemical Biology, Apr. 2017, 12(5):1435-1443.
McManus et al., "Antibiotic Use in Plant Agriculture" Annu. Rev. Phytopathol., Sep. 2002, 40(1):443-465.
Mulcahy et al., "*Pseudomonas aeruginosa* biofilms in disease," Microb. Ecol., Jul. 2014, 68(1):1-12.
O'Malley, "Infection control in cystic fibrosis: cohorting, cross-contamination, and the respiratory therapist," C.A. Respir, Care, May 2009, 54(5):641-657.
PCT International Preliminary Report on Patentability in International Appln. No. PCT/US2018/056771, dated Apr. 21, 2020, 10 pages.
PCT International Search Report and Written Opinion in International Appln. No. PCT/US2018/056771, dated Feb. 11, 2019, 21 pages.
Poole, "Multidrug efflux pumps and antimicrobial resistance in *Pseudomonas aeruginosa* and related organisms," Journal of Molecular Microbiology and Biotechnology, Apr. 2001, 3(2):255-264.
Pubchem Substance Record for SID 319129655, "c3-12-00-02073 (Beilstein Handbook Reference)" Nov. 29, 2016, 6 pages.
Pulli et ah, "Measuring myeloperoxidase activity in biological samples," PLOS One, Jul. 2013, 8(7):e67976, 11 pages.
Que et al., "A quorum sensing small volatile molecule promotes antibiotic tolerance in bacteria." PLoS One, Dec. 2013, 8(12):e80140, 9 pages.
Rabin et al., "Agents that inhibit bacterial biofilm formation," Future Med. Chem., Apr. 2015, 7(5):647-671.
Robert et al., "Improved overall survival in melanoma with combined dabrafenib and trametinib," N. Eng. J. Med., Jan. 2015, 372(1):30-39.
Samanta et al.. "Hypoxia-inducible factors are required for chemotherapy resistance of breast cancer stem cells," Proc. Natl. Acad. Sci. U.S.A., Dec. 2014, 111(5):E5429-E5438.
Sever & Messerli., "Hypertension management 2011: optimal combination therapy," Eur. Heart J., Oct. 2011, 32(2):2499-2506.
Starkey et al., "Identification of anti-virulence compounds that disrupt quorum-sensing regulated acute and persistent pathogenicity," PLoS Pathog., Aug. 2014, 10(8):e1004321.
Tolaney et al., "Adjuvant paclitaxel and trastuzumab for node-negative, HER2-positive breast cancer," N. Eng. J. Med., Jan. 2015, 372(2):134-141.
Vilar et al., "Medical combination therapies in Cushing's disease," Pituitary, Apr. 2015, 18(2):253-262.
Vogt et al., "The stringent response is essential for *Pseudomonas aeruginosa* virulence in the rat lung agar bead and *Drosophila melanogaster* feeding models of infection," Infect. Immun., Oct. 2011, 79(10):4094-4104.
Walker & Mason, "A standard animal burn," J. Trauma, Nov. 1968, 8(6):1049-1051.
Wood et al., "Bacterial persister cell formation and dormancy," Applied and Environmental Microbiology, Dec. 2013, 79(23):7116-7121.
Worthington & Melander, "Combination approaches to combat multidrug-resistant bacteria," Trends Biotechnol., Mar. 2013, 31(3):177-184.

(56) References Cited

OTHER PUBLICATIONS

Xiao et al., "Mutation analysis of the *Pseudomonas aeruginosa* mvfR and pqsABCDE gene promoters demonstrates complex quorum-sensing circuitry," Microbiology, Jun. 2006, 152(6):1679-1686.

Arsovski et al., "Abstract: Computational and spectroscopic data correlation study of N,N'-bisarylmalonamides (Part II)," Journal of Molecular Modeling, 2015, 21(9):1-11, 1 page.

Arsovski et al., "Abstract: Spectroscopic and quantum mechanical investigation of N,N'-bisarylmalonamides: solvent and structural effects," Journal of Molecular Modeling, 2014, 20(8):2384, 1 page.

Jiang et al., "Abstract: Discovery and SAR study of c-Met kinase inhibitors bearing an 3-aminobenzo [d]isoxazole or 3-aminoindazole scaffold," Bioorganic & Medicinal Chemistry, 2015, 23(3):564-578, 1 page.

Li et al., "Abstract: Discovery of a highly potent, selective and novel CDK9 inhibitor as an anticancer drug candidate," Bioorg Med Chem Lett, Aug. 2017, 27(15):3231-3237, 1 page.

STN Registry, "42 compounds disclosed in miscellaneous chemical catalogs," Aug. 2004-May 2019, retrieved on Nov. 10, 2022, 21 pages.

STN Registry, "Compounds disclosed in publications," retrieved on Nov. 10, 2022, 16 pages.

Chemical compounds entered to CAS Registry on STN between Jun. 2009 and May 2019.

\* cited by examiner

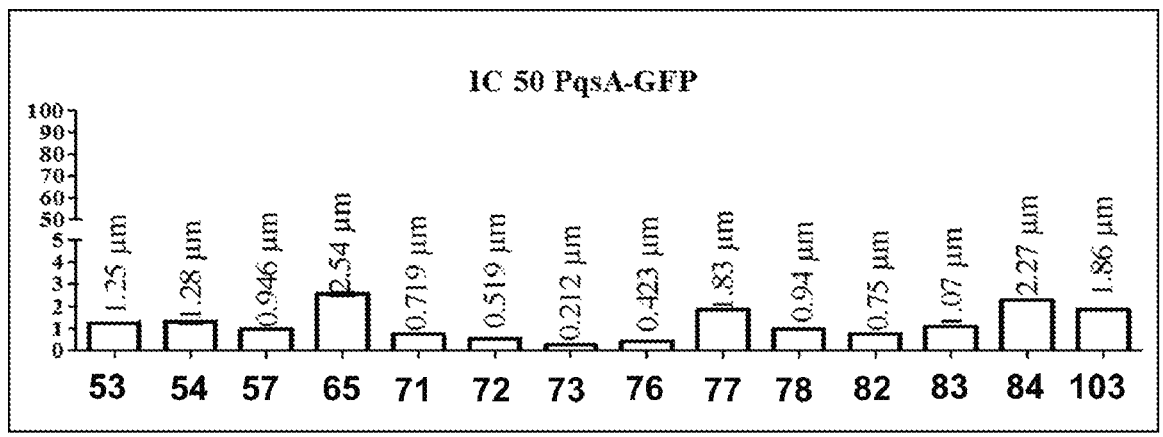
Figure 4B
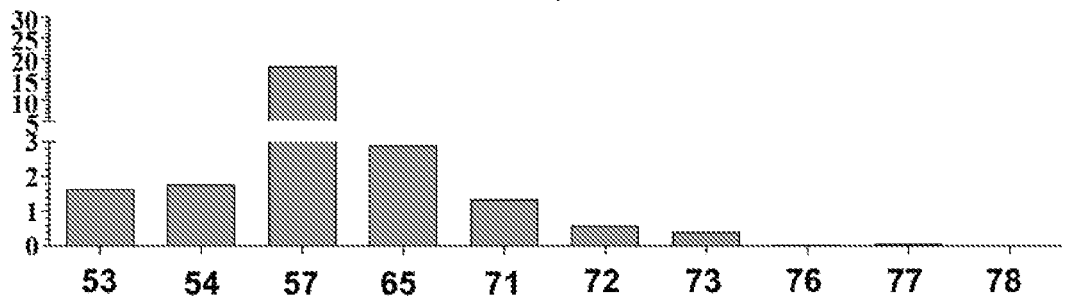
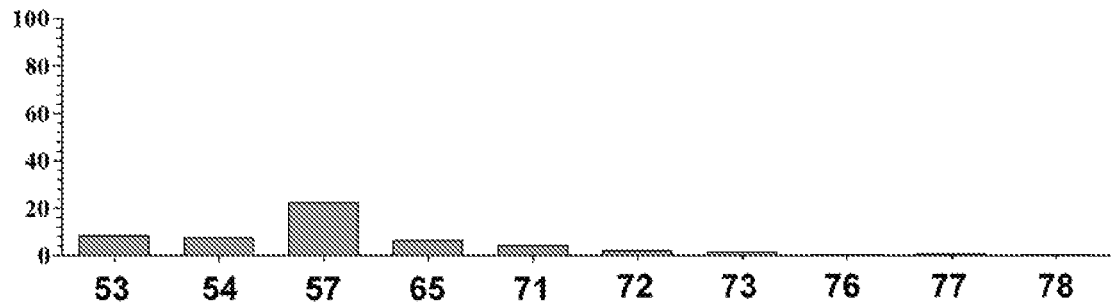
Figures 4C-4D

BROAD SPECTRUM ANTIVIRULENCE, ANTI-PERSISTENCE COMPOUNDS

CROSS-REFERENCE TO RELATED APPLICATIONS

This application is a § 371 National Stage Application of PCT/US2018/056771, filed Oct. 19, 2018, which claims the benefit of U.S. Provisional Application Ser. No. 62/574,500, filed Oct. 19, 2017; and 62/663,105, filed Apr. 26, 2018. The disclosure of each application is incorporated herein by reference in its entirety.

FEDERALLY SPONSORED RESEARCH OR DEVELOPMENT

This invention was made with Government support under Grant No. AI105902, awarded by the National Institutes of Health. The Government has certain rights in the invention.

TECHNICAL FIELD

The present disclosure provides malonamide compounds and derivatives thereof (e.g., N-aryl malonamides (NAM), acetamides, oxalamides, and the like), that are useful, for example, in the treatment of acute, chronic, and/or relapsing infections.

BACKGROUND

Antibiotic resistant and tolerant microbes are responsible for a substantial portion of acute and persistent infections that are prevalent worldwide. Acute and persistent infections are frequently associated with elevated inflammation and a strong immune response, which may lead to progressive damage and ultimately result in airway function decline and potentially death. Attempts to eradicate infections fail when conventional antibiotics leave the subpopulation of bacterial cells that are refractory to antibiotics unharmed. These Antibiotic Tolerant, Persister (AT/P) cells are ultimately responsible for persistent, chronic or relapsing infections (see e.g., Bigger, J., *Lancet*, 1944, 244:497-500; Bjarnsholt et al, *Wound Repair Regen.* 2008, 16:2-10; Boucher et al, *Clin. Infect. Dis.* 2009, 48:1-12; Gasink & Brennan, *Curr. Opin. Infect. Dis.* 2009, 22:339-344; Lewis, K., *Annual Review of Microbiology*, 2010; Fauvart et al, *Journal of Medical Microbiology*, 2011, 60:699-709; and Barie, P. S., *Surg. Clin. North Am.* 2012, 92:345-391, ix-x). Bacterial persistence is observed in a broad range of microbial species. *Pseudomonas aeruginosa* (PA), a major nosocomial pathogen, represents a critical threat for human health (see e.g., Gellatly & Hancock, *Pathog. Dis.* 2013, 67:159-173; Kerr & Snelling, *J. Hosp. Infect.* 2009, 73:338-344) because of its high tolerance to antibiotics and rapid development of resistance towards almost all current antimicrobial therapies (see e.g., Lewis, *Nat. rev. Microbiol.* 2007, 5:48-56; Mulcahy et al, *Microb. Ecol.* 2014, 68:1-12; Costerton & Stewart, *Science*, 1999, 284:1318-1322; Lebeaux et al, *Microbiol. Mol. Biol. Rev.* 2014, 78:510-543; Lister et al, *Clin. Microbiol. Rev.* 2009, 22:582-610; Que et al, *PLoS One*, 2013, 8:e80140; Livermore, *Korean J. Intern. Med.* 2012, 27:128-142; and Rabin et al *Future Med. Chem.* 2015, 7:647-671). Both PA and *Burkholderia cepacia* complex (Bcc) are of particular concern in cystic fibrosis (CF) infections due to natural antibiotic resistance and quorum sensing (QS)-induced survival strategies. QS, a small-molecule orchestrated signaling system used to sense bacterial presence, coordinates many group behaviors such as virulence, motility, biofilm formation, and the development of dormant cells that survive antibiotic killing, known as persisters. Both PA and Bcc excrete QS-regulated small molecules that serve as persistence "infochemicals" (see e.g., Kesarwani et al, *Plos Pathogens*, 2011, 7; and Hazan et al, *Current Biology*, 2016, 26:195-206).

SUMMARY

The present application provides, inter alia, a compound of Formula I:

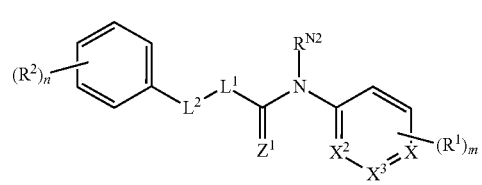

or a pharmaceutically acceptable salt thereof, wherein:
$Z^1$ is selected from the group consisting of O and S;
$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;
$L^2$ is selected from the group consisting of C(O), C(S), $(C_{1-4}$ alkylene)-C(O), $NR^{N1}C(O)$, $NR^{N1}C(S)$, and $NR^{N1}SO_2$;
or, alternatively, $L^2$ is absent;
$R^{N1}$ and $R^{N2}$ are each independently selected from the group consisting of H and $C_{1-4}$ alkyl;
$X^2$, $X^3$, and $X^4$ are each independently selected from the group consisting of C and N;
each $R^1$ is independently selected from the group consisting of H, $C_{1-4}$ alkyl, $C_{1-4}$ haloalkyl, halo, CN, $NO_2$, $NH_2$, —COOH, —CONH$_2$, and OH;
or, alternatively, $R^{N2}$ and $R^1$, together with the atoms to which they are attached, come together to form a 5-6 membered heterocycloalkyl group;
or, alternatively, $R^{N2}$ and $L^1$ or $X^2$ come together to form a 5-6 membered heterocycloalkyl group;
each $R^2$ is independently selected from the group consisting of $C_{1-4}$ alkyl, halo, CN, $NH_2$, —COOH, —CONH$_2$, —C(O)$C_{1-4}$ haloalkyl, —NHC(O)$C_{1-4}$ haloalkyl, —NHSO$_2$—$C_{1-4}$ alkyl, and phenoxy;
m is 1, 2, or 3; and
n is 1, 2, or 3;
with the proviso that if L is cyclopropylene then at least one $R^1$ group is CN;
wherein the compound of Formula I is not a compound selected from the group consisting of:

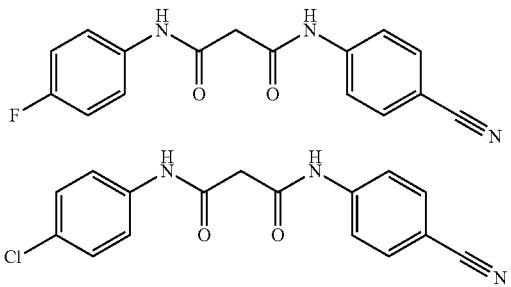

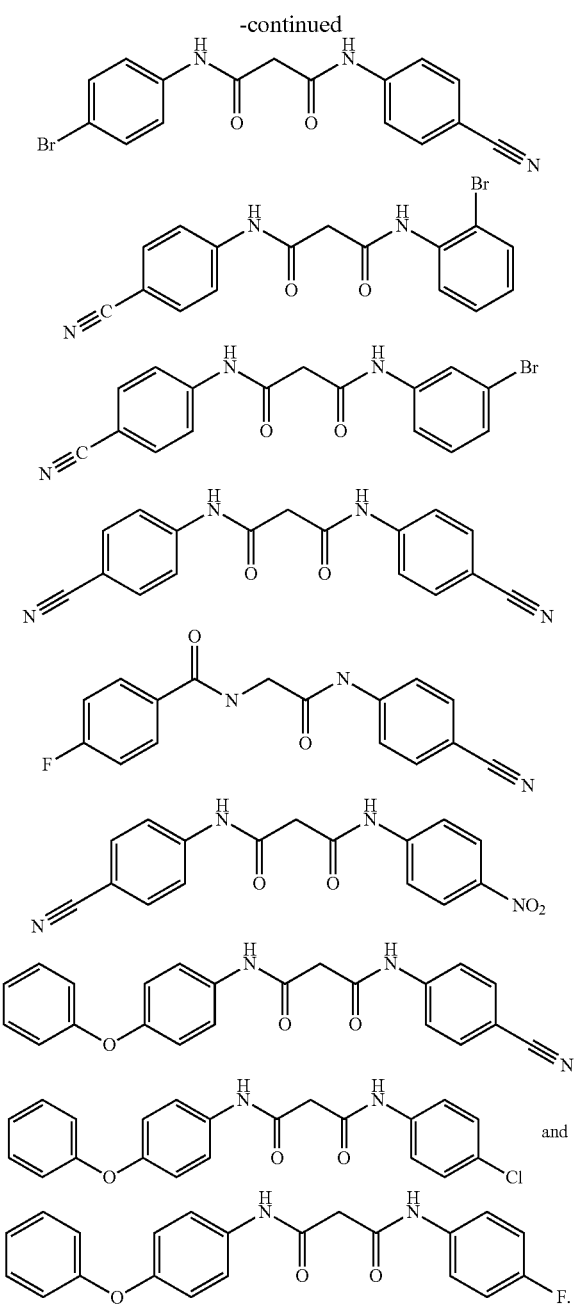

In some embodiments, $Z^1$ is O. In some embodiments, $Z^1$ is S.

In some embodiments, $L^1$ is methylene.

In some embodiments, $L^2$ is absent. In some embodiments, $L^2$ is selected from the group consisting of C(O), C(S), ($C_{1-4}$ alkylene)-C(O), $NR^{N1}C(O)$, $NR^{N1}C(S)$, and $NR^{N1}SO_2$. In some embodiments, $L^2$ is selected from the group consisting of C(O), $NR^{N1}C(O)$, $NR^{N1}C(S)$, and $NR^{N1}SO_2$.

In some embodiments, $R^{N1}$ is selected from the group consisting of H and methyl. In some embodiments, $R^{N2}$ is selected from the group consisting of H and methyl.

In some embodiments, $L^2$ is NHC(O).

In some embodiments, $R^{N2}$ and $L^1$, together with the atoms to which they are attached, come together to form a 5-6 membered heterocycloalkyl group. In some embodiments, $R^{N2}$ and $L^1$, together with the atoms to which they are attached, come together to form a pyrrolidinone group.

In some embodiments, $X^2$ is C. In some embodiments, $X^2$ is N.

In some embodiments, $X^3$ is C. In some embodiments, $X^3$ is N.

In some embodiments, $X^4$ is C. In some embodiments, $X^4$ is N.

In some embodiments, each $R^1$ is independently selected from the group consisting of H, methyl, trifluoromethyl, halo, CN, $NO_2$, $NH_2$, and OH.

In some embodiments, each $R^2$ is independently selected from the group consisting of methyl, fluoro, iodo, CN, $NH_2$, —C(O)$CF_3$, —NHC(O)$CF_3$, —NHSO$_2$CH$_2$CH$_3$, and phenoxy.

In some embodiments, m is 1 or 2.

In some embodiments, n is 1 or 2.

In Some Embodiments:

$Z^1$ is selected from the group consisting of O and S;

$L^1$ is selected from the group consisting of methylene, ethylene, ethen-1,2-diyl, fluoromethylene, cyclopropylene, and hydroxypropylene;

$L^2$ is selected from the group consisting of C(O), $NR^{N1}C(O)$, $NR^{N1}C(S)$, and $NR^{N1}SO_2$;

or, alternatively, $L^2$ is absent;

$R^{N1}$ is selected from the group consisting of H and methyl;

$R^{N2}$ is selected from the group consisting of H and methyl;

$X^2$, $X^3$, and $X^4$ are each independently selected from the group consisting of C and N;

each $R^1$ is independently selected from the group consisting of H, methyl, trifluoromethyl, halo, CN, $NO_2$, $NH_2$, and OH;

each $R^2$ is independently selected from the group consisting of methyl, fluoro, iodo, CN, $NH_2$, —C(O)$CF_3$, —NHC(O)$CF_3$, —NHSO$_2$CH$_2$CH$_3$, and phenoxy;

m is 1 or 2; and n is 1 or 2.

In Some Embodiments:

$Z^1$ is O;

$L^1$ is selected from the group consisting of methylene, ethylene, ethen-1,2-diyl, fluoromethylene, cyclopropylene, and hydroxypropylene;

$L^2$ is $NR^{N1}C(O)$;

or, alternatively, $L^2$ is absent;

$R^{N1}$ is selected from the group consisting of H and methyl;

$R^{N2}$ is selected from the group consisting of H and methyl;

$X^2$, $X^3$, and $X^4$ are each independently selected from the group consisting of C and N;

each $R^1$ is independently selected from the group consisting of H, methyl, trifluoromethyl, halo, CN, $NO_2$, $NH_2$, and OH;

each $R^2$ is independently selected from the group consisting of methyl, fluoro, iodo, CN, $NH_2$, —C(O)$CF_3$, —NHC(O)$CF_3$, —NHSO$_2$CH$_2$CH$_3$, and phenoxy;

m is 1 or 2; and n is 1 or 2.

In some embodiments the compound of Formula I is a compound of Formula I-a, I-b, I-c, I-d, I-e, I-f, or I-g:

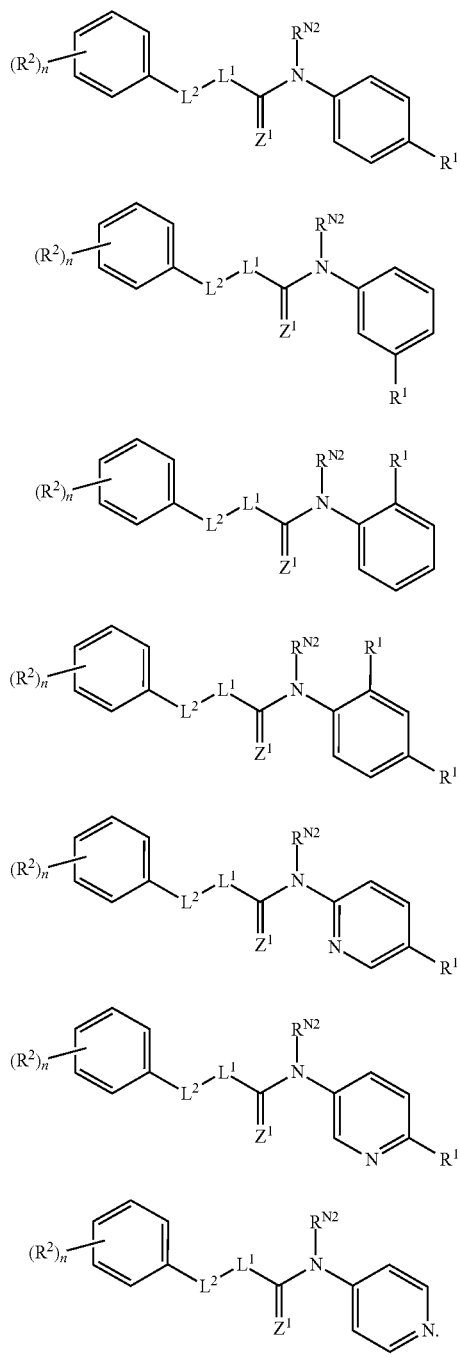
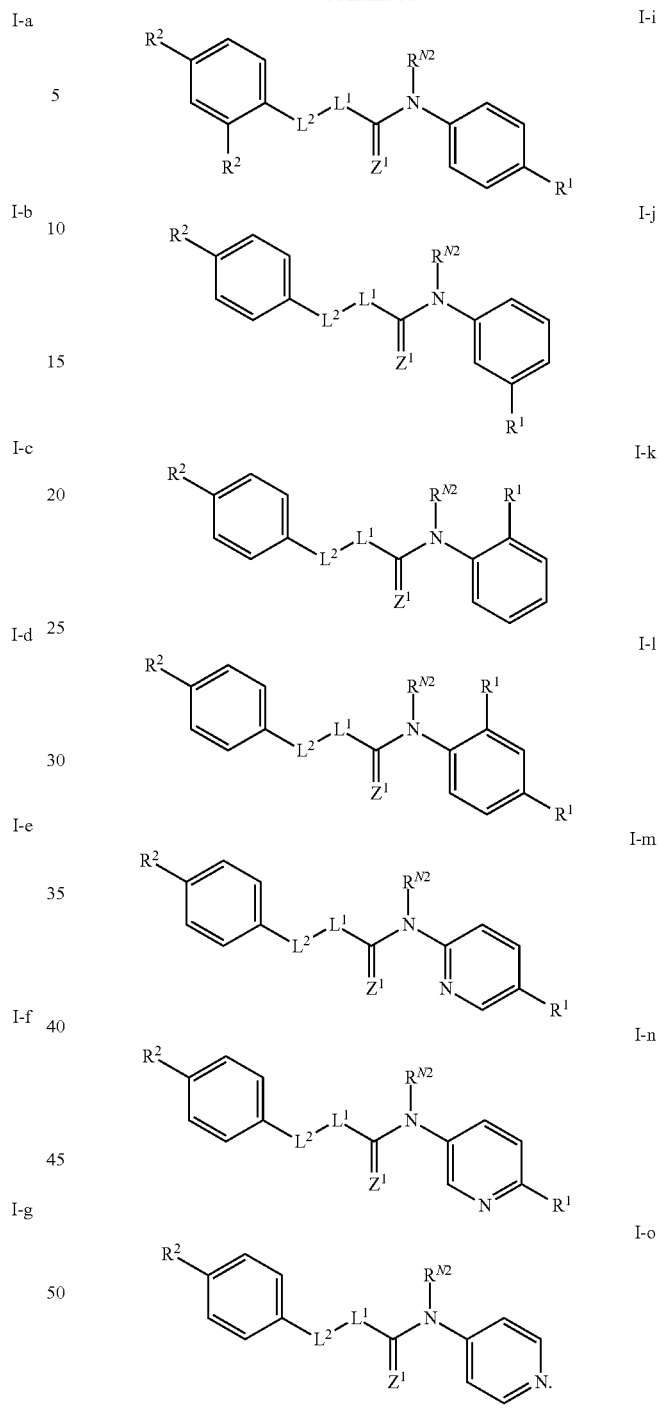
In some embodiments, the compound of Formula I is a compound of Formula I-h, I-i, I-j, I-k, I-l, I-m, I-n, or I-o:
In some embodiments, the compound of Formula I is selected from the group consisting of:
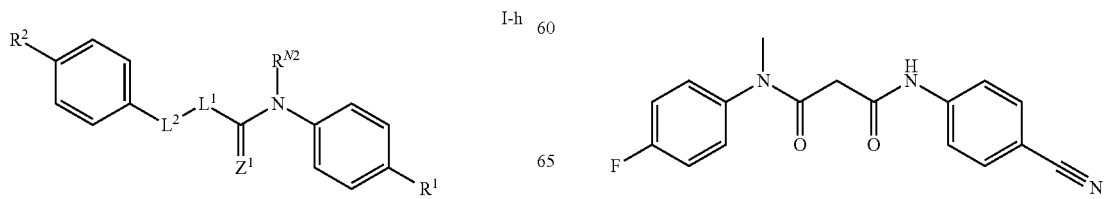

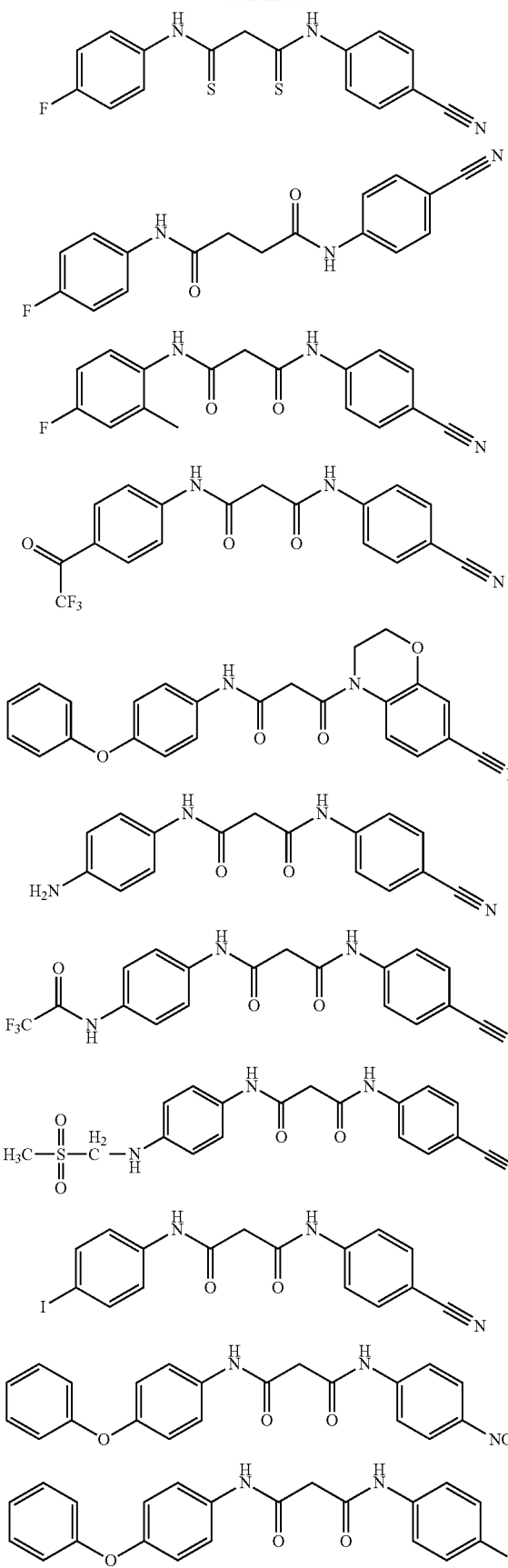
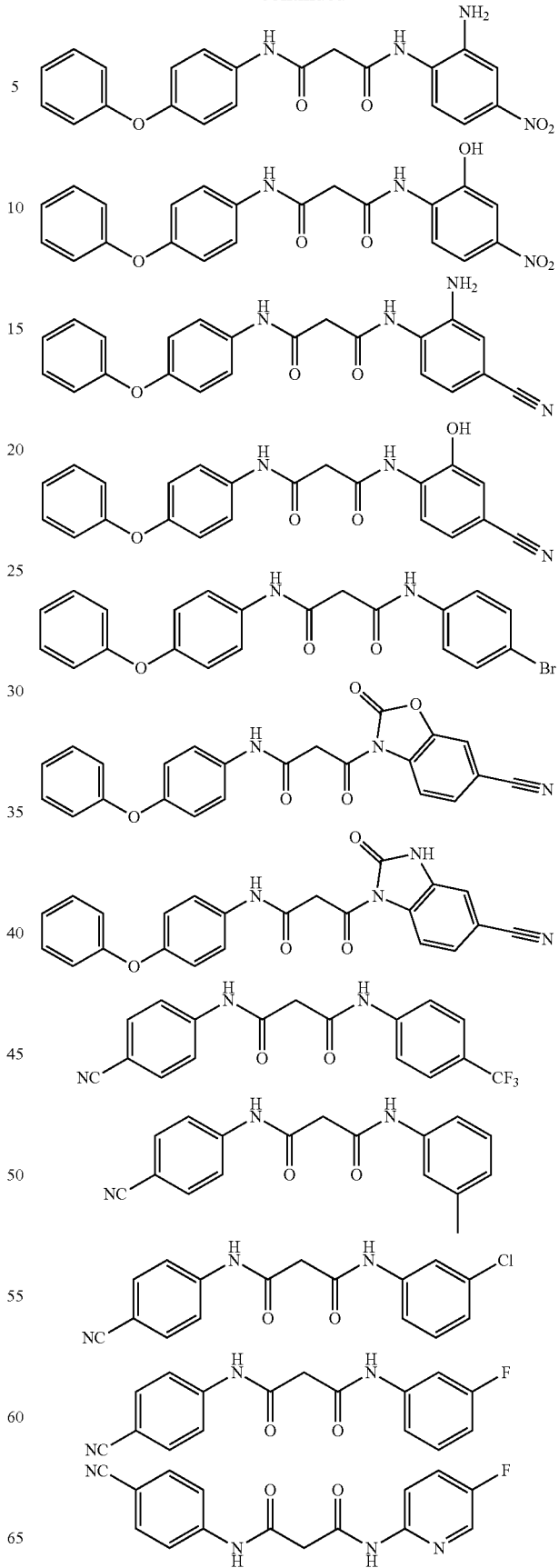

-continued

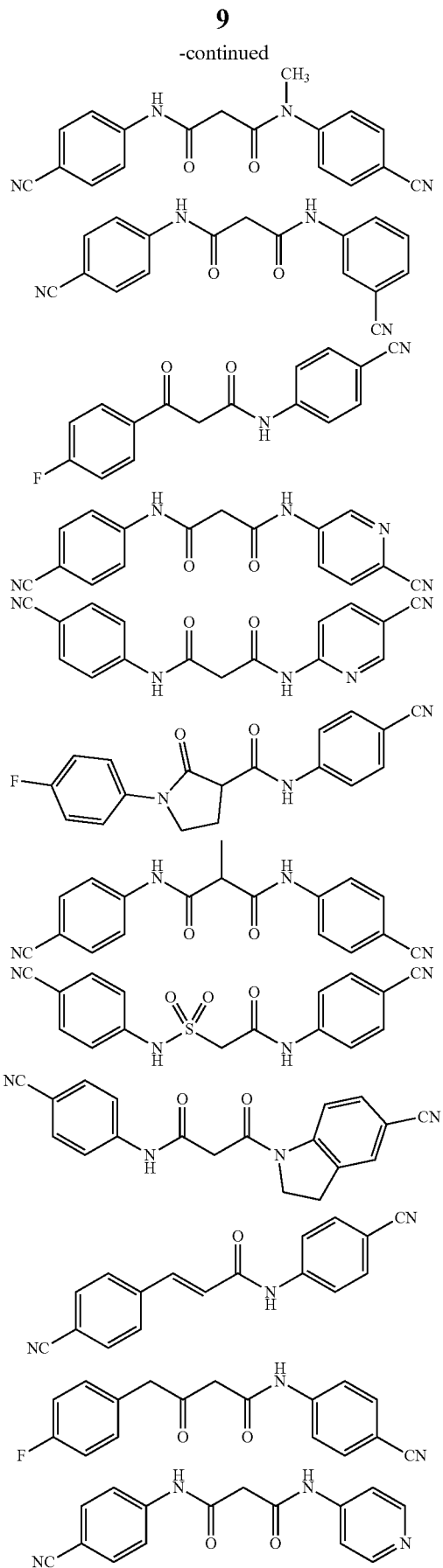

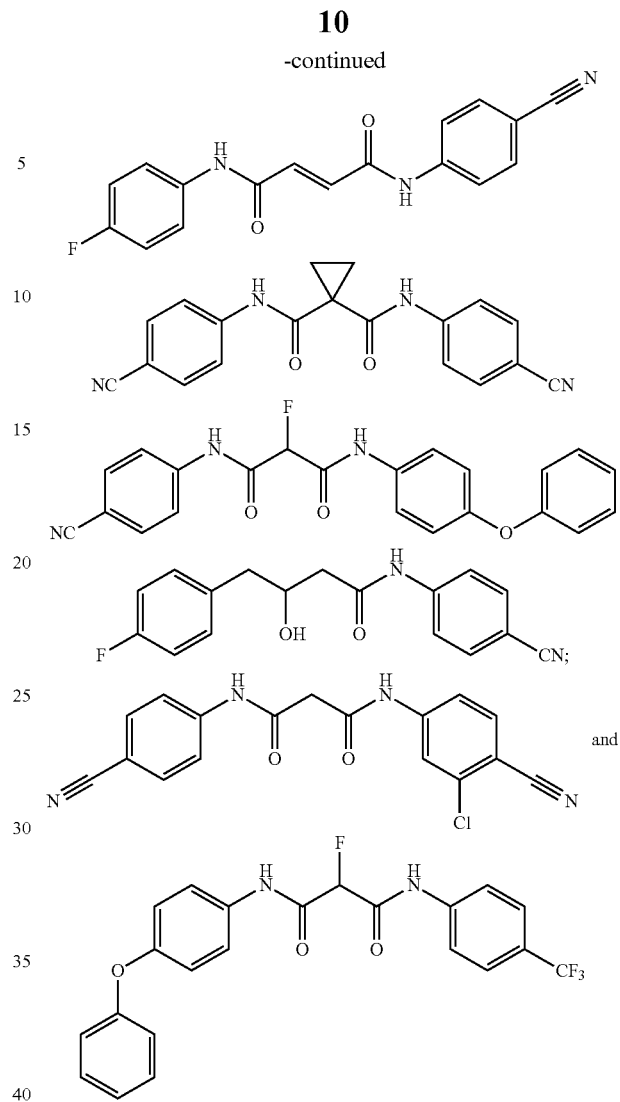

or a pharmaceutically acceptable salt thereof.

The present application further provides a pharmaceutical composition, comprising a compound provided herein (e.g., a compound of Formula I or Formula II), or a pharmaceutically acceptable salt thereof, and a pharmaceutically acceptable carrier.

The present application further provides a method of treating an antibiotic-tolerant infection in a subject in need thereof, the method comprising administering to the subject a therapeutically effective amount of a compound of Formula II:

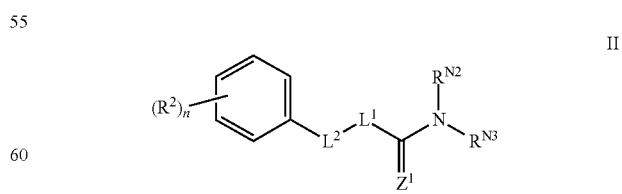

or a pharmaceutically acceptable salt thereof, wherein:

$Z^1$ is selected from the group consisting of O and S;

$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of O, $NR^{N1}$, C(O), C(S), ($C_4$ alkylene)-C(O), $NR^{N1}$C(O), $NR^{N1}$C(S), and $NR^{N1}SO_2$;

or, alternatively, $L^2$ is absent;

$R^{N1}$ and $R^{N2}$ are each independently selected from the group consisting of H and $C_{1-4}$ alkyl;

$R^{N3}$ is selected from the group consisting of $C_{1-4}$ haloalkyl, NH($C_{1-4}$ alkyl), cyclopropyl, phenyl, and pyridyl, wherein the phenyl and pyridyl are optionally substituted by 1, 2, or 3 $R^1$ groups;

each $R^1$ is independently selected from the group consisting of H, $C_{1-4}$ alkyl, $C_{1-4}$ haloalkyl, $C_{1-4}$ alkoxy, halo, CN, $NO_2$, $NH_2$, OH, C(O)$C_{1-4}$ alkyl, C(O)N($C_{1-4}$ alkyl)$_2$, and 5-6 membered heterocycloalkyl;

or, alternatively, $R^{N2}$ and $R^1$, together with the atoms to which they are attached, come together to form a 5-6 membered heterocycloalkyl group;

or, alternatively, $R^{N2}$ and $L^1$ come together to form a 5-6 membered heterocycloalkyl group; and each $R^2$ is independently selected from the group consisting of $C_{1-4}$ alkyl, halo, CN, $NH_2$, —C(O)$C_{1-4}$ haloalkyl, —NHC(O)$C_{1-4}$ haloalkyl, —NHSO$_2$—$C_{1-4}$ alkyl, and phenoxy;

with the proviso that if L is cyclopropylene then at least one $R^1$ group is CN;

wherein the compound of Formula II is not a compound selected from the group consisting of:

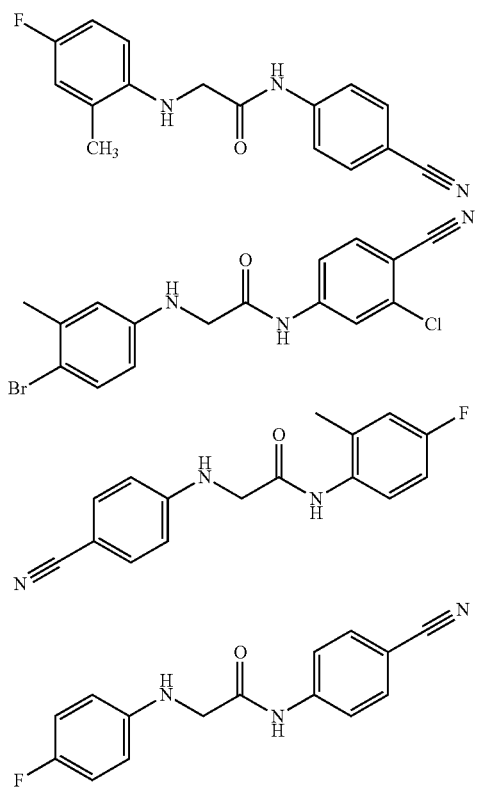

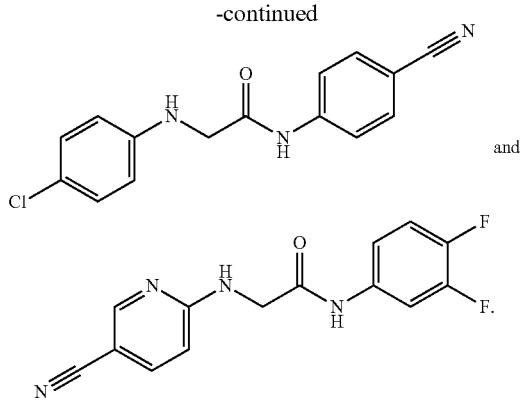

The present application further provides a method of treating a bacterial infection in a subject in need thereof, comprising administering to the subject a therapeutically effective amount of a compound of Formula II:

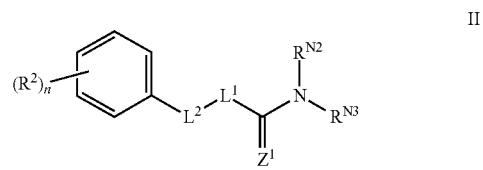

or a pharmaceutically acceptable salt thereof, wherein:

$Z^1$ is selected from the group consisting of O and S;

$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of O, $NR^{N1}$, C(O), C(S), ($C_{1-4}$ alkylene)-C(O), $NR^{N1}$C(O), $NR^{N1}$C(S), and $NR^{N1}SO_2$;

or, alternatively, $L^2$ is absent;

$R^{N1}$ and $R^{N2}$ are each independently selected from the group consisting of H and $C_{1-4}$ alkyl;

$R^{N3}$ is selected from the group consisting of $C_{1-4}$ haloalkyl, NH($C_{1-4}$ alkyl), cyclopropyl, phenyl, and pyridyl, wherein the phenyl and pyridyl are optionally substituted by 1, 2, or 3 $R^1$ groups;

each $R^1$ is independently selected from the group consisting of H, $C_{1-4}$ alkyl, $C_{1-4}$ haloalkyl, $C_{1-4}$ alkoxy, halo, CN, $NO_2$, $NH_2$, OH, C(O)$C_{1-4}$ alkyl, C(O)N($C_{1-4}$ alkyl)$_2$, and 5-6 membered heterocycloalkyl;

or, alternatively, $R^{N2}$ and $R^1$, together with the atoms to which they are attached, come together to form a 5-6 membered heterocycloalkyl group;

or, alternatively, $R^{N2}$ and $L^1$ come together to form a 5-6 membered heterocycloalkyl group; and each $R^2$ is independently selected from the group consisting of $C_{1-4}$ alkyl, halo, CN, $NH_2$, —C(O)$C_{1-4}$ haloalkyl, —NHC(O)$C_{1-4}$ haloalkyl, —NHSO$_2$—$C_{1-4}$ alkyl, and phenoxy;

with the proviso that if L is cyclopropylene then at least one R group is CN;

wherein the compound of Formula II is not a compound selected from the group consisting of:

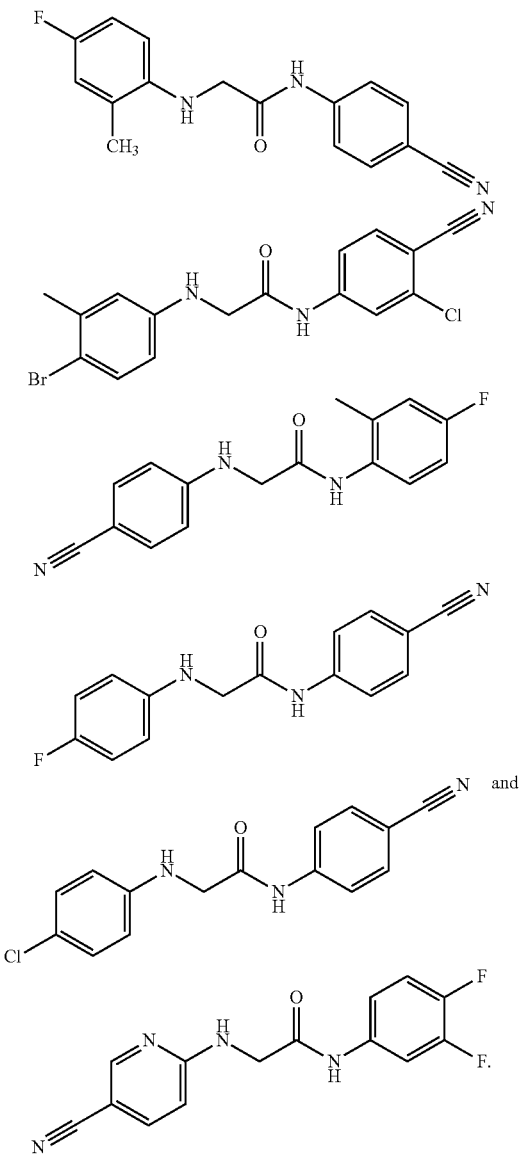

In some embodiments, the bacterial infection or antibiotic-tolerant infection is caused by a gram negative bacterium. In some embodiments, the gram negative bacterium is selected from the group consisting of *Pseudomonas aeruginosa*, *E. coli*, *Acinetobacter*, and *Burkholderia* species. In some embodiments, the bacterial infection or antibiotic-tolerant infection is caused by a gram positive bacterium. In some embodiments, the infection is an acute infection, a chronic infection, or a relapsing infection.

In some embodiments, the acute infection, chronic infection, or relapsing infection is selected from the group consisting of a lung infection, pneumonia, septic shock, urinary tract infection, a gastrointestinal infection, an infection of the skin and soft tissue, an infection that modulates gut permeability, and an infection that modulates brain function, or any combination thereof.

In some embodiments, the subject is a human.

The present application further provides a method of treating a gram negative infection or a gram positive infection in a subject in need thereof, the method comprising administering to the subject a therapeutically effective amount of a compound of Formula II:

$$\text{(R}^2\text{)}_n\text{—Ar—L}^2\text{—L}^1\text{—C(Z}^1\text{)—N(R}^{N2})(R^{N3}) \quad \text{II}$$

or a pharmaceutically acceptable salt thereof, wherein:
$Z^1$ is selected from the group consisting of O and S;
$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;
$L^2$ is selected from the group consisting of O, $NR^{N1}$, C(O), C(S), ($C_{1-4}$ alkylene)-C(O), $NR^{N1}C(O)$, $NR^{N1}C(S)$, and $NR^{N1}SO_2$;
or, alternatively, $L^2$ is absent;
$R^{N1}$ and $R^{N2}$ are each independently selected from the group consisting of H and $C_{1-4}$ alkyl;
$R^{N3}$ is selected from the group consisting of $C_{1-4}$ haloalkyl, $NH(C_{1-4}$ alkyl), cyclopropyl, phenyl, and pyridyl, wherein the phenyl and pyridyl are optionally substituted by 1, 2, or 3 $R^1$ groups;
each $R^1$ is independently selected from the group consisting of H, $C_{1-4}$ alkyl, $C_{1-4}$ haloalkyl, $C_{1-4}$ alkoxy, halo, CN, $NO_2$, $NH_2$, OH, $C(O)C_{1-4}$ alkyl, $C(O)N(C_{1-4}$ alkyl$)_2$, and 5-6 membered heterocycloalkyl;
or, alternatively, $R^{N2}$ and $R^1$, together with the atoms to which they are attached, come together to form a 5-6 membered heterocycloalkyl group;
or, alternatively, $R^{N2}$ and $L^1$ come together to form a 5-6 membered heterocycloalkyl group; and
each $R^2$ is independently selected from the group consisting of $C_{1-4}$ alkyl, halo, CN, $NH_2$, —$C(O)C_{1-4}$ haloalkyl, —$NHC(O)C_{1-4}$ haloalkyl, —$NHSO_2$—$C_{1-4}$ alkyl, and phenoxy;
with the proviso that if $L^1$ is cyclopropylene then at least one $R^1$ group is CN;
wherein the compound of Formula II is not a compound selected from the group consisting of:

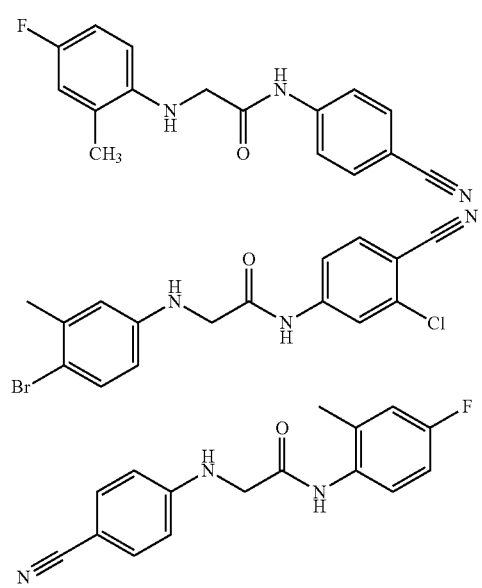

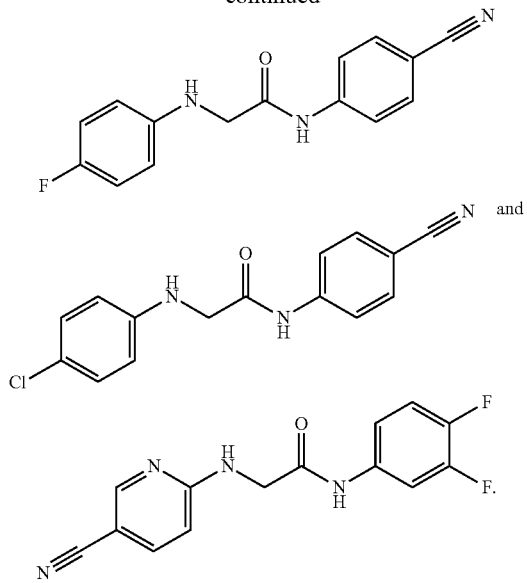

In some embodiments, the infection is a Gram negative infection.

In some embodiments, the Gram negative infection is caused by *Pseudomonas aeruginosa*.

In some embodiments, the subject has a lung infection.

In some embodiments, the subject is selected from the group consisting of a trauma subject, a subject suffering from a burn or skin wound, a subject having a lung infection, a subject having pneumonia, a subject having septic shock, a subject having urinary tract infection, a subject having a gastrointestinal infection, a subject having an infection of the skin and soft tissue, a subject having an infection that modulates gut permeability, and a subject having an infection that modulates brain function, or any combination thereof.

The present application further provides a method of reducing bacterial tolerance in a subject, the method comprising administering to the subject a therapeutically effective amount of a compound of Formula II:

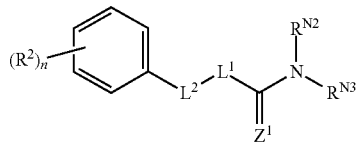

or a pharmaceutically acceptable salt thereof, wherein:

$Z^1$ is selected from the group consisting of O and S;

$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of O, $NR^{N1}$, C(O), C(S), ($C_{1-4}$ alkylene)-C(O), $NR^{N1}$C(O), $NR^{N1}$C(S), and $NR^{N1}$SO$_2$;

or, alternatively, $L^2$ is absent;

$R^{N1}$ and $R^{N2}$ are each independently selected from the group consisting of H and $C_{1-4}$ alkyl;

$R^{N3}$ is selected from the group consisting of $C_{1-4}$ haloalkyl, NH($C_{1-4}$ alkyl), cyclopropyl, phenyl, and pyridyl, wherein the phenyl and pyridyl are optionally substituted by 1, 2, or 3 independently selected $R^1$ groups;

each $R^1$ is independently selected from the group consisting of H, $C_{1-4}$ alkyl, $C_{1-4}$ haloalkyl, $C_{1-4}$ alkoxy, halo, CN, NO$_2$, NH$_2$, OH, C(O)$C_{1-4}$ alkyl, C(O)N($C_{1-4}$ alkyl)$_2$, and 5-6 membered heterocycloalkyl;

or, alternatively, $R^{N2}$ and $R^1$, together with the atoms to which they are attached, come together to form a 5-6 membered heterocycloalkyl group;

or, alternatively, $R^{N2}$ and $L^1$ come together to form a 5-6 membered heterocycloalkyl group; and each $R^2$ is independently selected from the group consisting of $C_{1-4}$ alkyl, halo, CN, NH$_2$, —C(O)$C_{1-4}$ haloalkyl, —NHC(O)$C_{1-4}$ haloalkyl, —NHSO$_2$—$C_{1-4}$ alkyl, and phenoxy;

with the proviso that if L is cyclopropylene then at least one $R^1$ group is CN;

wherein the compound of Formula II is not a compound selected from the group consisting of:

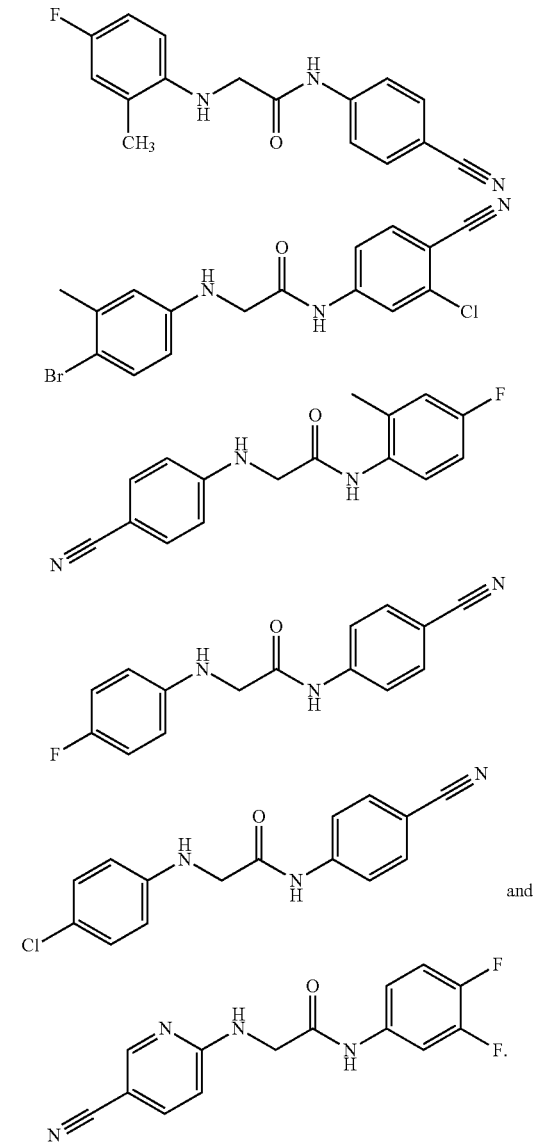

The present application further provides a method of reducing intestinal permeability in a subject in need thereof, comprising administering to the subject a therapeutically effective amount of a compound of Formula II:

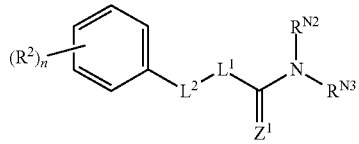

II or a pharmaceutically acceptable salt thereof, wherein:

$Z^1$ is selected from the group consisting of O and S;

$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of O, $NR^{N1}$, C(O), C(S), ($C_{1-4}$ alkylene)-C(O), $NR^{N1}C(O)$, $NR^{N1}C(S)$, and $NR^{N1}SO_2$;

or, alternatively, $L^2$ is absent;

$R^{N1}$ and $R^{N2}$ are each independently selected from the group consisting of H and $C_{1-4}$ alkyl;

$R^{N3}$ is selected from the group consisting of $C_{1-4}$ haloalkyl, NH($C_{1-4}$ alkyl), cyclopropyl, phenyl, and pyridyl, wherein the phenyl and pyridyl are optionally substituted by 1, 2, or 3 independently selected $R^1$ groups;

each $R^1$ is independently selected from the group consisting of H, $C_{1-4}$ alkyl, $C_{1-4}$ haloalkyl, $C_{1-4}$ alkoxy, halo, CN, $NO_2$, $NH_2$, OH, $C(O)C_{1-4}$ alkyl, $C(O)N(C_{1-4}$ alkyl$)_2$, and 5-6 membered heterocycloalkyl;

or, alternatively, $R^{N2}$ and $R^1$, together with the atoms to which they are attached, come together to form a 5-6 membered heterocycloalkyl group;

or, alternatively, $R^{N2}$ and $L^1$ come together to form a 5-6 membered heterocycloalkyl group; and each $R^2$ is independently selected from the group consisting of $C_{1-4}$ alkyl, halo, CN, $NH_2$, —C(O)$C_{1-4}$ haloalkyl, —NHC(O)$C_{1-4}$ haloalkyl, —NHSO$_2$—$C_{1-4}$ alkyl, and phenoxy;

with the proviso that if L is cyclopropylene then at least one R group is CN;

wherein the compound of Formula II is not a compound selected from the group consisting of:

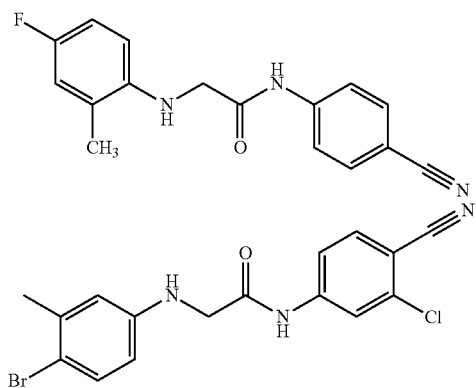

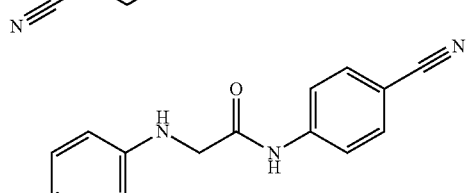

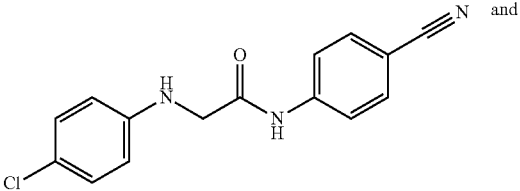

and

In some embodiments, the subject is suffering from a burn, intestinal hyperpermeability, or a combination thereof. In some embodiments, the subject has been identified has having burn-site infection. In some embodiments, the subject has been identified as having a bacteria tolerant infection.

In some embodiments, the method provided herein further comprises administering to the subject an antibiotic. In some embodiments, the antibiotic is selected from the group consisting of penicillin, a cephalosporin, a carbacephem, a cephamycin, a carbapenem, a monobactam, a quinolone, a tetracycline, an aminoglycoside, a macrolide, a glycopeptide, a chloramphenicol, a glycylcycline, a licosamide, a lipopeptide, an oxazolidinone, and a fluoroquinolone.

In some embodiments of the methods provided herein, $Z^1$ is O. In some embodiments of the methods provided herein, $Z^1$ is S.

In some embodiments of the methods provided herein, $L^2$ is absent. In some embodiments of the methods provided herein, $L^2$ is selected from the group consisting of O, $NR^{N1}$, C(O), C(S), ($C_{1-4}$ alkylene)-C(O), $NR^{N1}C(O)$, $NR^{N1}C(S)$, and $NR^{N1}SO_2$. In some embodiments of the methods provided herein, $L^2$ is selected from the group consisting of $NR^{N1}$, C(O), $NR^{N1}C(O)$, $NR^{N1}C(S)$, and $NR^{N1}SO_2$.

In some embodiments of the methods provided herein, $R^{N1}$ is selected from the group consisting of H and methyl. In some embodiments of the methods provided herein, $L^2$ is selected from the group consisting of $NR^{N1}$ and NHC(O).

In some embodiments of the methods provided herein, $R^{N2}$ is selected from the group consisting of H and methyl. In some embodiments of the methods provided herein, $R^{N2}$ and $L^1$, together with the atoms to which they are attached, come together to form a 5-6 membered heterocycloalkyl group. In some embodiments of the methods provided herein, $R^{N2}$ and $L^1$, together with the atoms to which they are attached, come together to form a pyrrolidinone group.

In some embodiments of the methods provided herein, $R^{N3}$ is selected from the group consisting of phenyl and pyridyl, wherein the phenyl and pyridyl are each optionally substituted by 1, 2, or 3 independently selected $R^1$ groups.

In some embodiments of the methods provided herein, each $R^1$ is independently selected from the group consisting of H, methyl, trifluoromethyl, methoxy, halo, CN, $NO_2$, $NH_2$, OH, $C(O)CH_3$, $C(O)N(CH_3)_2$, morpholinyl, and pyrrolidinone.

In some embodiments of the methods provided herein, each $R^2$ is independently selected from the group consisting of methyl, fluoro, iodo, CN, $NH_2$, —$C(O)CF_3$, —NHC(O)$CF_3$, —$NHSO_2CH_2CH_3$, and phenoxy.

In some embodiments of the methods provided herein:

$Z^1$ is selected from the group consisting of O and S;

$L^1$ is selected from the group consisting of methylene, ethylene, ethen-1,2-diyl, fluoromethylene, cyclopropylene, and hydroxypropylene;

$L^2$ is selected from the group consisting of O, $NR^{N1}$, C(O), $NR^{N1}C(O)$ $NR^{N1}C(S)$, and $NR^{N1}SO_2$;

or, alternatively, $L^2$ is absent;

$R^{N1}$ is selected from the group consisting of H and methyl;

$R^{N2}$ is selected from the group consisting of H and methyl;

$R^{N3}$ is selected from the group consisting of phenyl and pyridyl, wherein the phenyl and pyridyl are each optionally substituted by 1, 2, or 3 independently selected $R^1$ groups;

each $R^1$ is independently selected from the group consisting of H, methyl, trifluoromethyl, methoxy, halo, CN, $NO_2$, $NH_2$, OH, $C(O)CH_3$, $C(O)N(CH_3)_2$, morpholinyl, and pyrrolidinone; and each $R^2$ is independently selected from the group consisting of methyl, fluoro, iodo, CN, $NH_2$, —$C(O)CF_3$, —NHC(O)$CF_3$, —$NHSO_2CH_2CH_3$, and phenoxy.

In some embodiments of the methods provided herein:

$Z^1$ is O;

$L^1$ is selected from the group consisting of methylene, ethylene, ethen-1,2-diyl, fluoromethylene, cyclopropylene, and hydroxypropylene;

$L^2$ is selected from the group consisting of $NR^{N1}$ and $NR^{N1}C(O)$;

or, alternatively, $L^2$ is absent;

$R^{N1}$ is selected from the group consisting of H and methyl;

$R^{N2}$ is selected from the group consisting of H and methyl;

$R^{N3}$ is selected from the group consisting of phenyl and pyridyl, wherein the phenyl and pyridyl are each optionally substituted by 1, 2, or 3 independently selected $R^1$ groups;

each $R^1$ is independently selected from the group consisting of H, methyl, trifluoromethyl, methoxy, halo, CN, $NO_2$, $NH_2$, OH, $C(O)CH_3$, $C(O)N(CH_3)_2$, morpholinyl, and pyrrolidinone; and each $R^2$ is independently selected from the group consisting of methyl, fluoro, iodo, CN, $NH_2$, —$C(O)CF_3$, —NHC(O)$CF_3$, —$NHSO_2CH_2CH_3$, and phenoxy.

In some embodiments, the compound of Formula II is a compound of Formula II-a, II-b, II-c, II-d, II-e, II-f, or II-g:

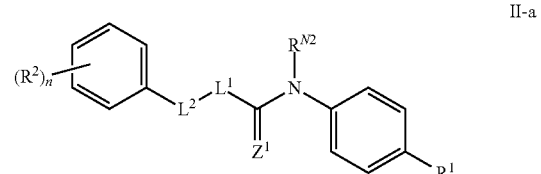

II-a

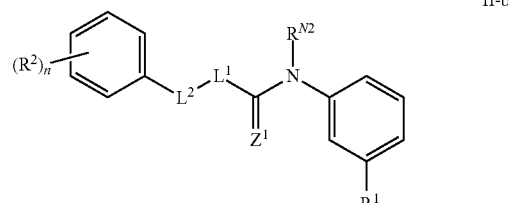

II-b

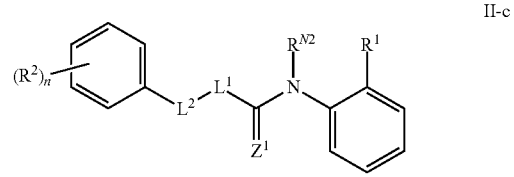

II-c

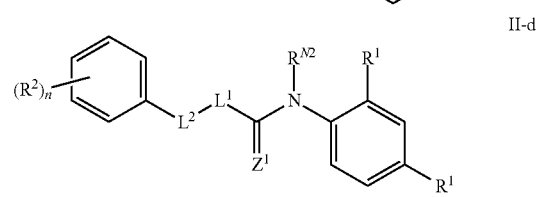

II-d

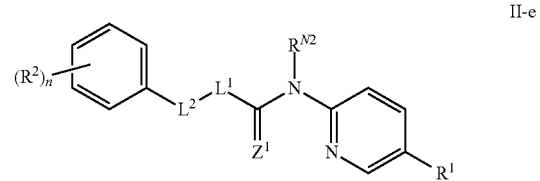

II-e

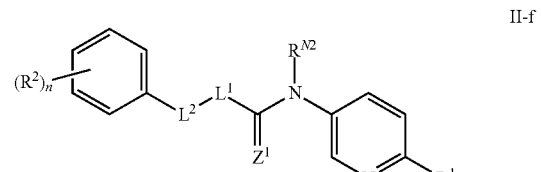

II-f

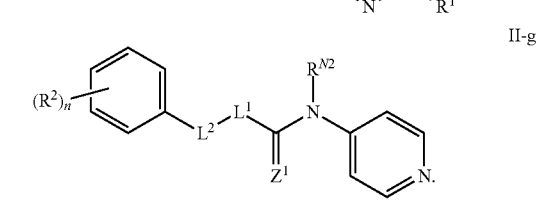

II-g

In some embodiments, the compound of Formula II is a compound of Formula II-h, II-i, II-j, II-k, II-l, II-m, II-n, II-o:

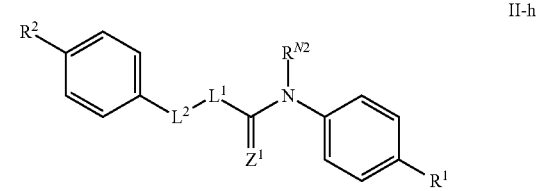

II-h

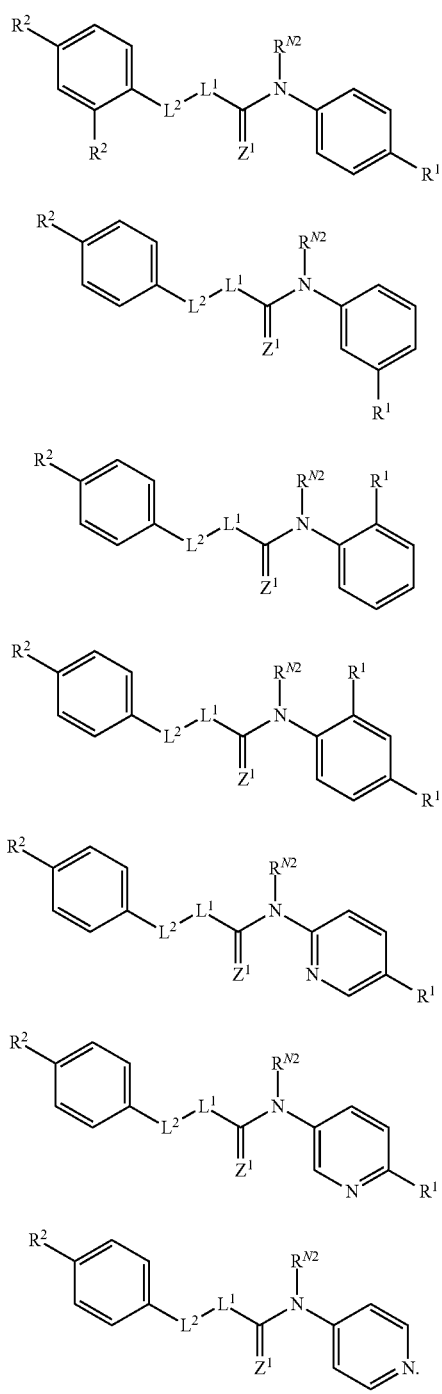
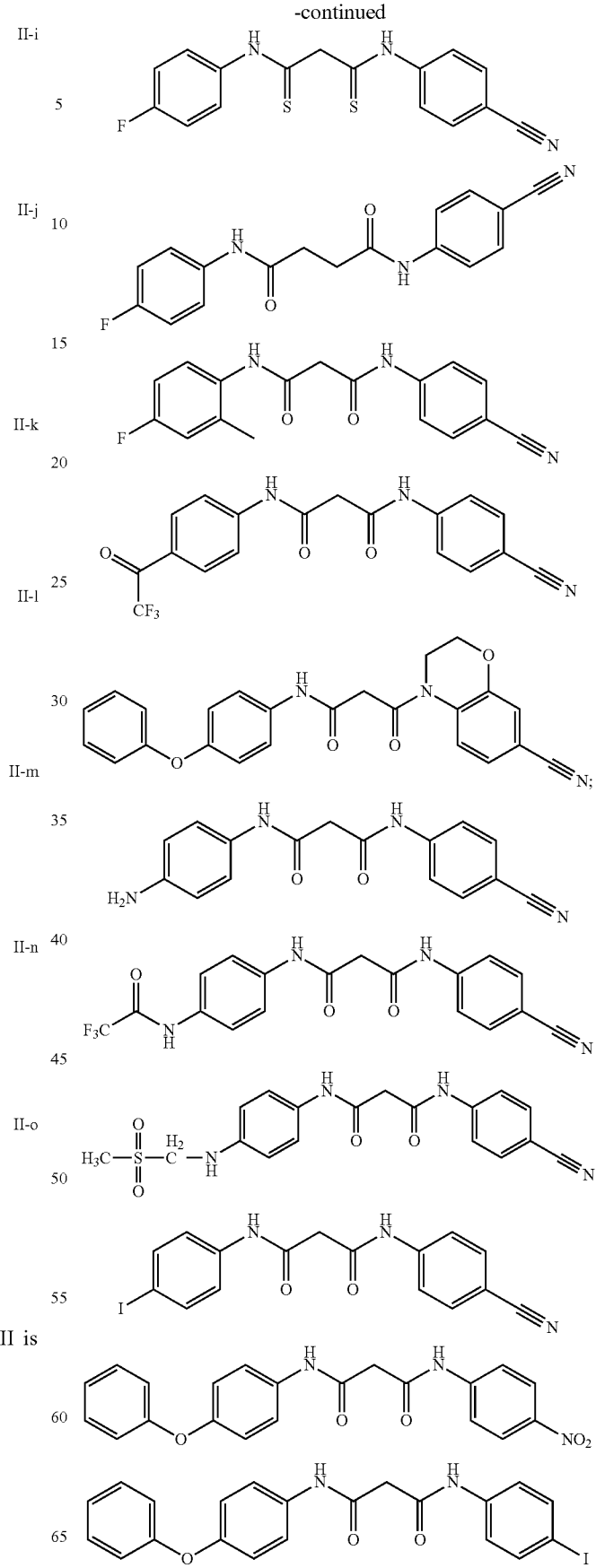
In some embodiments, the compound of Formula II is selected from the group consisting of:
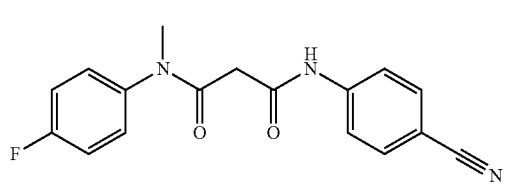

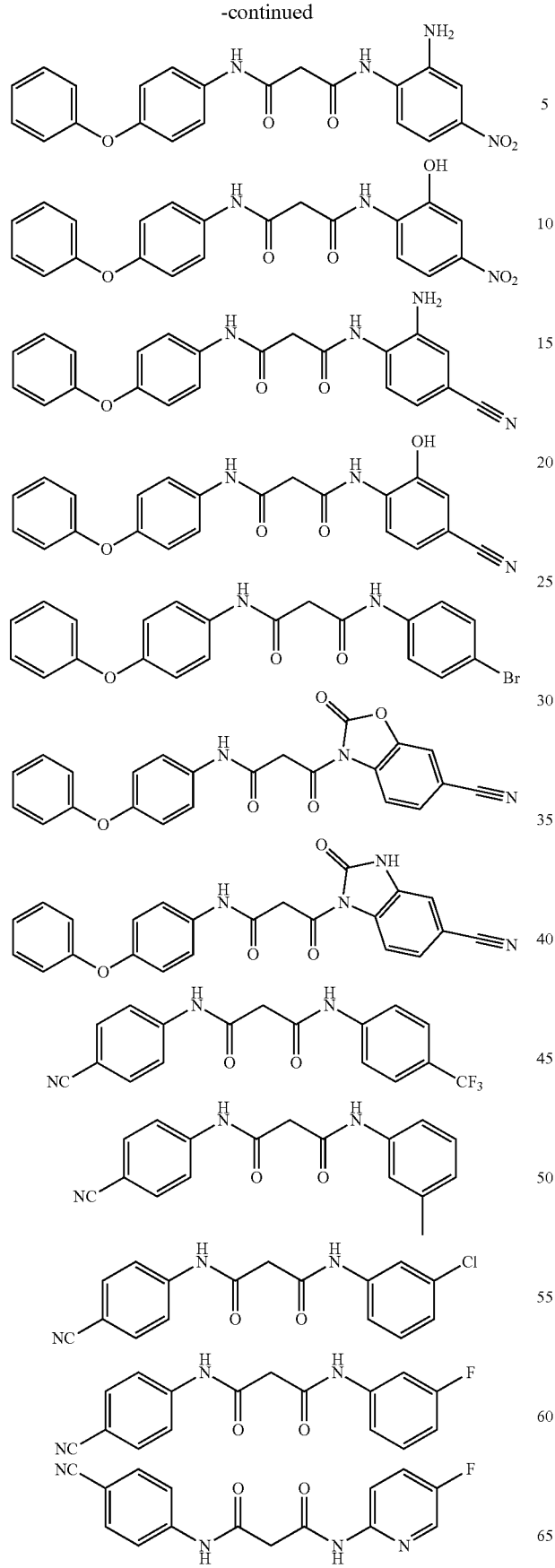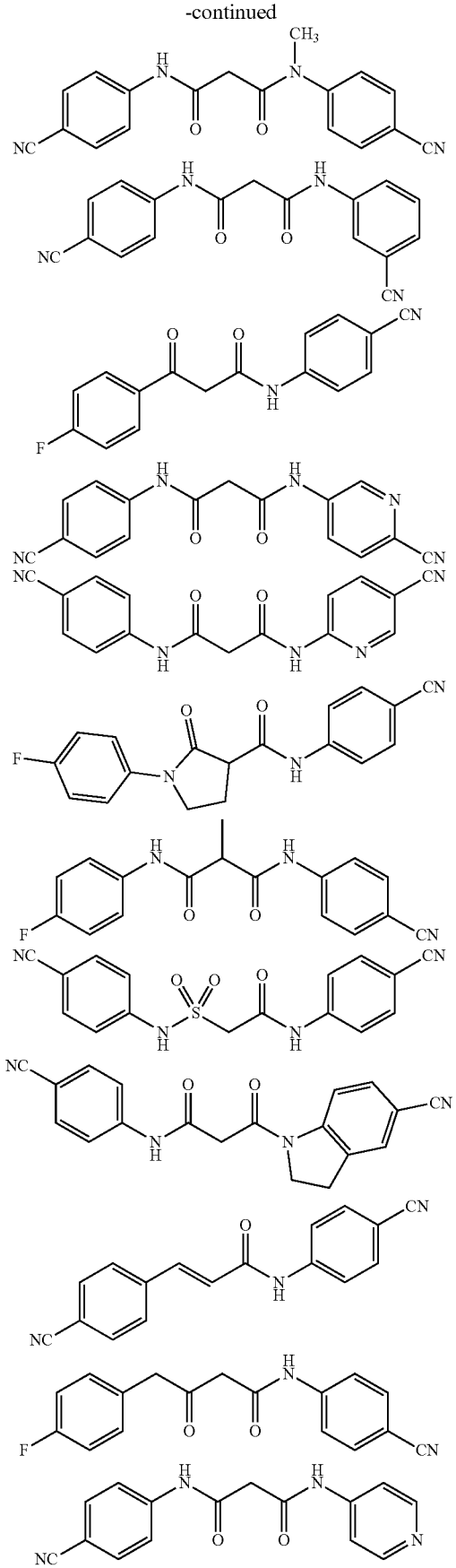

-continued
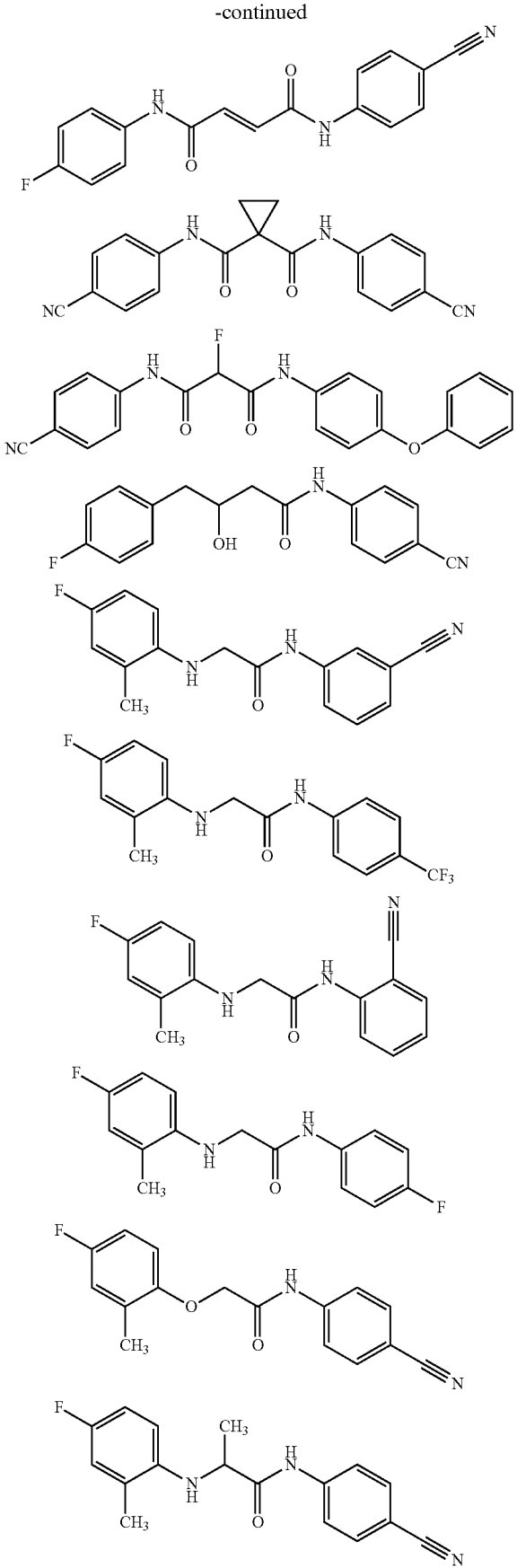
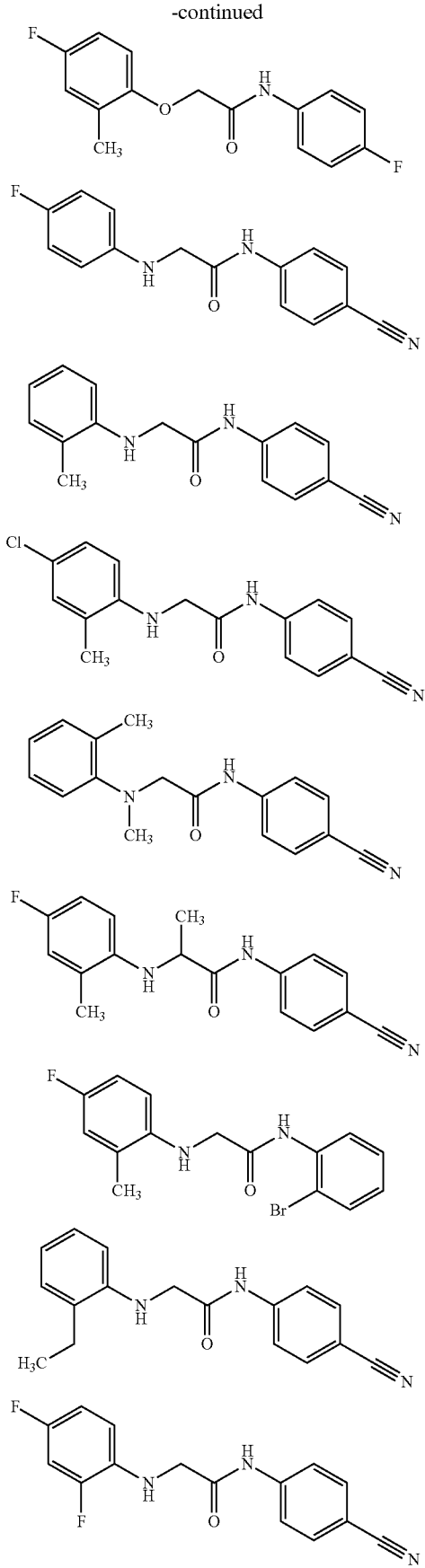

-continued
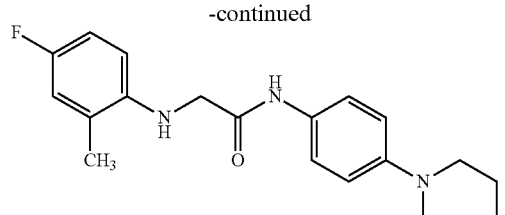
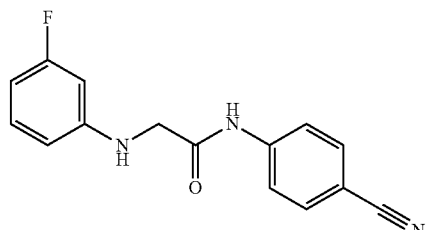
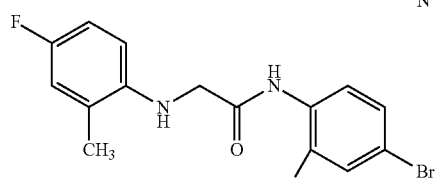
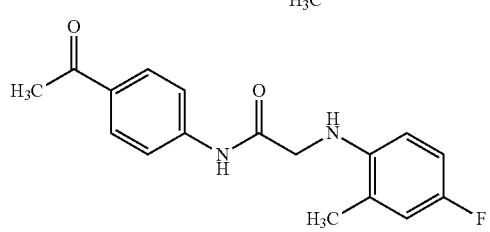
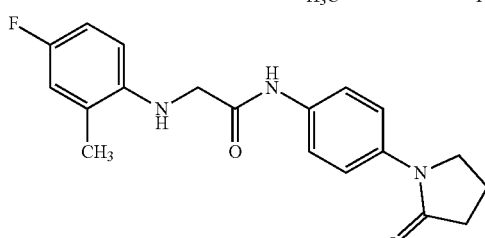
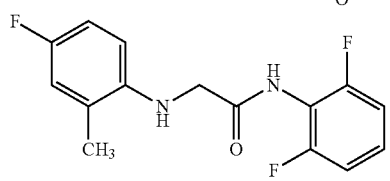
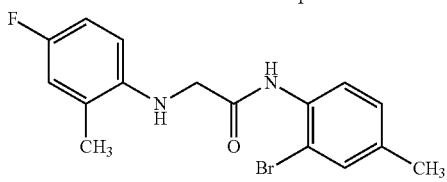
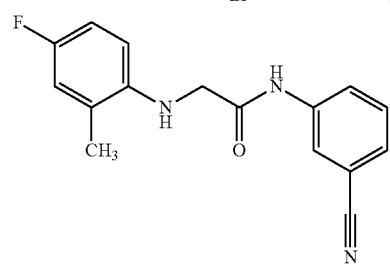
-continued
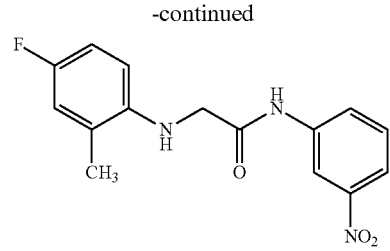
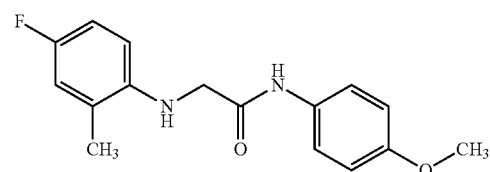
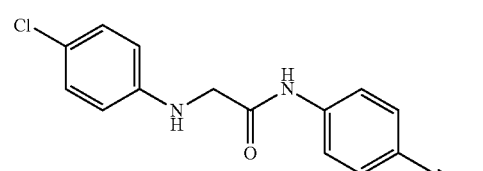
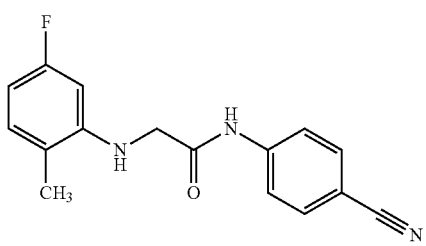
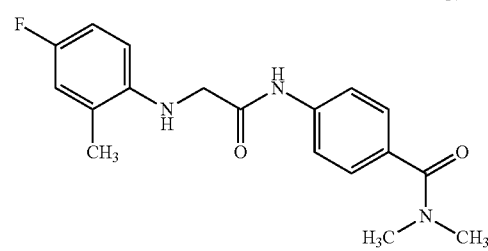
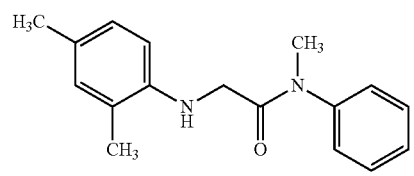
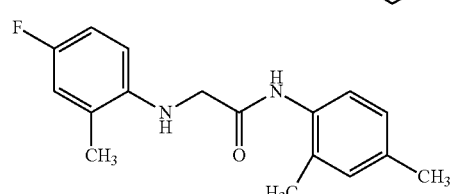
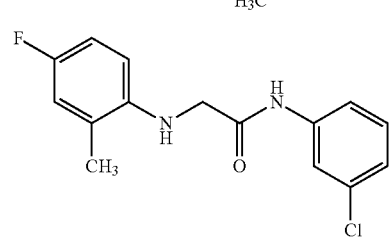

-continued
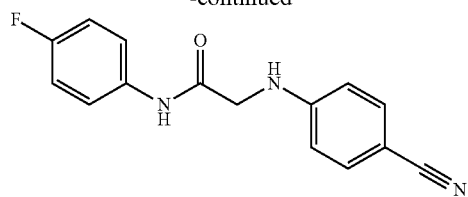
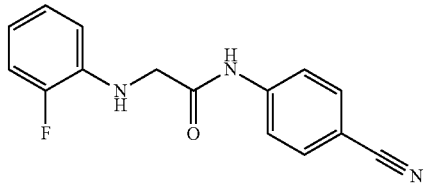
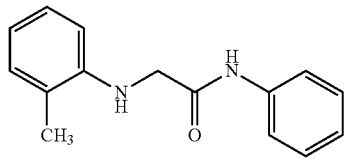
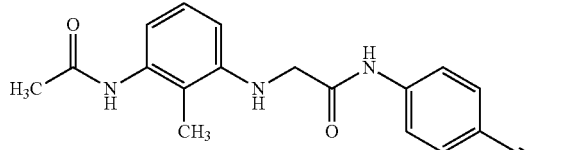
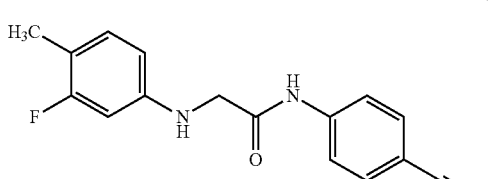
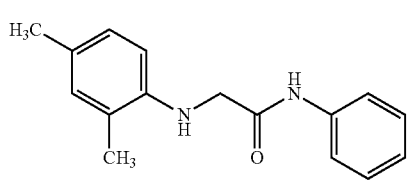
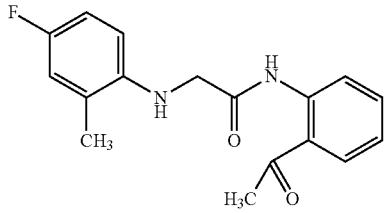
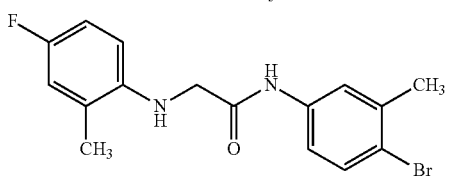
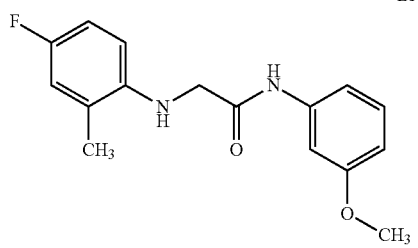
-continued
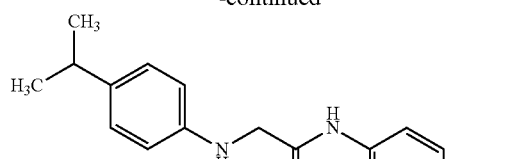
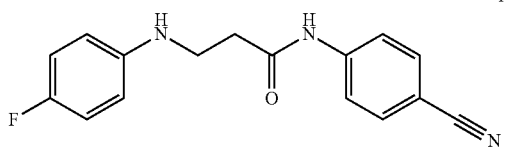
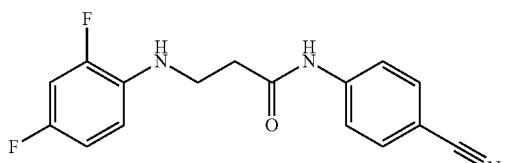
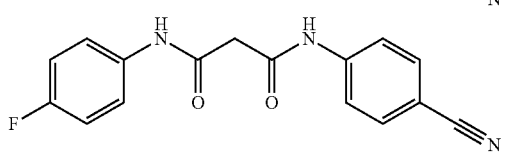
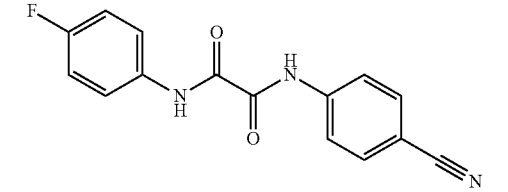
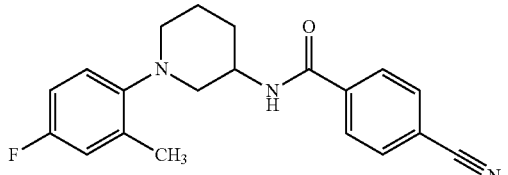
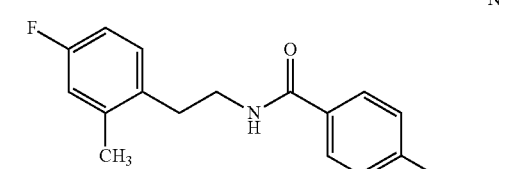
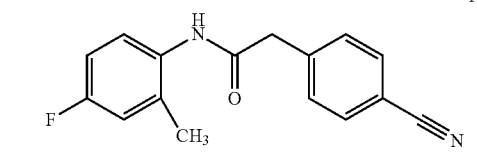
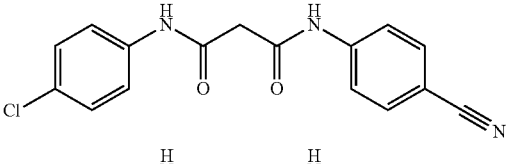
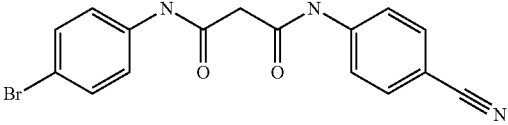

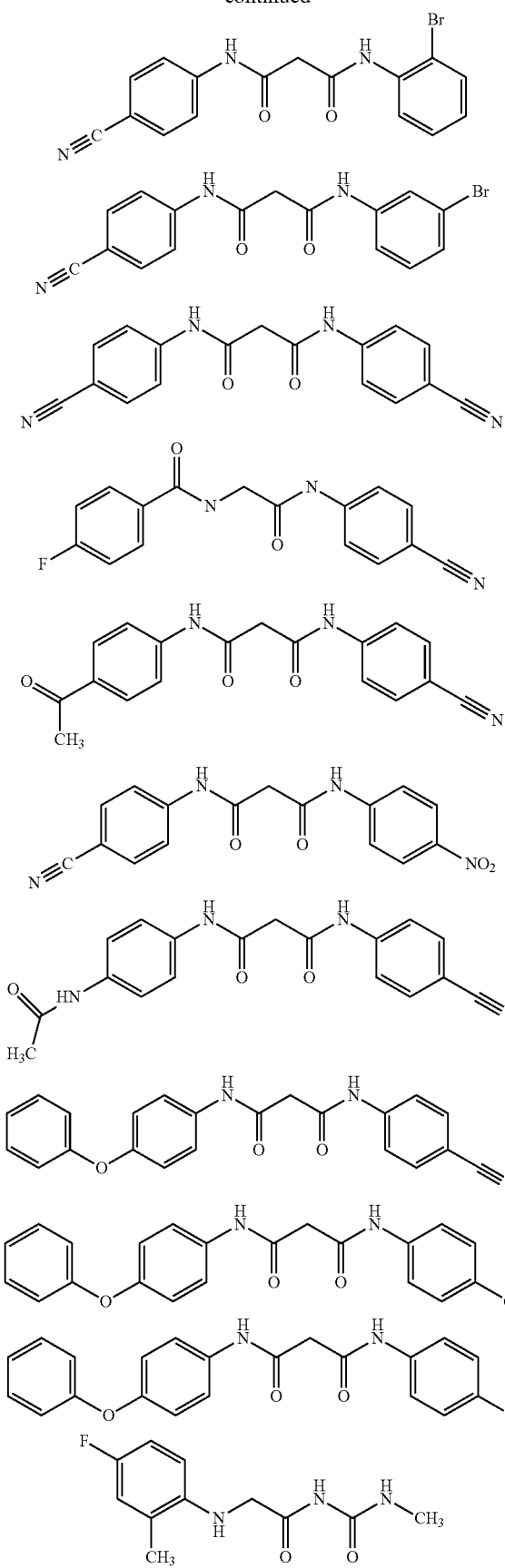
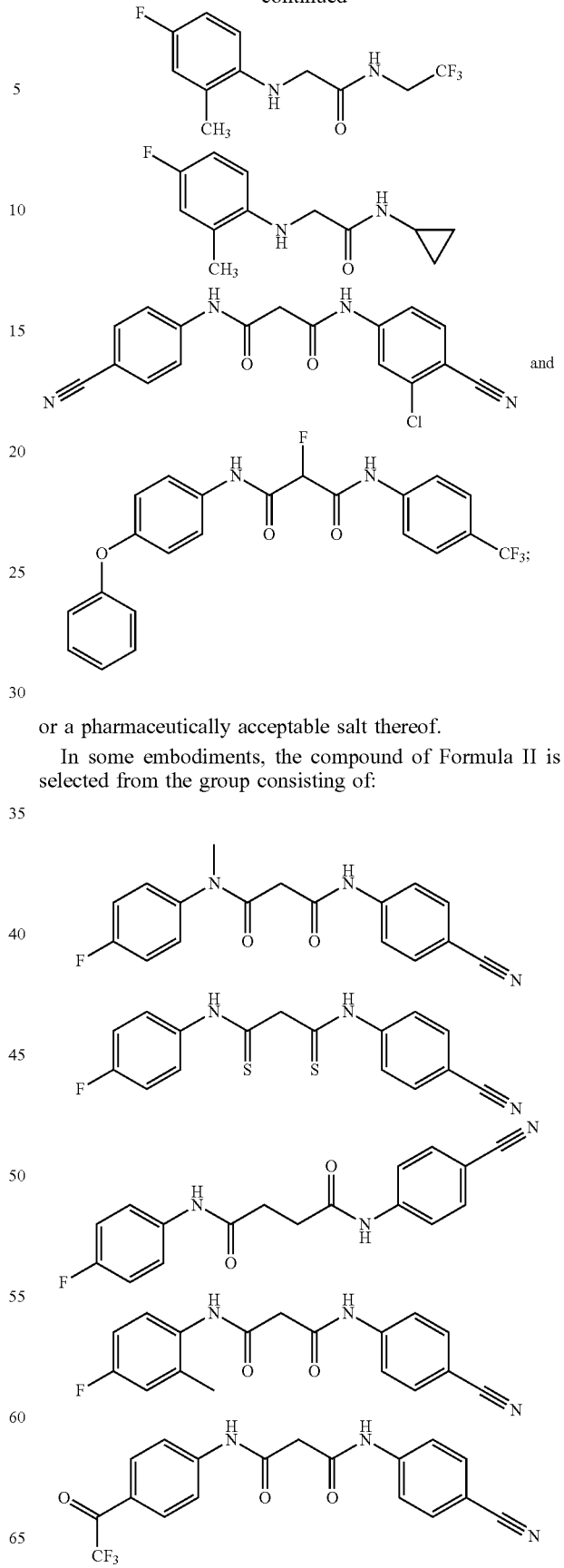
or a pharmaceutically acceptable salt thereof.
In some embodiments, the compound of Formula II is selected from the group consisting of:

33
-continued
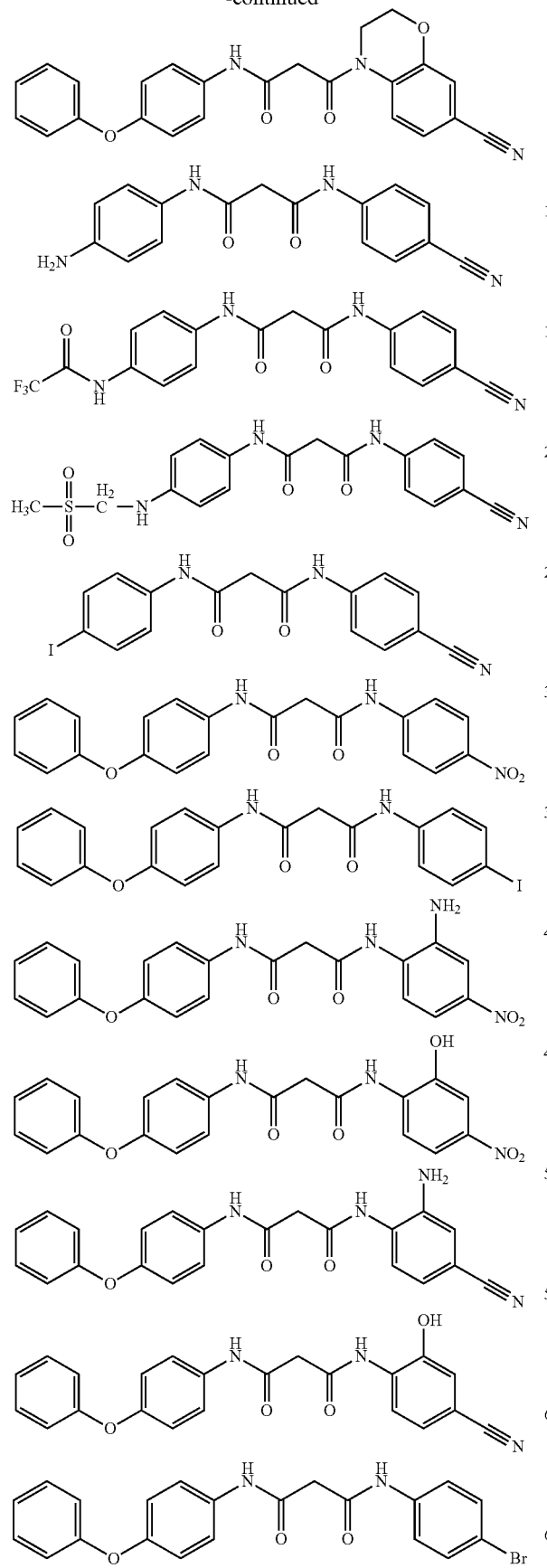
34
-continued
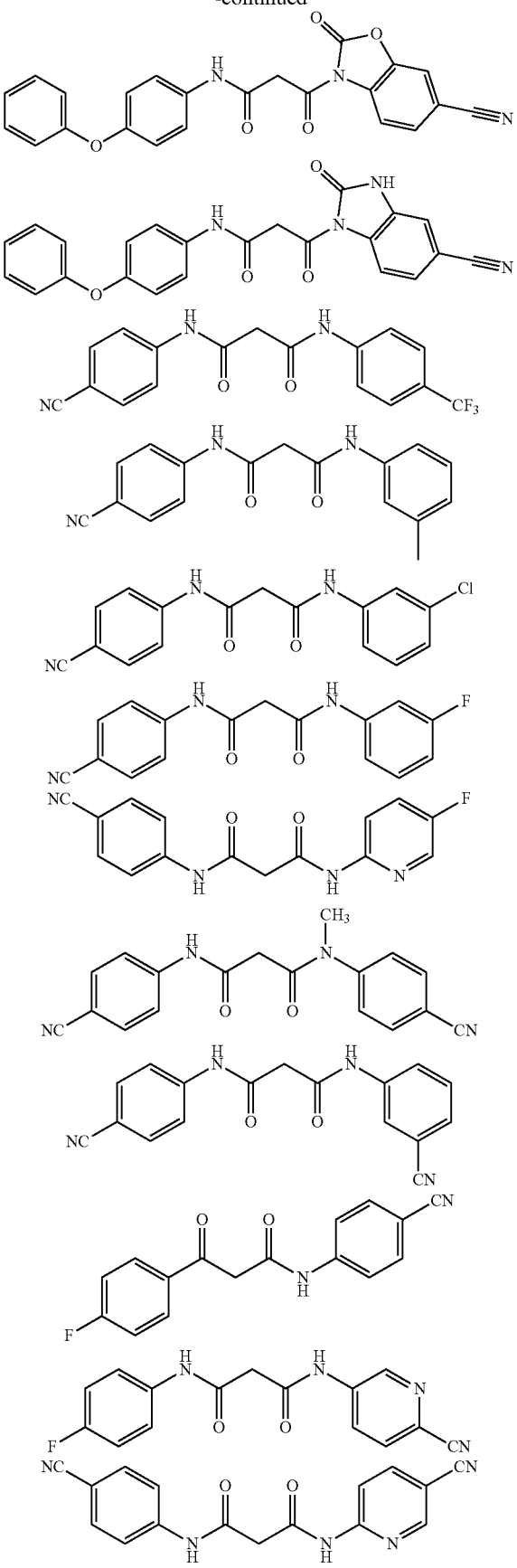

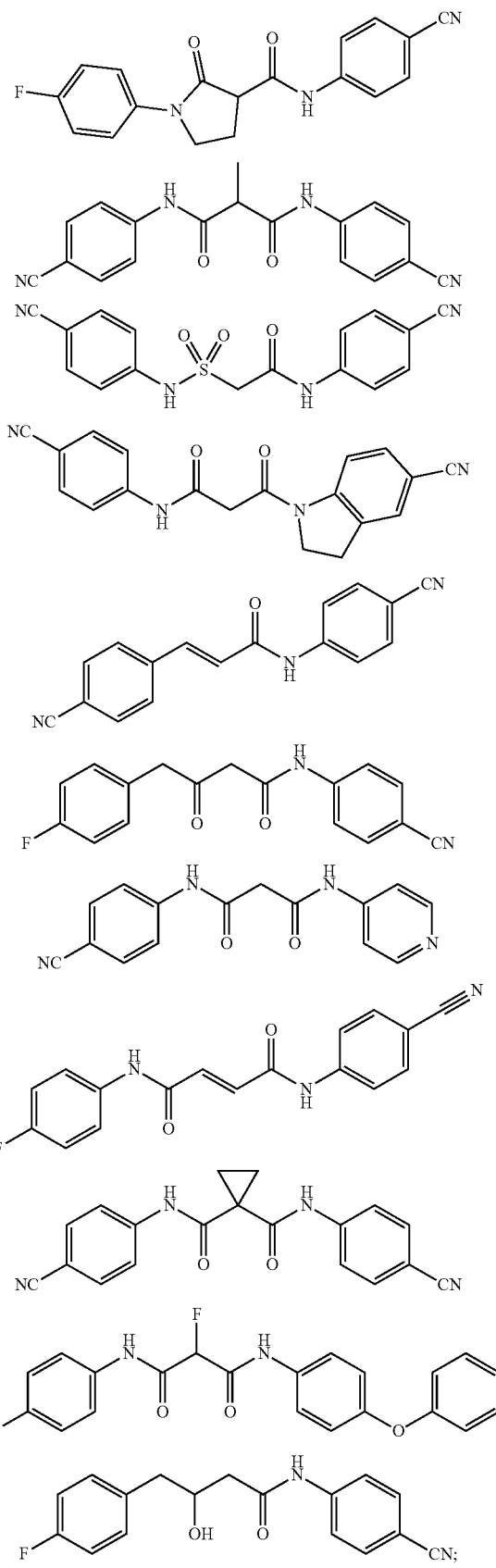
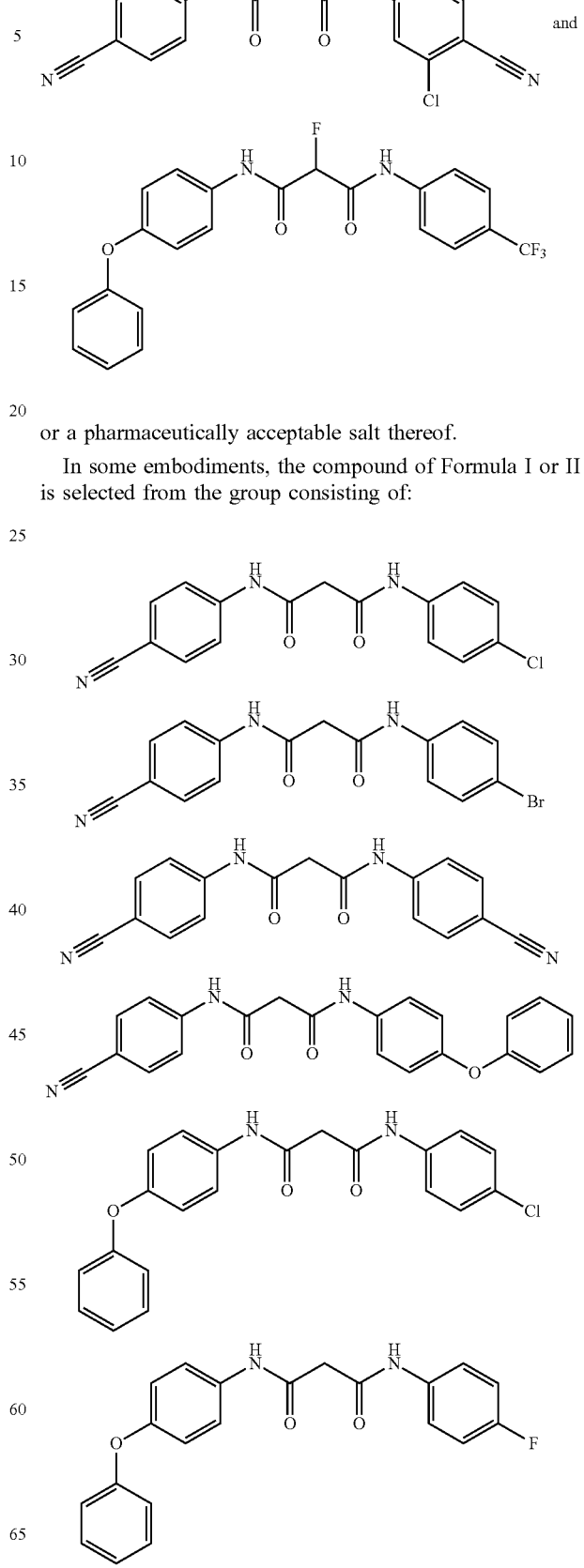
or a pharmaceutically acceptable salt thereof.
In some embodiments, the compound of Formula I or II is selected from the group consisting of:

-continued

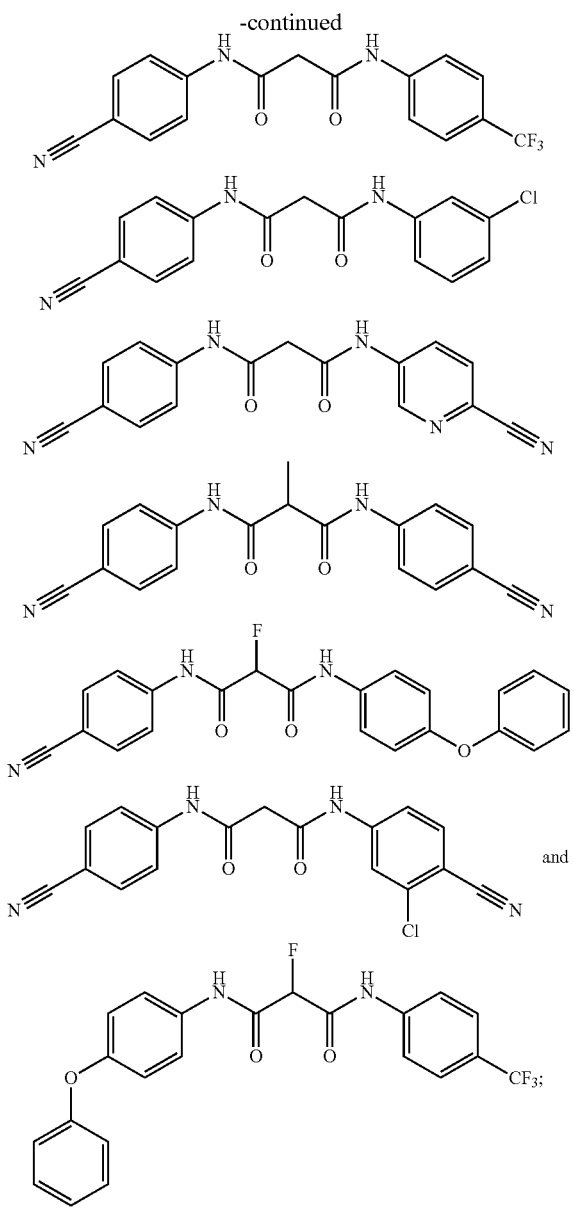

or a pharmaceutically acceptable salt thereof.

In some embodiments, the compound of Formula I or Formula II is:

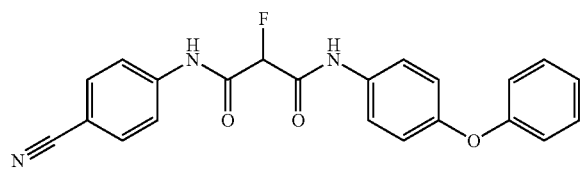 [SMILES: N#Cc1ccc(NC(=O)C(F)C(=O)Nc2ccc(Oc3ccccc3)cc2)cc1]

or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIGS. 4A-4G show a summary of tabulated results for a representative group of compounds tested in the screening assays described in Example 2.

FIGS. 5A-5C: Thigh model: treatment was initiated 4 h post-infection and repeated at 4, 8, 12 and 18 hours. FIG. 5A: monotherapy with Compound 72, 10 mg/kg (P<0.05 Mann Whitney test); FIG. 5B-5C. Combinatorial: Compound 72 (10 mg/kg) plus Ciprofloxacin 1 mg/kg (subtherapeutic dose) (FIG. 5B: P<0.05; Figure C: P>0.05; Mann Whitney test). CFUs were assessed 24 h post-infection in the thigh (FIG. 5A), liver (FIG. 5B) and spleen (FIG. 5C). Compound 72 was administered subcutaneously and ciprofloxacin intraperitoneally (IP). FIG. 5D shows that Compound 54 potentiates ciprofloxacin efficacy in reducing PA cells in mice lungs and significantly reduced bacterial load. Mice were infected with $5 \times 10^6$ PA14 cells lung infection model. Compound 54 (10 mg/kg) plus ciprofloxacin 1 mg/kg treatment (subtherapeutic dose) was initiated at 2 h post-infection and repeated at 6, 12, and 18 h post-infection. CFUs were assessed 24 h post-infection in the lung. Compound 54 was administered subcutaneously and ciprofloxacin intraperitoneally (IP).

FIG. 6A shows compound solubility assessed in PBS at pH 7.4. FIGS. 6B-6C shows hepatic clearance measured in human (FIG. 6B) and mouse liver microsomes (FIG. 6C). FIG. 6D shows plasma protein binding measured in human plasma. FIG. 6E shows compound tissue binding measured in mouse lung.

FIG. 9A shows pyocyanin production; FIG. 9B shows pqsA gene expression.

DETAILED DESCRIPTION

Figure 1A:
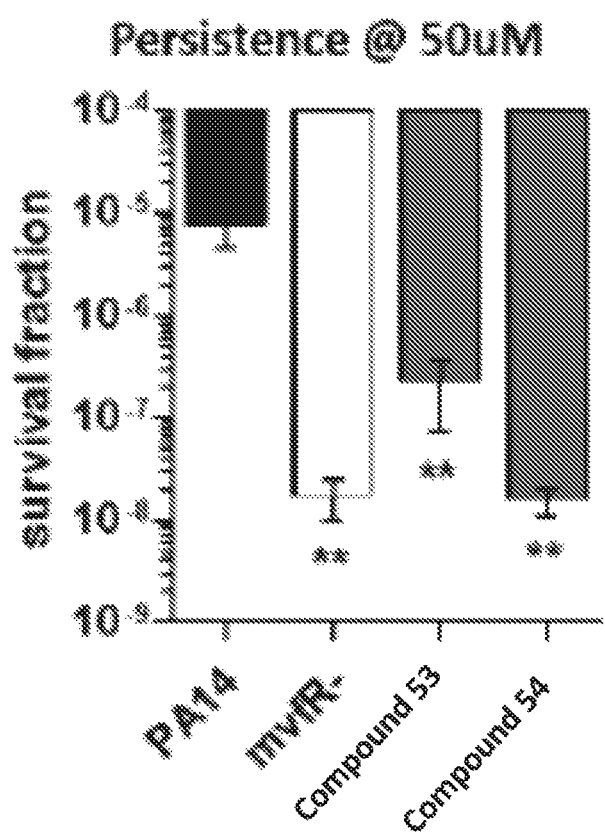
FIG. 1A shows persistence of P. aeruginosa upon treatment with Compound 53 or Compound 54. Wild type (PA14) P. aeruginosa was grown in liquid culture with or without Compound 54 and treated with meropenem according to published procedures (see e.g., Starkey et al, PLoS Pathog. 2014, 10:e1004321). Data are expressed as fraction of original culture surviving antibiotic treatment.
Figure 1B:
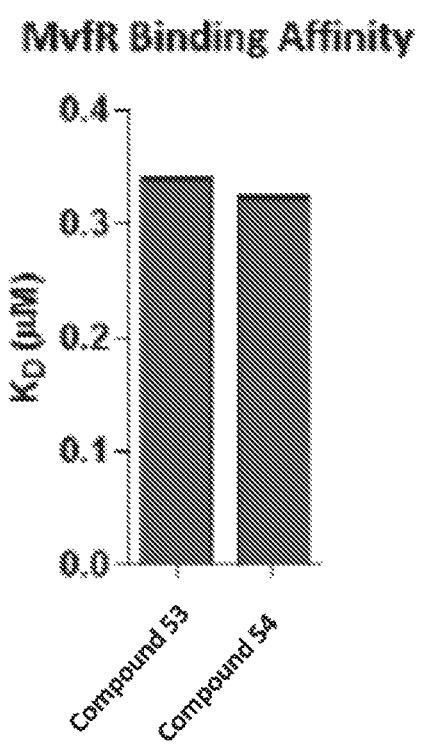
FIG. 1B shows results of affinity binding studies for Compounds 53-54 for MvfR.
Figure 1C:
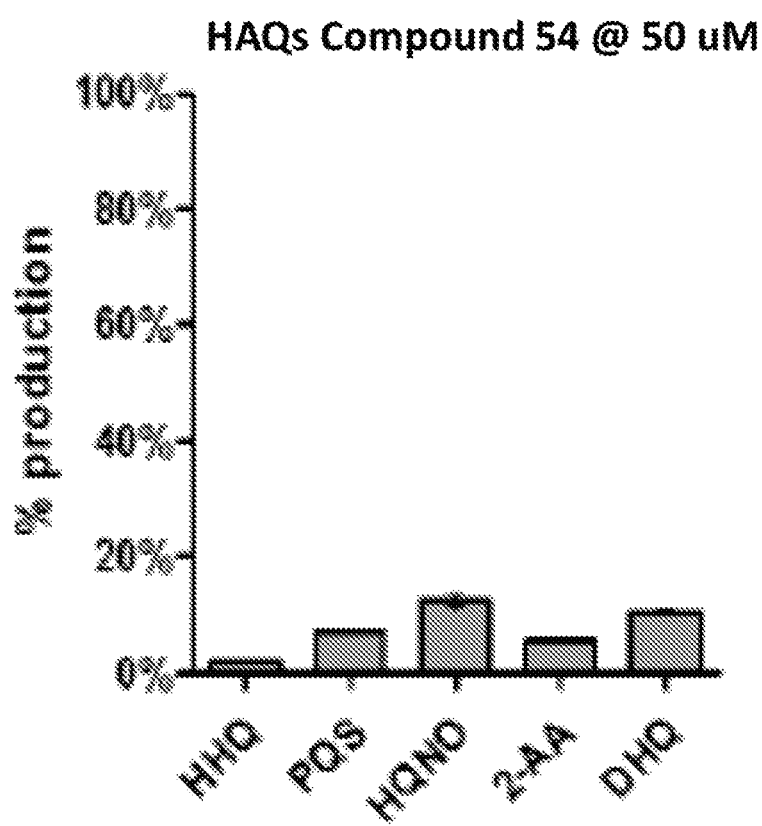
FIG. 1C shows hydroxy-2-alkylquinoline (HAQ) production from a liquid culture grown with 50 M Compound 54.
Figure 1D:
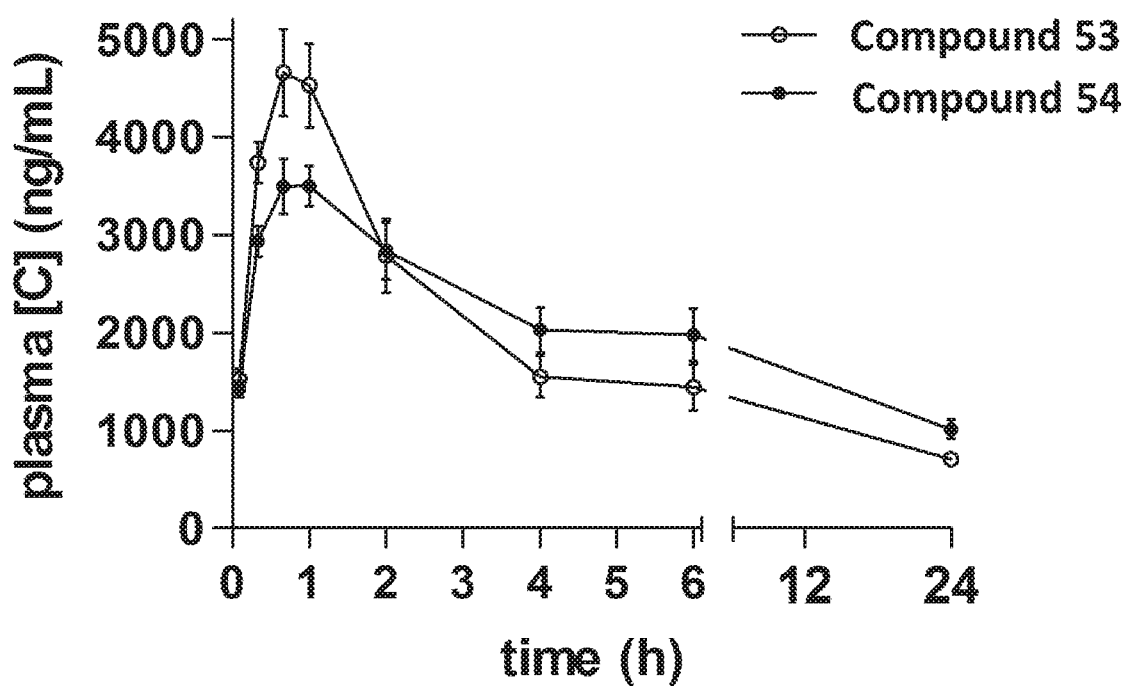
FIG. 1D shows plasma concentration of Compound 53 and Compound 54 over 24 h after a 10 mg/kg subcutaneous injection in mice.

Many cystic fibrosis (CF) patients will be infected by *P. aeruginosa* during their lifetimes (see e.g., Stefani et al, International *Journal of Medical Microbiology*, 2017; Acosta et al, *Annals of the American Thoracic Society*, 2017, 14:1288-1297). These infections tend to manifest later and are lifelong, causing severe inflammation and ultimately lead to death due to respiratory failure (see e.g., Harun et al, *Paediatric Respiratory Reviews*, 2016, 20:55-66; and Lund-Palau et al, *Expert Rev. Respir. Med.* 2016, 10:685-697). *B. cepacia* complex infections are less common, however these pathogens are associated with a lower long-term survival rate and some infections cause what is known as "cepacia syndrome" which leads to a rapid decline and death (see e.g., Frangolias et al, *Am. J. Respir. Crit. Care Med.* 1999, 160:1572-1577; and Ganesan & Sajjan, *Front Cell Infect. Microbiol.* 2011, 1:25. Furthermore, *B. cepacia* infections can be spread nosocomially (see e.g., O'Malley, C. A.

*Respir. Care,* 2009, 54:641-657), making this type of infection dangerous in the hospital setting. *P. aeruginosa* and *B. cepacia* may co-exist in the lungs of CF patients, both are inherently resistant to antibiotics (see e.g., Poole, K. *Journal of Molecular Microbiology and Biotechnology,* 2001, 3:255-263, and routinely employ virulence and antibiotic tolerance mechanisms to persist in infections (see e.g., Lund-Palau et al, *Expert Rev. Respir. Med.* 2016, 10:685-697; and Lewis & Torres, *Pathog. Dis.* 2016, 74.

Bacterial persistence is observed in a broad range of microbial species. Antibiotic tolerant "persister" cells are responsible for a substantial portion of persistent, chronic and relapsing infections that are prevalent worldwide (see e.g., Fux et al, Trends Microbiol. 2005, 13:34-40. For patients with CF, these bacterial cell subpopulation can cause grave suffering, severe pain, emotional and physical strain, as well as a considerable financial burden for patients and healthcare systems. Biofilm and persister cells formation, contribute to antibiotic tolerance and persistence, and are observed in a number of microbial species. The capacity of bacterial sub-populations, "persisters", to tolerate exposure to normally lethal concentrations of bactericidal antibiotics, which is not due to antibiotic-resistance, has been implicated in antibiotic treatment failures and may account for latent, chronic, and relapsing infections (see e.g., Hogardt & Heesemann, *Int. J. Med. Microbiol.* 2010, 300:557-562; and Amato et al, *Frontiers in Microbiology,* 2014, 5). According to the existing paradigm, these infections can only be suppressed, not eradicated, with conventional antibiotics (see e.g., Amato et al, *Frontiers in Microbiology,* 2014, 5; and Wood et al, *Applied and Environmental Microbiology,* 2013, 79:7116-7121). There are currently no drugs that target the antibiotic tolerant, persister (AT/P) cells which represent a small subpopulation of bacteria that can exist in a semi-dormant state, and thus are not vulnerable to antibiotics (see e.g., Keren et al, *FEMS Microbiol. Lett.* 2004, 230:13-18; Lewis, K. *Nature Reviews Microbiology,* 2007, 5:48-56; and Lewis, K. *Annual Review of Microbiology,* 2010, 64:357-375. Persisting cells can later resume growth when the antimicrobial agent is removed, and their progeny remains sensitive to low concentrations of antimicrobial agents (see e.g., Lewis, K. *Nature Reviews Microbiology,* 2007, 5:48-56). The clinical importance of antibiotic tolerance is highlighted by the many cases in which antibiotics failed to clear CF infections despite the absence of resistant bacteria, and clinical reports suggest that the contribution of tolerance to treatment failure and mortality in some infections can be as significant as the contribution of antibiotic resistance. Thus, there is a need for innovative approaches for the treatment of antibiotic tolerant infections.

Accordingly, the present application provides novel therapeutics for the prevention and control of acute, persistent, chronic, or relapsing bacterial infections that could serve as alternatives or adjuncts to traditional agents (e.g., anti-biotic agents) and to potentiate efficacy of the therapeutic agents. For example, the present application provides methods of treatment which disrupts the bacterial signaling mediating acute and chronic virulence factor expression and AT/P cell formation using a series of inhibitory compounds provided herein. The compounds provided herein target, for example, anti-virulence functions rather than cell viability, thereby should reduce selective pressure for resistance development and preserve the beneficial microbiota.

Moreover, the compounds provided herein may provide a polypharmacological approach, silencing two targets in the same QS pathway, MvfR and PqsBC, (see e.g., data reported for benzamide benzamidazole compounds in Maura et al, *ACS Chemical Biology,* 2017, 12:1435-1443). MvfR is the transcriptional regulator and PqsBC is an enzyme complex responsible for production of PQS, HHQ and 60 other molecules, many of which are involved in the acute virulence and persistence of PA and Bcc. Polypharmacology, or simultaneously inhibiting multiple targets involved in the same disease, has been shown to have a significant impact on treatment efficacy in various diseases, including cancer, (see e.g., Tolaney et al, *N. Eng. J. Med.* 2015, 372:134-141; and Robert et al, *N. Eng. J. Med.* 2015, 372:30-39; bacterial and viral infections (see e.g., Diacon et al, *N. Engl. J. Med.* 2009, 360:2397-2405; Hilf et al, *Am. J. Med.* 1989, 87:540-546; and Gandhi & Gandhi, *N. Engl. J. Med.* 2014, 371: 248-259, high blood pressure (see e.g., Sever & Messerli, *Eur. Heart J.* 2011, 32:2499-2506), asthma (see e.g., Kerstjens et al, *New Engl. J. Med.* 2012, 367:1198-1207), and hormone-related diseases (see e.g., Vilar et al, *Pituitary,* 2015, 18:253-262) in clinical settings. Multi-target effects are most frequently obtained by combining selective single-target agents that can either act additively, when the resulting activity is the outcome of their combined individual effects, or synergistically, whereby the combined effect is greater than the sum of their separate responses. Both effects appear to have favorable outcomes and were reported to lower resistance development in cancer and microbial infections (see e.g., Samanta et al, *Proc. Natl. Acad Sci. U.S.A.,* 2014, 111:E5429-E5438; and Worthington & Melander, *Trends Biotechnol.* 2013, 31:177-184). Without being bound by theory, it is believed that disruption of infochemical-dependent virulence and AT/P formation in vivo by the inhibitors described herein will limit persistence, enhance bacterial clearance, and reduce bacterially-induced damage and inflammation in the lungs in a polymicrobial setting.

Compounds

The present application provides a compound of Formula II:

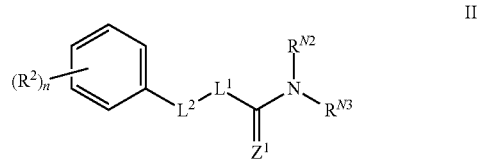

or a pharmaceutically acceptable salt thereof, wherein:

$Z^1$ is selected from the group consisting of O and S;

$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of O, $NR^{N1}$, C(O), C(S), ($C_{1-4}$ alkylene)-C(O), $NR^{N1}C(O)$, $NR^{N1}C(S)$, and $NR^{N1}SO_2$;

or, alternatively, $L^2$ is absent;

$R^{N1}$ and $R^{N2}$ are each independently selected from the group consisting of H and $C_{1-4}$ alkyl;

$R^{N3}$ is selected from the group consisting of $C_{1-4}$ haloalkyl, NH($C_{1-4}$ alkyl), cyclopropyl, phenyl, and pyridyl, wherein the phenyl and pyridyl are optionally substituted by 1, 2, or 3 $R^1$ groups;

each $R^1$ is independently selected from the group consisting of H, $C_{1-4}$ alkyl, $C_{1-4}$ haloalkyl, $C_{1-4}$ alkoxy, halo, CN, $NO_2$, $NH_2$, OH, —COOH, —$CONH_2$, C(O)$C_{1-4}$ alkyl, C(O)N($C_{1-4}$ alkyl)$_2$, and 5-6 membered heterocycloalkyl;

or, alternatively, $R^{N2}$ and $R^1$, together with the atoms to which they are attached, come together to form a 5-6 membered heterocycloalkyl group;

or, alternatively, $R^{N2}$ and $L^1$ or $X^2$ come together to form a 5-6 membered heterocycloalkyl group; and each $R^2$ is independently selected from the group consisting of $C_{1-4}$ alkyl, halo, CN, $NH_2$, —COOH, —CONH$_2$, —C(O)C$_{1-4}$ haloalkyl, —NHC(O)C$_{1-4}$ haloalkyl, —NHSO$_2$—C$_{1-4}$ alkyl, and phenoxy.

In some embodiments, if $L^1$ is cyclopropylene then at least one $R^1$ group is CN.

In some embodiments, the compound of Formula II is not a compound selected from the group consisting of:

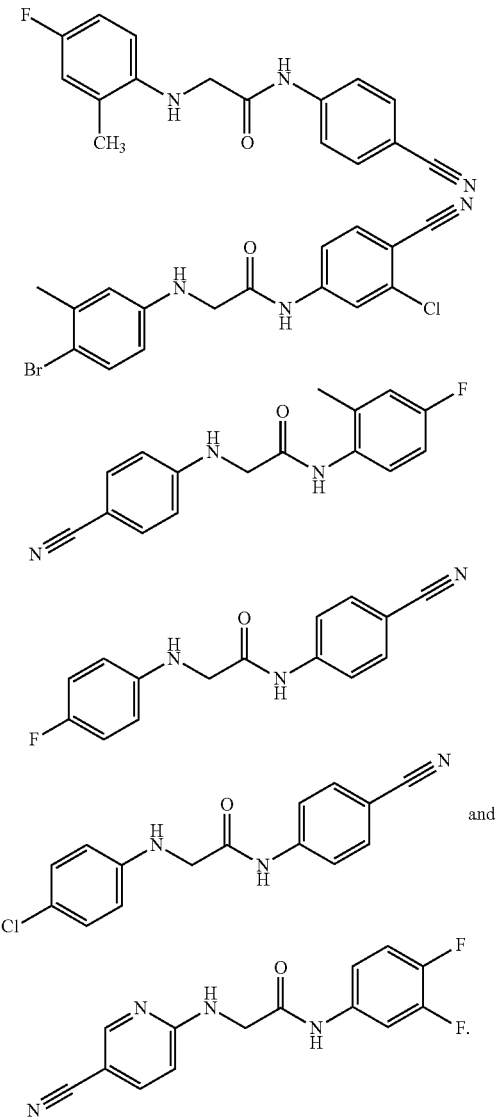

and

In Some Embodiments:

Z is selected from the group consisting of O and S;

L is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of O, NR$^{N1}$, C(O), C(S), (C$_{1-4}$alkylene)-C(O), NR$^{N1}$C(O), NR$^{N1}$C(S), and NR$^{N1}$SO$_2$;

or, alternatively, $L^2$ is absent;

$R^{N1}$ and $R^{N2}$ are each independently selected from the group consisting of H and $C_{1-4}$ alkyl;

$R^{N3}$ is selected from the group consisting of $C_{1-4}$ haloalkyl, NH($C_{1-4}$ alkyl), cyclopropyl, phenyl, and pyridyl, wherein the phenyl and pyridyl are optionally substituted by 1, 2, or 3 $R^1$ groups;

each $R^1$ is independently selected from the group consisting of H, $C_{1-4}$ alkyl, $C_{1-4}$ haloalkyl, $C_{1-4}$ alkoxy, halo, CN, $NO_2$, $NH_2$, OH, C(O)$C_{1-4}$ alkyl, C(O)N($C_{1-4}$ alkyl)$_2$, and 5-6 membered heterocycloalkyl;

or, alternatively, $R^{N2}$ and $R^1$, together with the atoms to which they are attached, come together to form a 5-6 membered heterocycloalkyl group;

or, alternatively, $R^{N2}$ and $L^1$ come together to form a 5-6 membered heterocycloalkyl group; and each $R^2$ is independently selected from the group consisting of $C_{1-4}$ alkyl, halo, CN, $NH_2$, —C(O)$C_{1-4}$ haloalkyl, —NHC(O)$C_{1-4}$ haloalkyl, —NHSO$_2$—$C_{1-4}$ alkyl, and phenoxy.

In some embodiments of Formula II, $L^1$ is selected from the group consisting of methylene, ethylene, ethen-1,2-diyl, fluoromethylene, cyclopropylene, and hydroxypropylene.

In some embodiments, the compound of Formula II is a compound of Formula I:

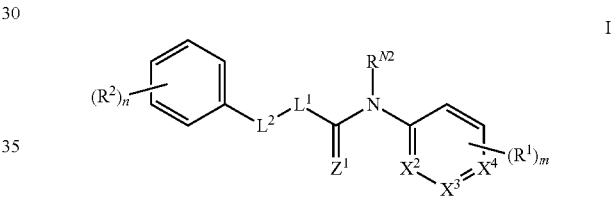

I or a pharmaceutically acceptable salt thereof, wherein:

$Z^1$ is selected from the group consisting of O and S;

$L^1$ is selected from the group consisting of methylene, ethylene, ethen-1,2-diyl, fluoromethylene, difluoromethylene, aminomethylene, cyclopropylene, and hydroxypropylene, wherein the ethylene is optionally substituted by trifluoromethyl;

$L^2$ is selected from the group consisting of C(O), C(S), (C$_{1-4}$ alkylene)-C(O), NR$^{N1}$C(O), NR$^{N1}$C(S), and NR$^{N1}$SO$_2$;

or, alternatively, $L^2$ is absent;

$R^{N1}$ and $R^{N2}$ are each independently selected from the group consisting of H and $C_{1-4}$ alkyl;

$X^2$, $X^3$, and $X^4$ are each independently selected from the group consisting of C and N;

each $R^1$ is independently selected from the group consisting of H, $C_{1-4}$ alkyl, $C_{1-4}$ haloalkyl, halo, CN, $NO_2$, $NH_2$, —COOH, —CONH$_2$ and OH;

or, alternatively, $R^{N2}$ and $R^1$, together with the atoms to which they are attached, come together to form a 5-6 membered heterocycloalkyl group;

or, alternatively, $R^{N2}$ and $L^1$ or $X^2$ come together to form a 5-6 membered heterocycloalkyl group;

each $R^2$ is independently selected from the group consisting of $C_{1-4}$ alkyl, halo, CN, $NH_2$, —COOH, —CONH$_2$, —C(O)$C_{1-4}$ haloalkyl, —NHC(O)$C_{1-4}$ haloalkyl, —NHSO$_2$—$C_{1-4}$ alkyl, and phenoxy;

m is 1, 2, or 3; and n is 1, 2, or 3.

In some embodiments of Formula I, L¹ is selected from the group consisting of methylene, ethylene, ethen-1,2-diyl, fluoromethylene, cyclopropylene, and hydroxypropylene.

In some embodiments, if L is cyclopropylene then at least one R¹ group is CN.

In some embodiments, the compound of Formula I is not a compound selected from the group consisting of:

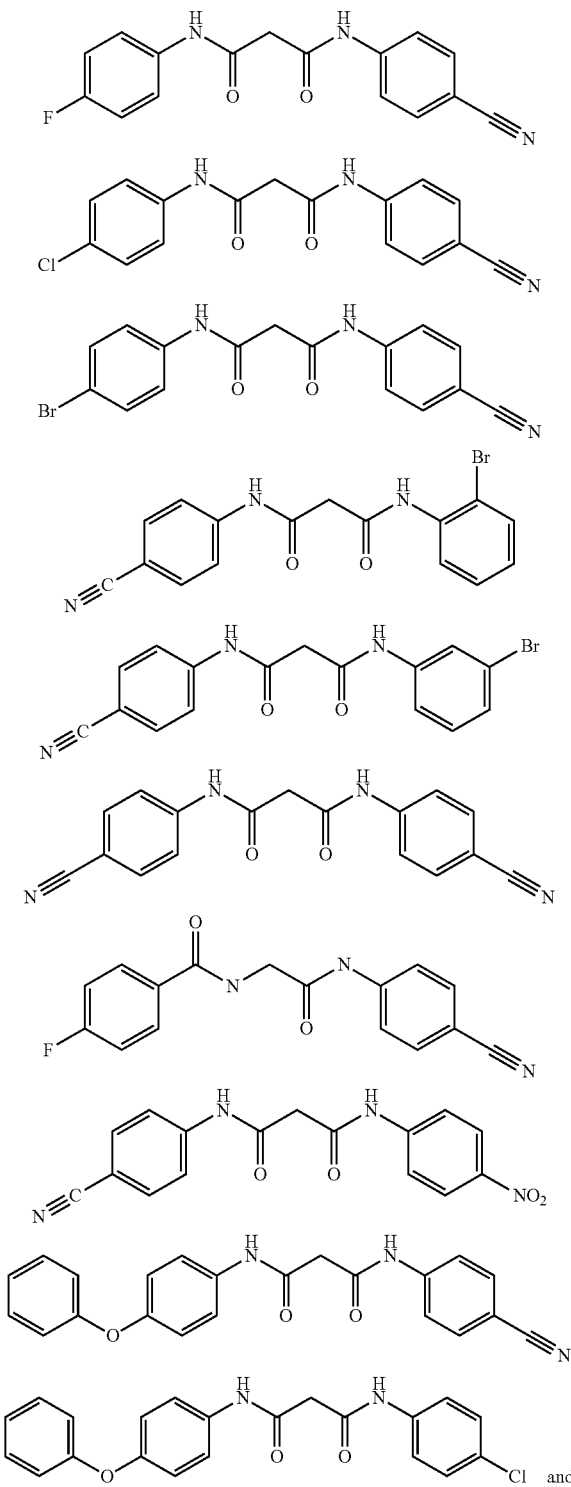

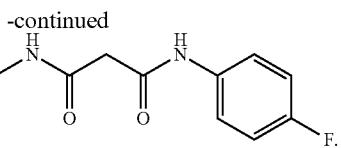

In Some Embodiments:

$Z^1$ is selected from the group consisting of O and S;

$L^1$ is selected from the group consisting of methylene, ethylene, ethen-1,2-diyl, fluoromethylene, cyclopropylene, and hydroxypropylene;

$L^2$ is selected from the group consisting of C(O), C(S), ($C_{1-4}$ alkylene)-C(O), $NR^{N1}C(O)$, $NR^{N1}C(S)$, and $NR^{N1}SO_2$;

or, alternatively, $L^2$ is absent;

$R^{N1}$ and $R^{N2}$ are each independently selected from the group consisting of H and $C_{1-4}$ alkyl;

$X^2$, $X^3$, and $X^4$ are each independently selected from the group consisting of C and N;

each $R^1$ is independently selected from the group consisting of H, $C_{1-4}$ alkyl, $C_{1-4}$ haloalkyl, halo, CN, $NO_2$, $NH_2$, and OH;

or, alternatively, $R^{N2}$ and $R^1$, together with the atoms to which they are attached, come together to form a 5-6 membered heterocycloalkyl group;

or, alternatively, $R^{N2}$ and $L^1$ come together to form a 5-6 membered heterocycloalkyl group;

each $R^2$ is independently selected from the group consisting of $C_{1-4}$ alkyl, halo, CN, $NH_2$, —C(O)$C_{1-4}$ haloalkyl, —NHC(O)$C_{1-4}$ haloalkyl, —NHSO$_2$—$C_{1-4}$ alkyl, and phenoxy;

m is 1, 2, or 3; and n is 1, 2, or 3.

In some embodiments, $Z^1$ is O. In some embodiments, $Z^1$ is S.

In some embodiments, $L^1$ is selected from the group consisting of methylene, ethylene, ethen-1,2-diyl, fluoromethylene, difluoromethylene, aminomethylene, and hydroxypropylene, wherein the ethylene is optionally substituted by trifluoromethyl. In some embodiments, $L^1$ is selected from the group consisting of methylene, ethylene, ethen-1,2-diyl, fluoromethylene, and hydroxypropylene. In some embodiments, $L^1$ is methylene. In some embodiments, $L^1$ is ethylene. In some embodiments, $L^1$ is ethen-1,2-diyl. In some embodiments, $L^1$ is fluoromethylene. In some embodiments, $L^1$ is cyclopropylene. In some embodiments, $L^1$ is hydroxypropylene. In some embodiments, $L^1$ is ethylene which is is optionally substituted by trifluoromethyl.

In some embodiments, $L^2$ is absent. In some embodiments, $L^2$ is selected from the group consisting of C(O), C(S), ($C_{1-4}$ alkylene)-C(O), $NR^{N1}C(O)$, $NR^{N1}C(S)$, and $NR^{N1}SO_2$. In some embodiments, $L^2$ is selected from the group consisting of C(O), $NR^{N1}C(O)$, $NR^{N1}C(S)$, and $NR^{N1}SO_2$. In some embodiments, $L^2$ is selected from the group consisting of C(O), $NR^{N1}C(O)$, $NR^{N1}C(S)$, and $NR^{N1}SO_2$. In some embodiments, $L^2$ is selected from the group consisting of C(O), NHC(O), NHC(S), and NHSO$_2$. In some embodiments, $L^2$ is NHC(O).

In some embodiments, $R^{N1}$ is selected from the group consisting of H and methyl. In some embodiments, $R^{N1}$ is H. In some embodiments, $R^{N1}$ is methyl.

In some embodiments, $R^{N2}$ is selected from the group consisting of H and methyl. In some embodiments, $R^{N2}$ is H. In some embodiments, $R^{N2}$ is methyl.

In some embodiments, $R^{N2}$ and $L^1$, together with the atoms to which they are attached, come together to form a 5-6 membered heterocycloalkyl group. In some embodiments, $R^{N2}$ and $L^1$, together with the atoms to which they are attached, come together to form a pyrrolidinone group.

In some embodiments, $X^2$ is $C(R^1)$. In some embodiments, $X^2$ is N.

In some embodiments, $X^3$ is $C(R^1)$. In some embodiments, $X^3$ is N.

In some embodiments, $X^4$ is $C(R^1)$. In some embodiments, $X^4$ is N.

In some embodiments, one of $X^2$, $X^3$, and $X^4$ is N and the other two variables are C. In some embodiments, one of $X^2$, $X^3$, and $X^4$ is $C(R^1)$ and the other two variables are N.

In some embodiments, $X^2$ and $X^4$ are each $C(R^1)$. In some embodiments, $X^2$ and $X^4$ are each N. In some embodiments, $X^2$ and $X^3$ are each $C(R^1)$. In some embodiments, $X^2$ and $X^3$ are each N. In some embodiments, $X^3$ and $X^4$ are each $C(R^1)$. In some embodiments, $X^3$ and $X^4$ are each N.

In some embodiments, $X^2$, $X^3$, and $X^4$ are each $C(R^1)$. In some embodiments, $X^2$, $X^3$, and $X^4$ are each N.

In some embodiments, each $R^1$ is independently selected from the group consisting of H, methyl, trifluoromethyl, halo (e.g., fluoro, chloro, bromo, iodo), CN, $NO_2$, $NH_2$, and OH. In some embodiments, each $R^1$ is selected from the group consisting of H and CN. In some embodiments, each $R^1$ is selected from the group consisting of H, halo, trifluoromethyl, and CN. In some embodiments, each $R^1$ is selected from the group consisting of H, halo, and CN. In some embodiments, each $R^1$ is selected from the group consisting of H, chloro, trifluoromethyl, and CN. In some embodiments, each $R^1$ is selected from the group consisting of H, chloro, and CN. In some embodiments, each $R^1$ is CN. In some embodiments, two $R^1$ groups are H and one $R^1$ group is selected from the group consisting of halo, trifluoromethyl, and CN. In some embodiments, one $R^1$ group is H and two $R^1$ groups are independently selected from the group consisting of halo, trifluoromethyl, and CN.

In some embodiments, each $R^2$ is independently selected from the group consisting of $C_{1-4}$ alkyl, fluoro, iodo, CN, $NH_2$, —COOH, —$CONH_2$, —$C(O)C_{1-4}$ haloalkyl, —NHC(O)$C_{1-4}$ haloalkyl, —$NHSO_2$—$C_{1-4}$ alkyl, and phenoxy. In some embodiments, each $R^2$ is independently selected from the group consisting of methyl, fluoro, iodo, CN, $NH_2$, —COOH, —$CONH_2$, —$C(O)CF_3$, —$NHC(O)CF_3$, —$NHSO_2CH_2CH_3$, and phenoxy. In some embodiments, each $R^2$ is independently selected from the group consisting of methyl, fluoro, iodo, CN, $NH_2$, —$C(O)CF_3$, —$NHC(O)CF_3$, —$NHSO_2CH_2CH_3$, and phenoxy. In some embodiments, each $R^2$ is selected from the group consisting of halo, CN, and phenoxy. In some embodiments, each $R^2$ is selected from the group consisting of bromo, chloro, CN, and phenoxy. In some embodiments, each $R^2$ is selected from the group consisting of bromo, chloro, fluoro, CN, and phenoxy.

In some embodiments, m is 1. In some embodiments, m is 2. In some embodiments, m is 3.

In some embodiments, n is 1. In some embodiments, n is 2. In some embodiments, n is 3.

In some embodiments, m is 1 and n is 1. In some embodiments, m is 1 and n is 2. In some embodiments, m is 1 and n is 3. In some embodiments, m is 2 and n is 1. In some embodiments, m is 2 and n is 2. In some embodiments, m is 2 and n is 3. In some embodiments, m is 3 and n is 1. In some embodiments, m is 3 and n is 2. In some embodiments, m is 3 and n is 3.

In Some Embodiments:

$Z^1$ is selected from the group consisting of O and S;

$L^1$ is selected from the group consisting of methylene, ethylene, ethen-1,2-diyl, fluoromethylene, cyclopropylene, and hydroxypropylene;

$L^2$ is selected from the group consisting of C(O), $NR^{N1}$C(O), $NR^{N1}$C(S), and $NR^{N1}SO_2$;

or, alternatively, $L^2$ is absent;

$R^{N1}$ is selected from the group consisting of H and methyl;

$R^{N2}$ is selected from the group consisting of H and methyl;

$X^2$, $X^3$, and $X^4$ are each independently selected from the group consisting of C and N;

each $R^1$ is independently selected from the group consisting of H, methyl, trifluoromethyl, halo, CN, $NO_2$, $NH_2$, and OH;

each $R^2$ is independently selected from the group consisting of methyl, fluoro, iodo, CN, $NH_2$, —$C(O)CF_3$, —NHC(O)$CF_3$, —$NHSO_2CH_2CH_3$, and phenoxy;

m is 1 or 2; and n is 1 or 2.

In Some Embodiments:

$Z^1$ is O;

$L^1$ is selected from the group consisting of methylene, ethylene, ethen-1,2-diyl, fluoromethylene, cyclopropylene, and hydroxypropylene;

$L^2$ is $NR^{N1}C(O)$;

or, alternatively, $L^2$ is absent;

$R^{N1}$ is selected from the group consisting of H and methyl;

$R^{N2}$ is selected from the group consisting of H and methyl;

$X^2$, $X^3$, and $X^4$ are each independently selected from the group consisting of C and N;

each $R^1$ is independently selected from the group consisting of H, methyl, trifluoromethyl, halo, CN, $NO_2$, $NH_2$, and OH;

each $R^2$ is independently selected from the group consisting of methyl, fluoro, iodo, CN, $NH_2$, —$C(O)CF_3$, —NHC(O)$CF_3$, —$NHSO_2CH_2CH_3$, and phenoxy;

m is 1 or 2; and n is 1 or 2.

In some embodiments:

$Z^1$ is selected from the group consisting of O and S;

$L^1$ is selected from the group consisting of methylene, ethylene, ethen-1,2-diyl, fluoromethylene, cyclopropylene, and hydroxypropylene;

$L^2$ is selected from the group consisting of O, $NR^{N1}$, C(O), $NR^{N1}$C(O) $NR^{N1}$C(S), and $NR^{N1}SO_2$;

or, alternatively, $L^2$ is absent;

$R^{N1}$ is selected from the group consisting of H and methyl;

$R^{N2}$ is selected from the group consisting of H and methyl;

$R^{N3}$ is selected from the group consisting of phenyl and pyridyl, wherein the phenyl and pyridyl are each optionally substituted by 1, 2, or 3 independently selected $R^1$ groups;

each $R^1$ is independently selected from the group consisting of H, methyl, trifluoromethyl, methoxy, halo, CN, $NO_2$, $NH_2$, OH, $C(O)CH_3$, $C(O)N(CH_3)_2$, morpholinyl, and pyrrolidinone; and each $R^2$ is independently selected from the group consisting of methyl, fluoro, iodo, CN, $NH_2$, —$C(O)CF_3$, —NHC(O)$CF_3$, —$NHSO_2CH_2CH_3$, and phenoxy.

In Some Embodiments:

$Z^1$ is O;

$L^1$ is selected from the group consisting of methylene, ethylene, ethen-1,2-diyl, fluoromethylene, cyclopropylene, and hydroxypropylene;

$L^2$ is selected from the group consisting of $NR^{N1}$ and $NR^{N1}C(O)$;

or, alternatively, $L^2$ is absent;

$R^{N1}$ is selected from the group consisting of H and methyl;

$R^{N2}$ is selected from the group consisting of H and methyl;

$R^{N3}$ is selected from the group consisting of phenyl and pyridyl, wherein the phenyl and pyridyl are each optionally substituted by 1, 2, or 3 independently selected $R^1$ groups;

each $R^1$ is independently selected from the group consisting of H, methyl, trifluoromethyl, methoxy, halo, CN, $NO_2$, $NH_2$, OH, $C(O)CH_3$, $C(O)N(CH_3)_2$, morpholinyl, and pyrrolidinone; and each $R^2$ is independently selected from the group consisting of methyl, fluoro, iodo, CN, $NH_2$, —$C(O)CF_3$, —$NHC(O)CF_3$, —$NHSO_2CH_2CH_3$, and phenoxy.

In some embodiments, the compound of Formula II is a compound of Formula II-a, II-b, II-c, II-d, II-e, II-f, or II-g:

II-a
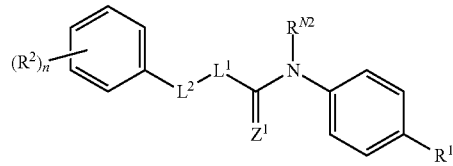

II-b
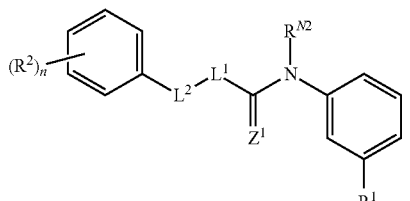

II-c
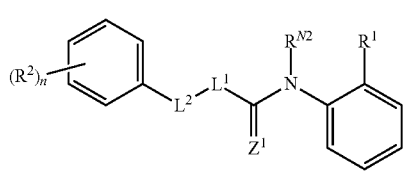

II-d
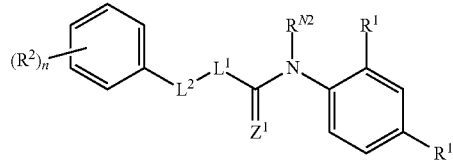

II-e
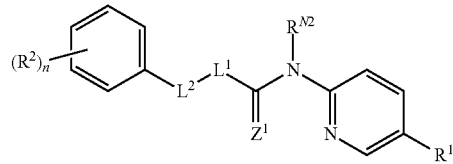

II-f
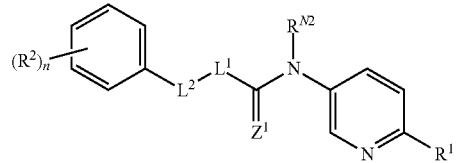

II-g
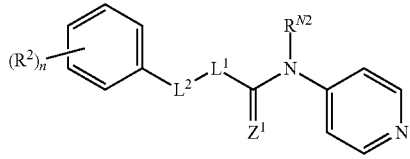

or a pharmaceutically acceptable salt thereof, wherein variables $L^1$, $L^2$, $Z^1$, $R^{N2}$, $R^1$, $R^2$, and n are defined according to the definitions provided herein for compounds of Formula II.

In some embodiments, the compound of Formula II is a compound of Formula II-h, II-i, II-j, II-k, II-l, II-m, II-n, II-o:

II-h
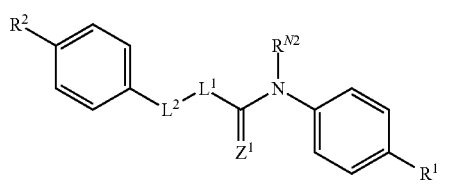

II-i
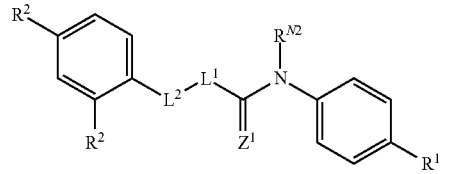

II-j
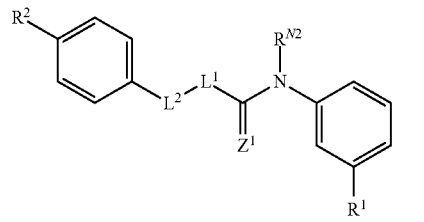

II-k
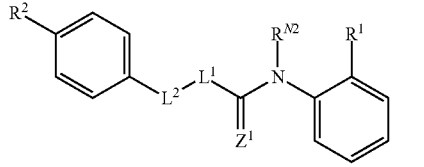

II-l
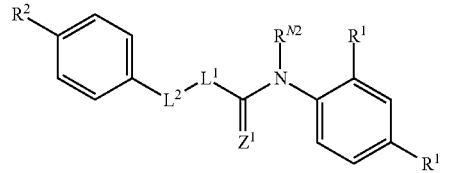

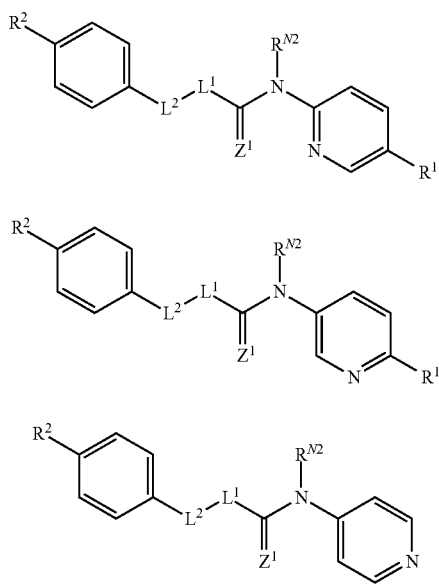

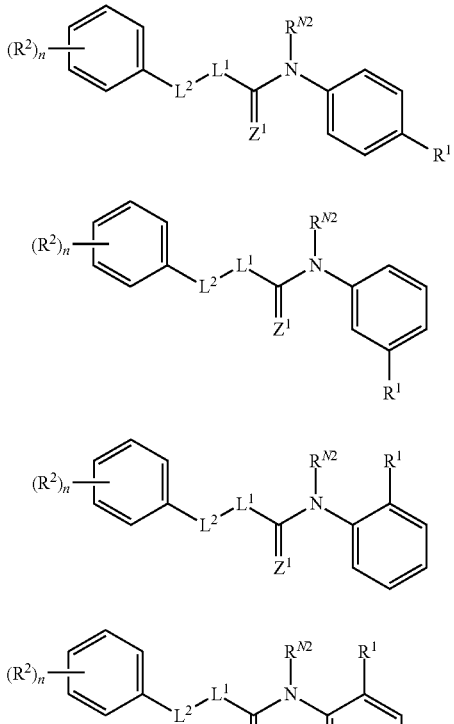

or a pharmaceutically acceptable salt thereof, wherein variables L¹, L², Z¹, R^{N2}, R¹, R², and n are defined according to the definitions provided herein for compounds of Formula II.

In some embodiments, the compound of Formula I is a compound of Formula I-a, I-b, I-c, I-d, I-e, I-f, or I-g:

or a pharmaceutically acceptable salt thereof, wherein variables L¹, L², Z¹, R^{N2}, R¹, R², and n are defined according to the definitions provided herein for compounds of Formula I.

In some embodiments, the compound of Formula I is a compound of Formula I-h, I-i, I-j, I-k, I-l, I-m, I-n, or I-o:

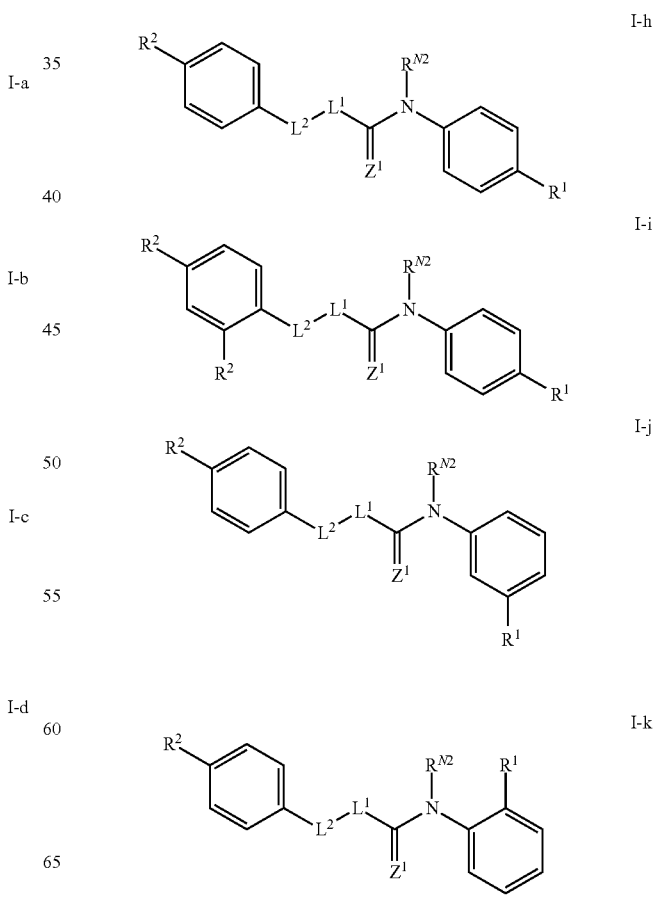

-continued
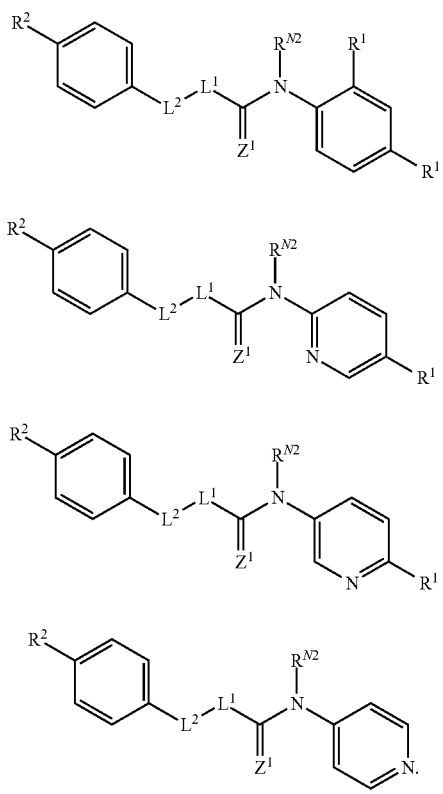
or a pharmaceutically acceptable salt thereof, wherein variables $L^1$, $L^2$, $Z^1$, $R^{N2}$, $R^1$, $R^2$, and n are defined according to the definitions provided herein for compounds of Formula I.
In some embodiments, the compound of Formula II is selected from the group consisting of:
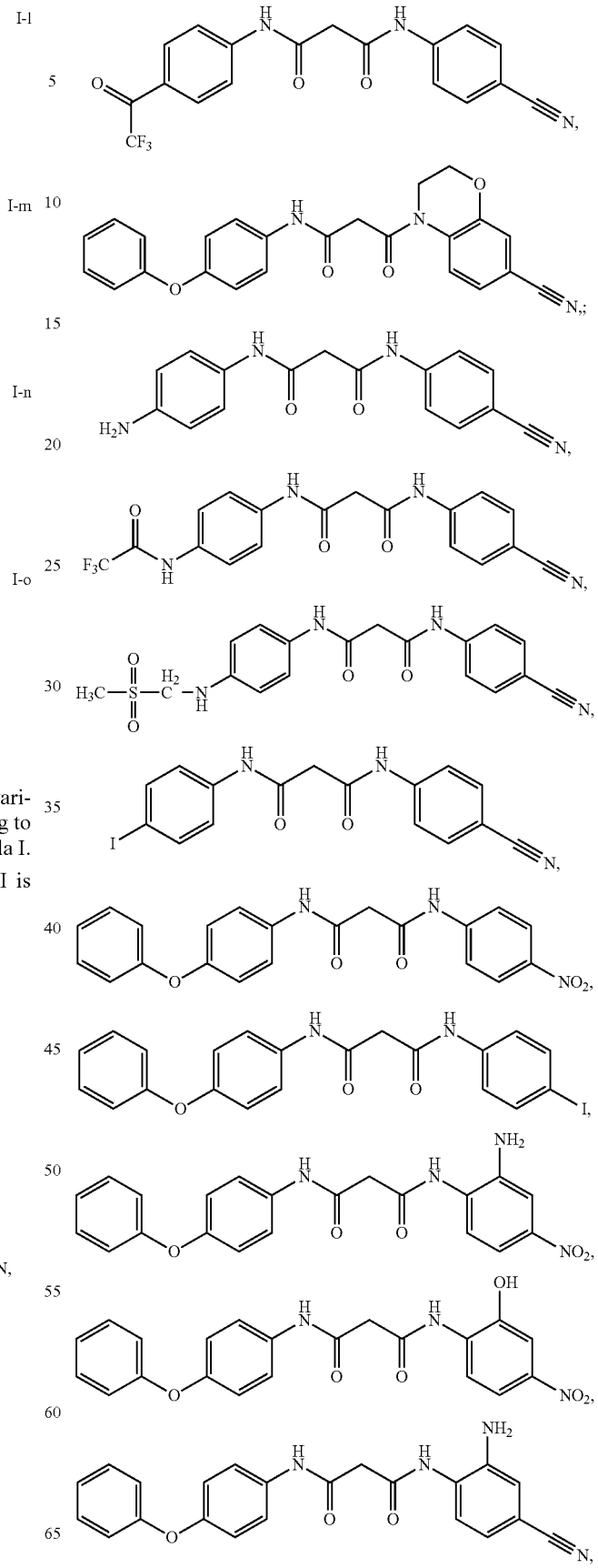

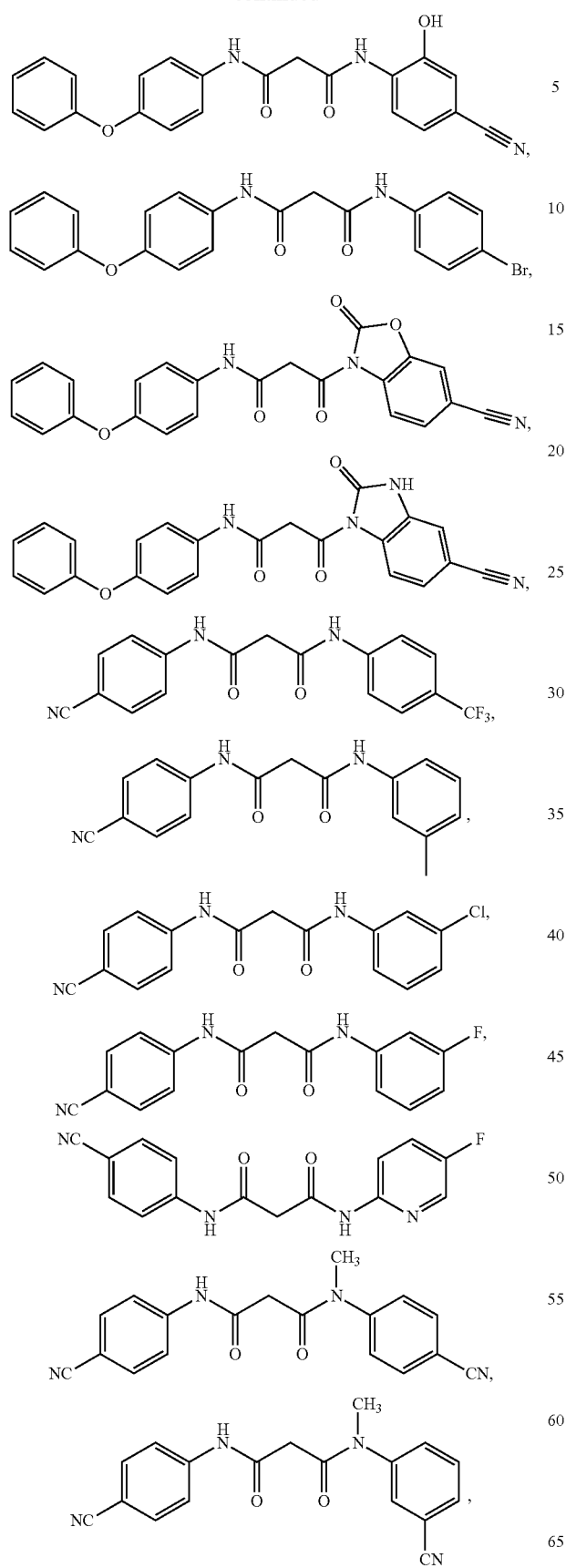
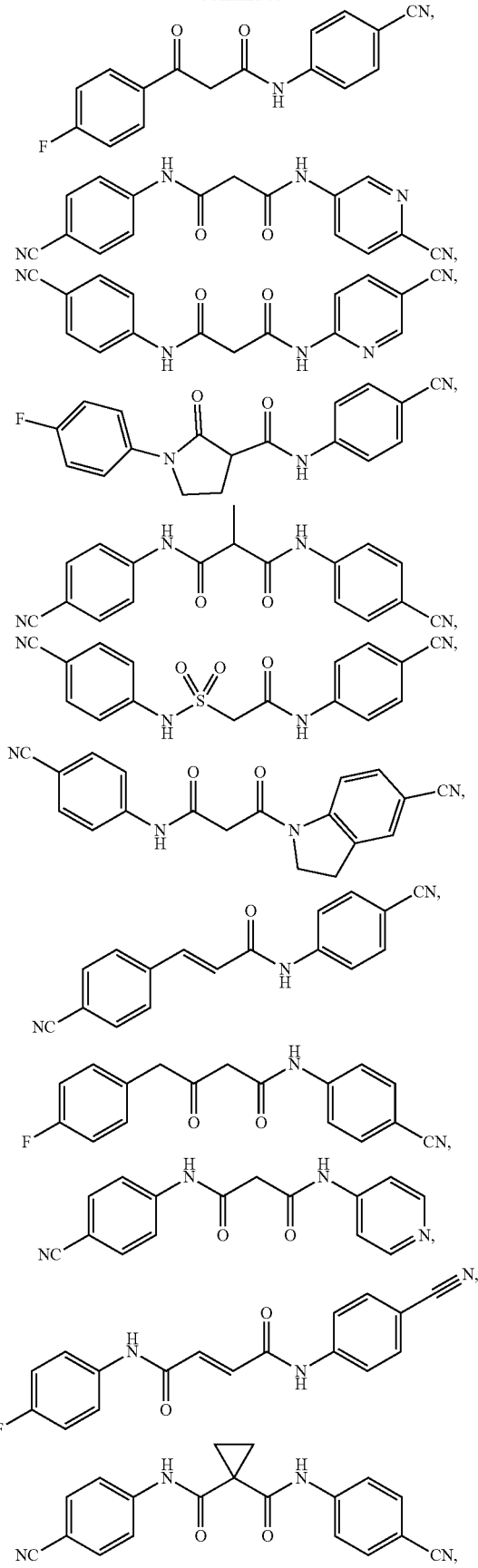

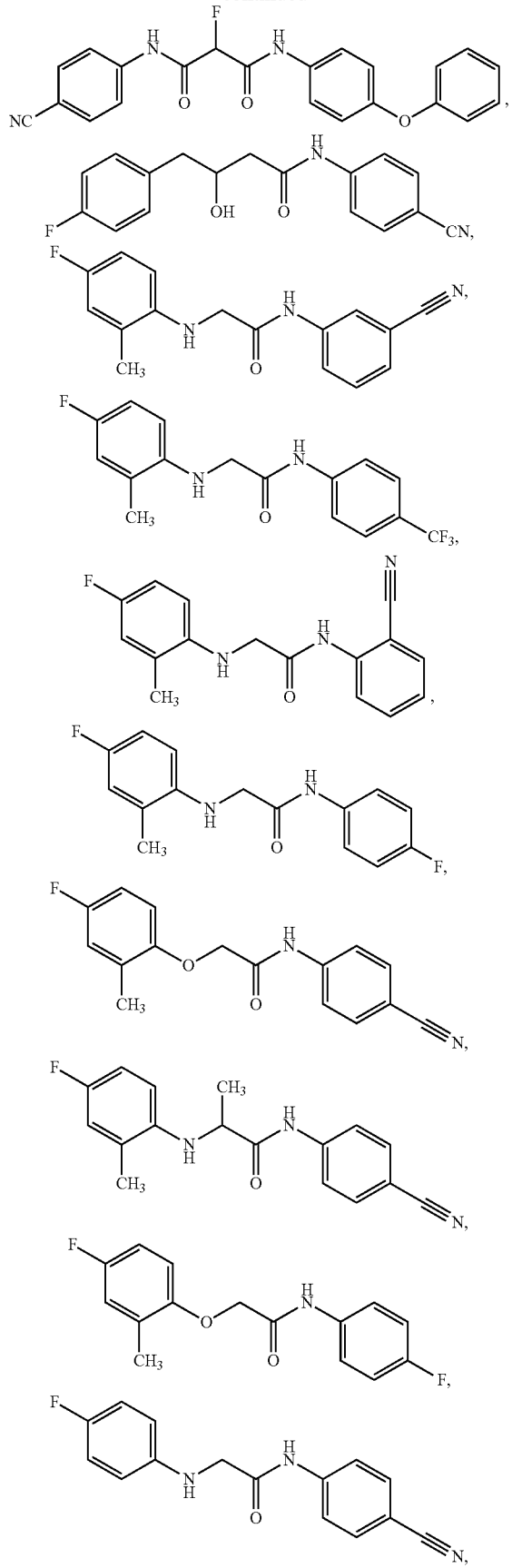
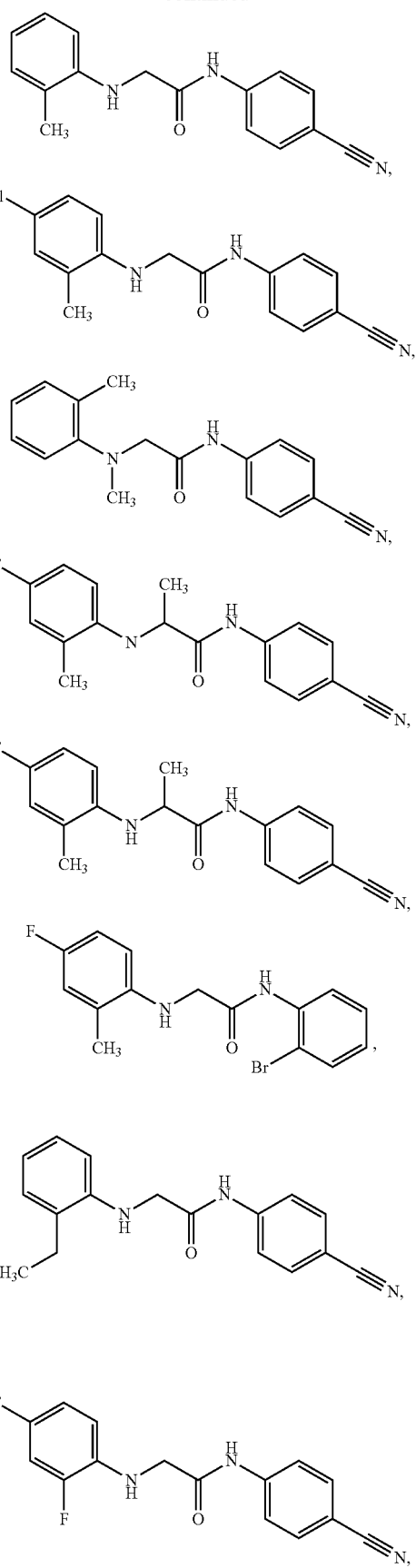

-continued
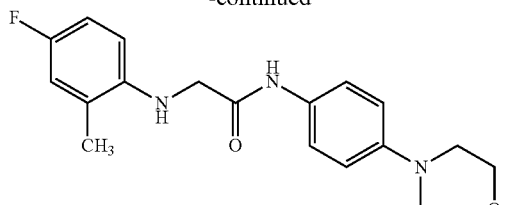
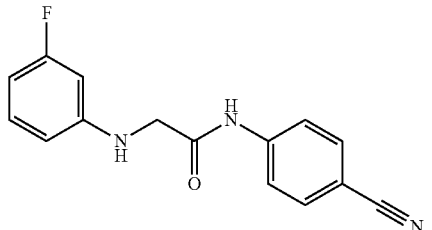
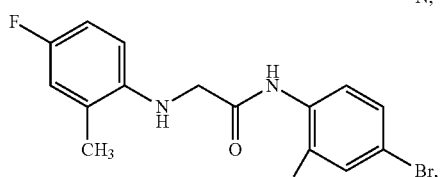
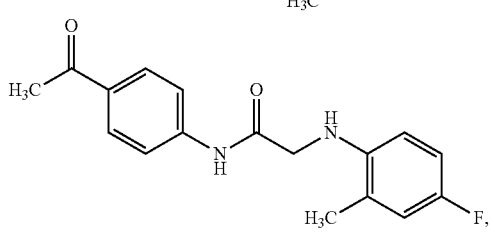
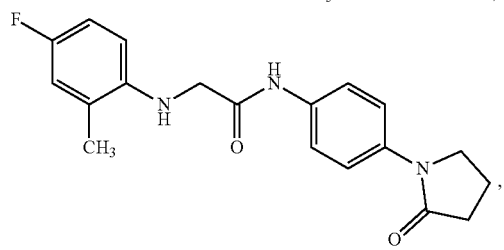
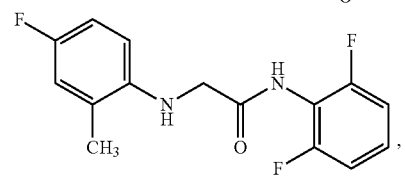
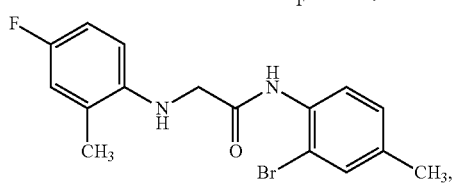
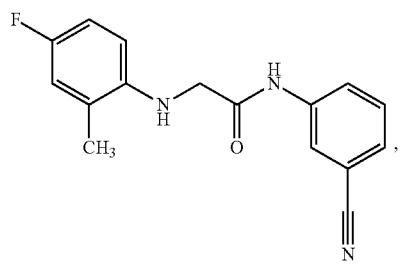
-continued
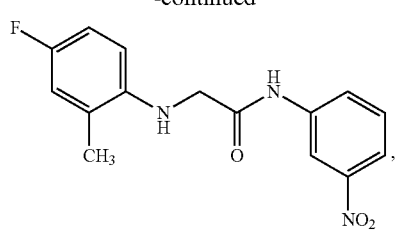
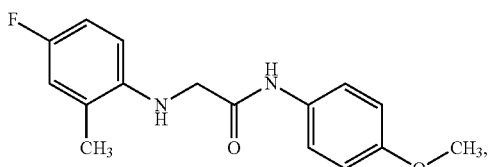
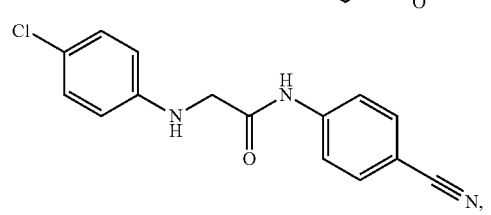
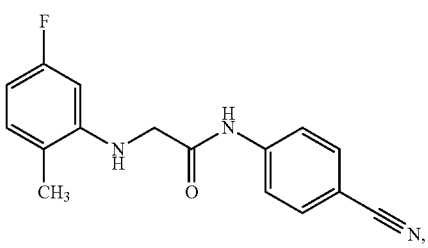
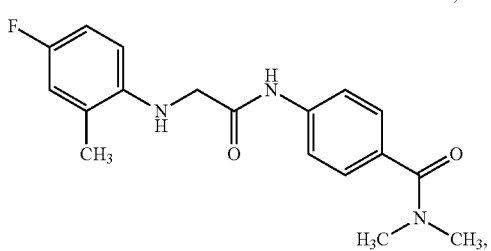
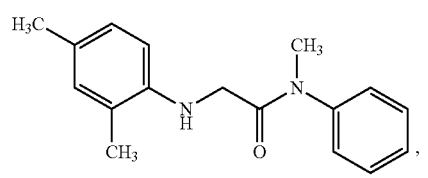
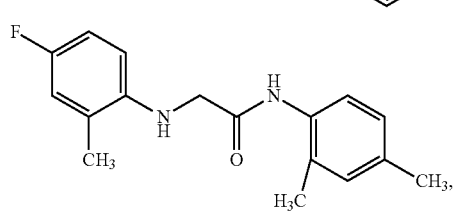
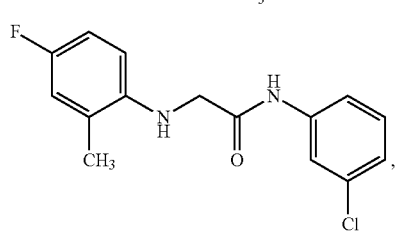

-continued
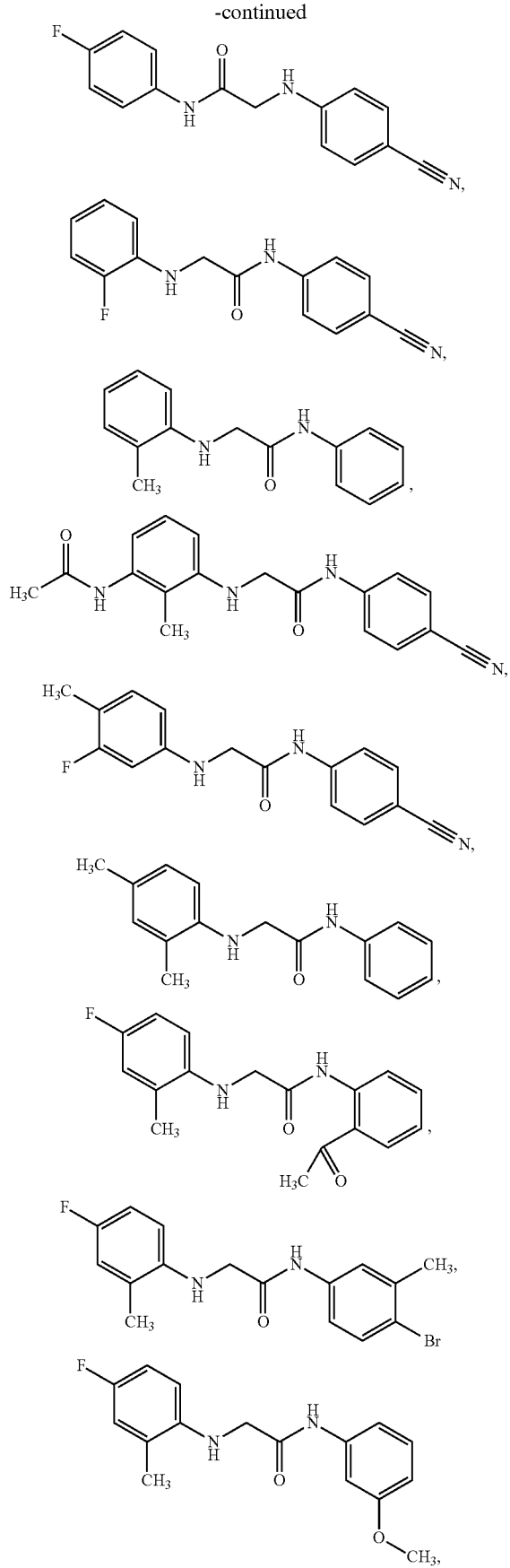
-continued
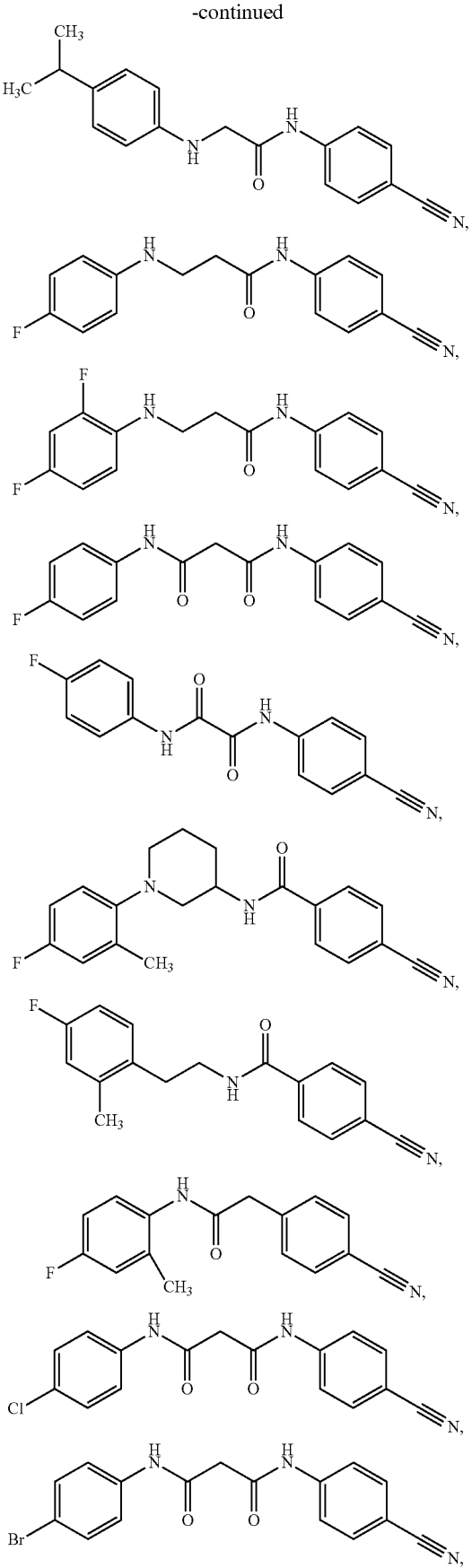

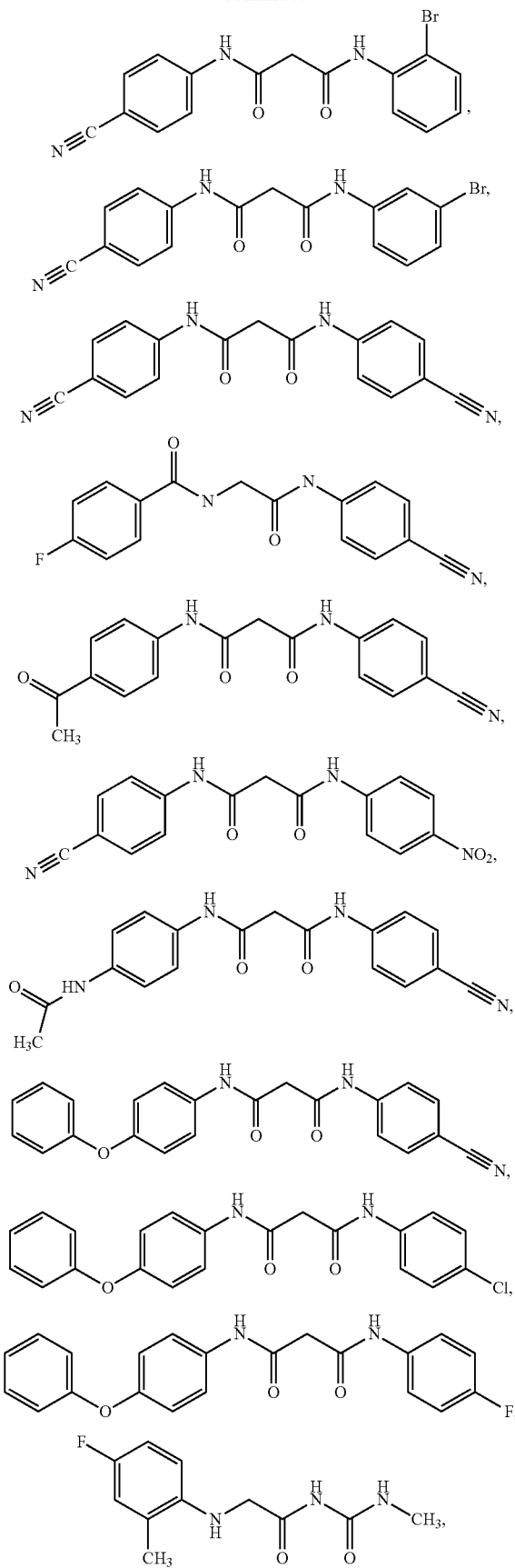
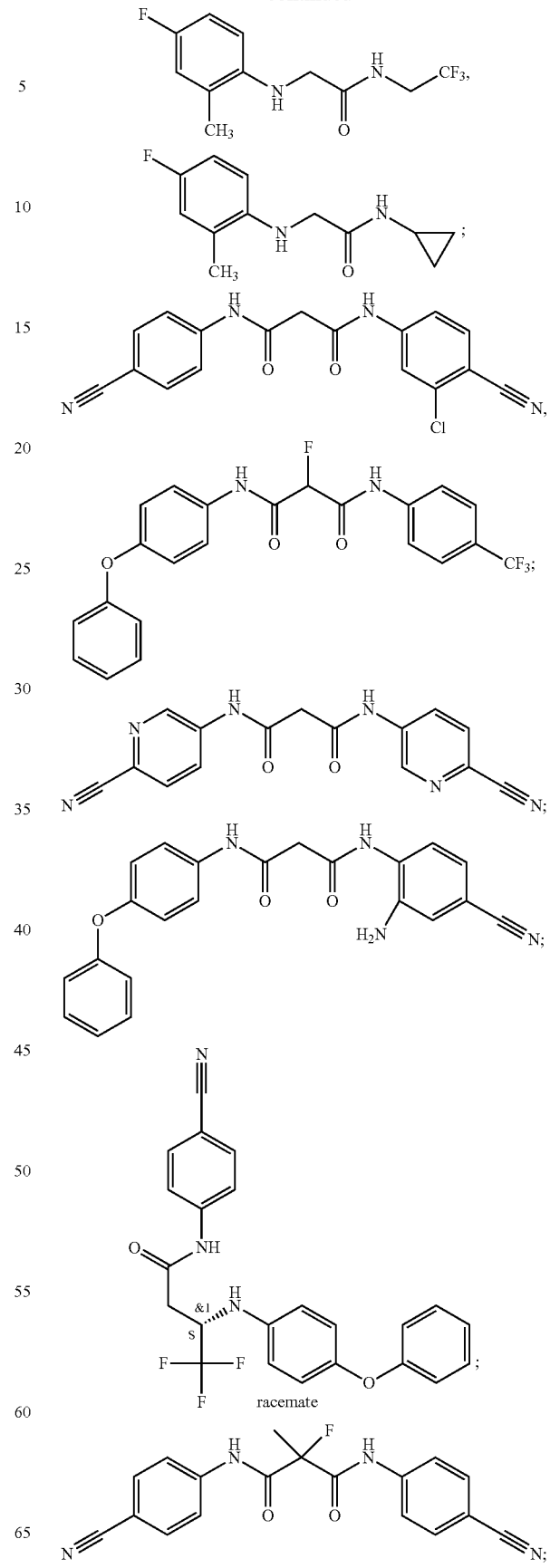

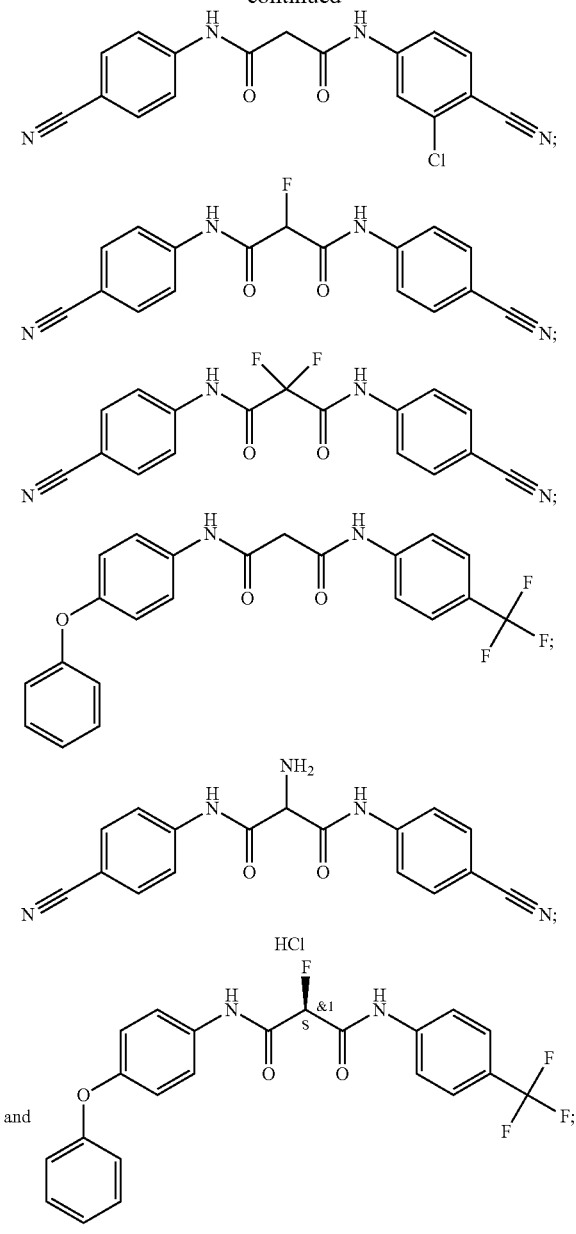
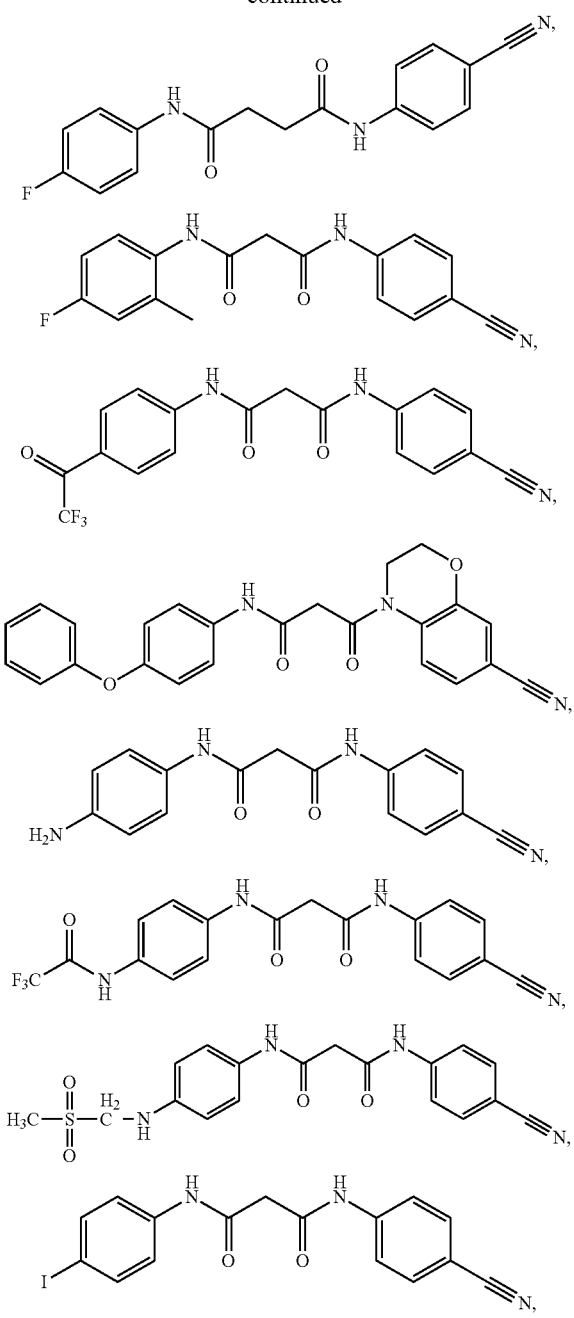
or a pharmaceutically acceptable salt thereof.
In some embodiments, the compound of Formula II or Formula I is selected from the group consisting of:
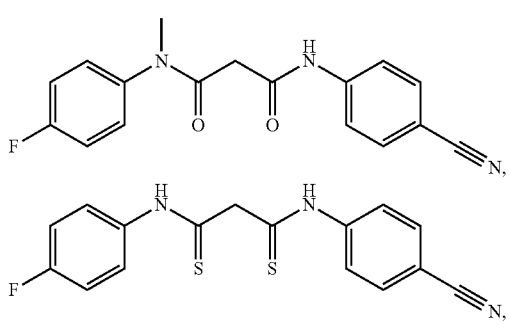
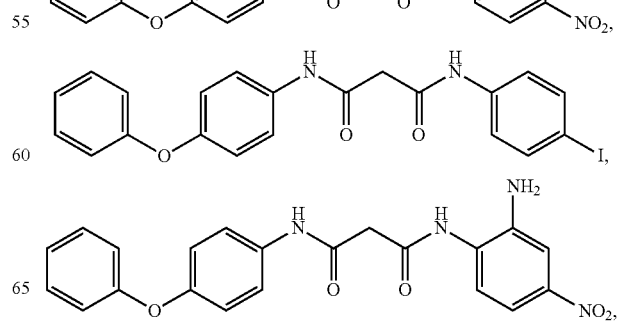

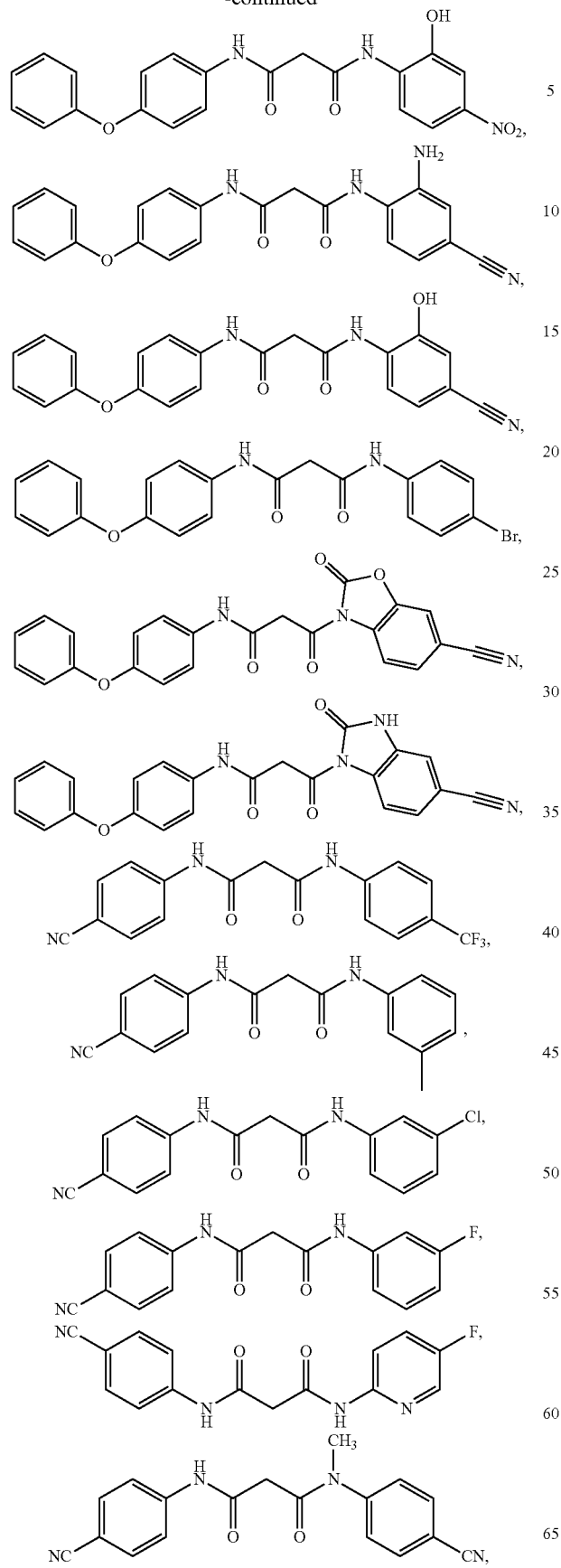
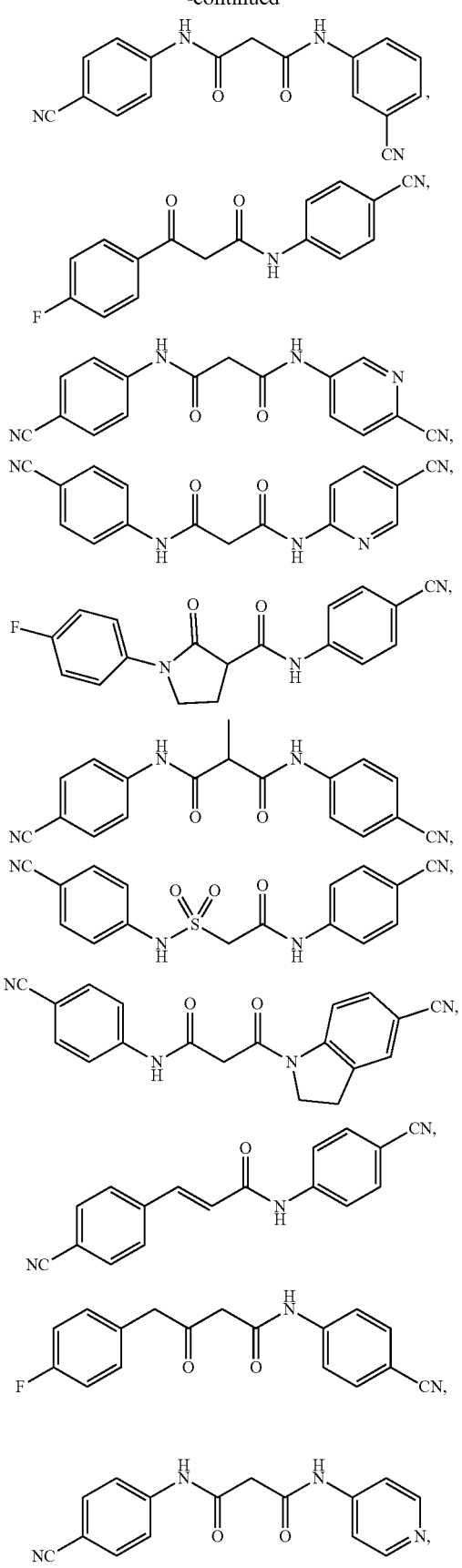

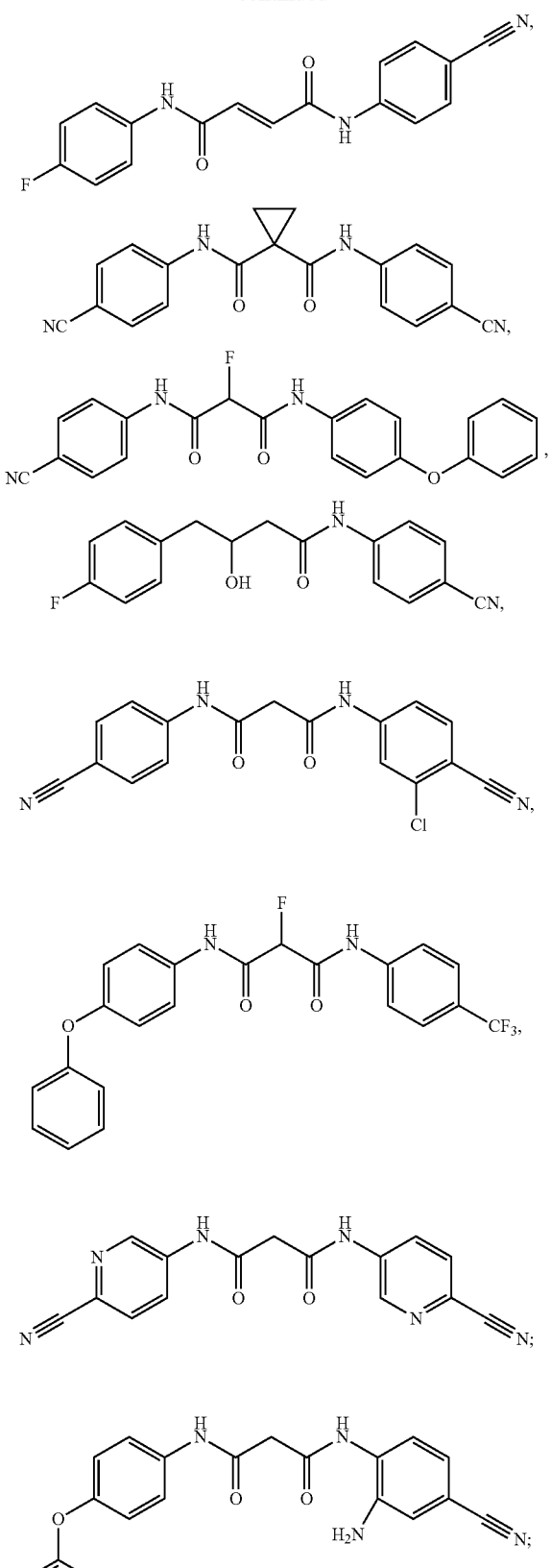
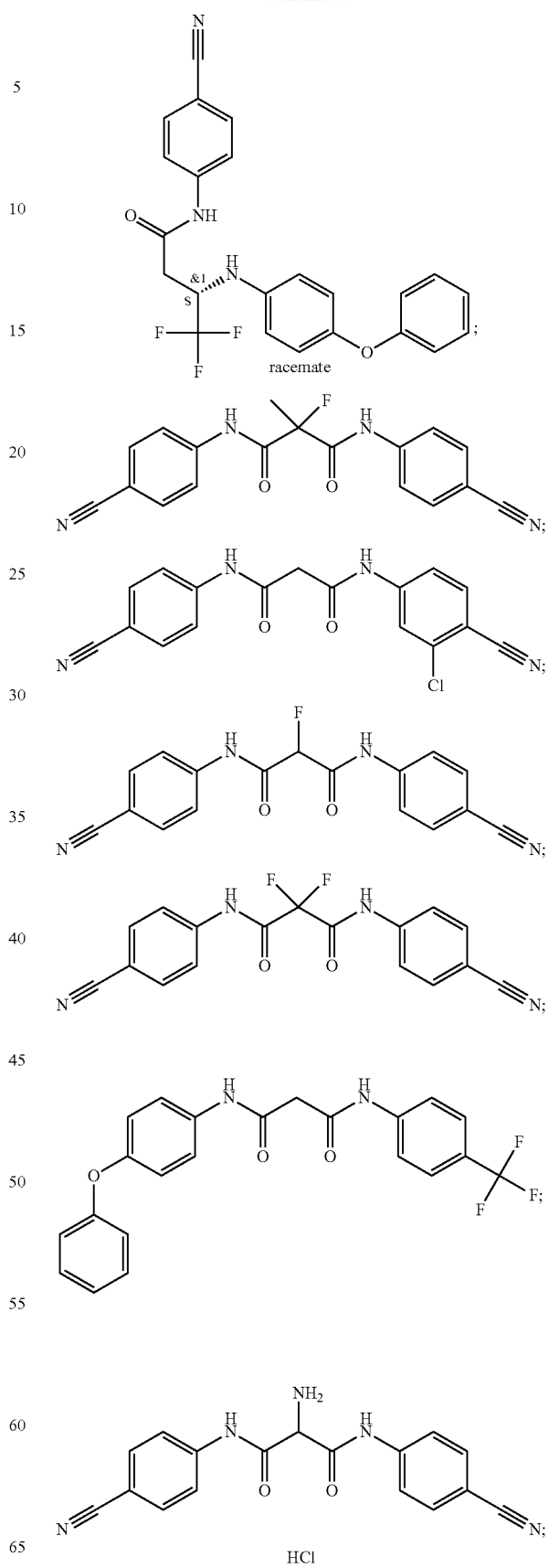

-continued
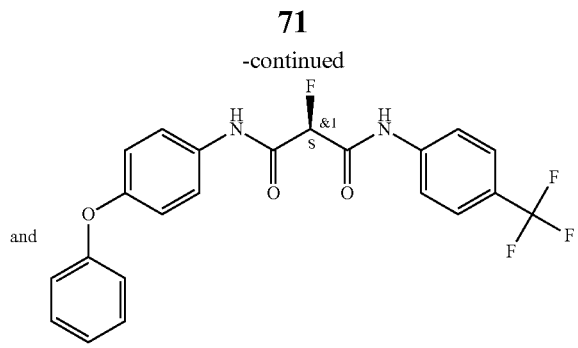
and
or a pharmaceutically acceptable salt thereof.
In some embodiments, the compound of Formula II or Formula I is selected from the group consisting of:
-continued
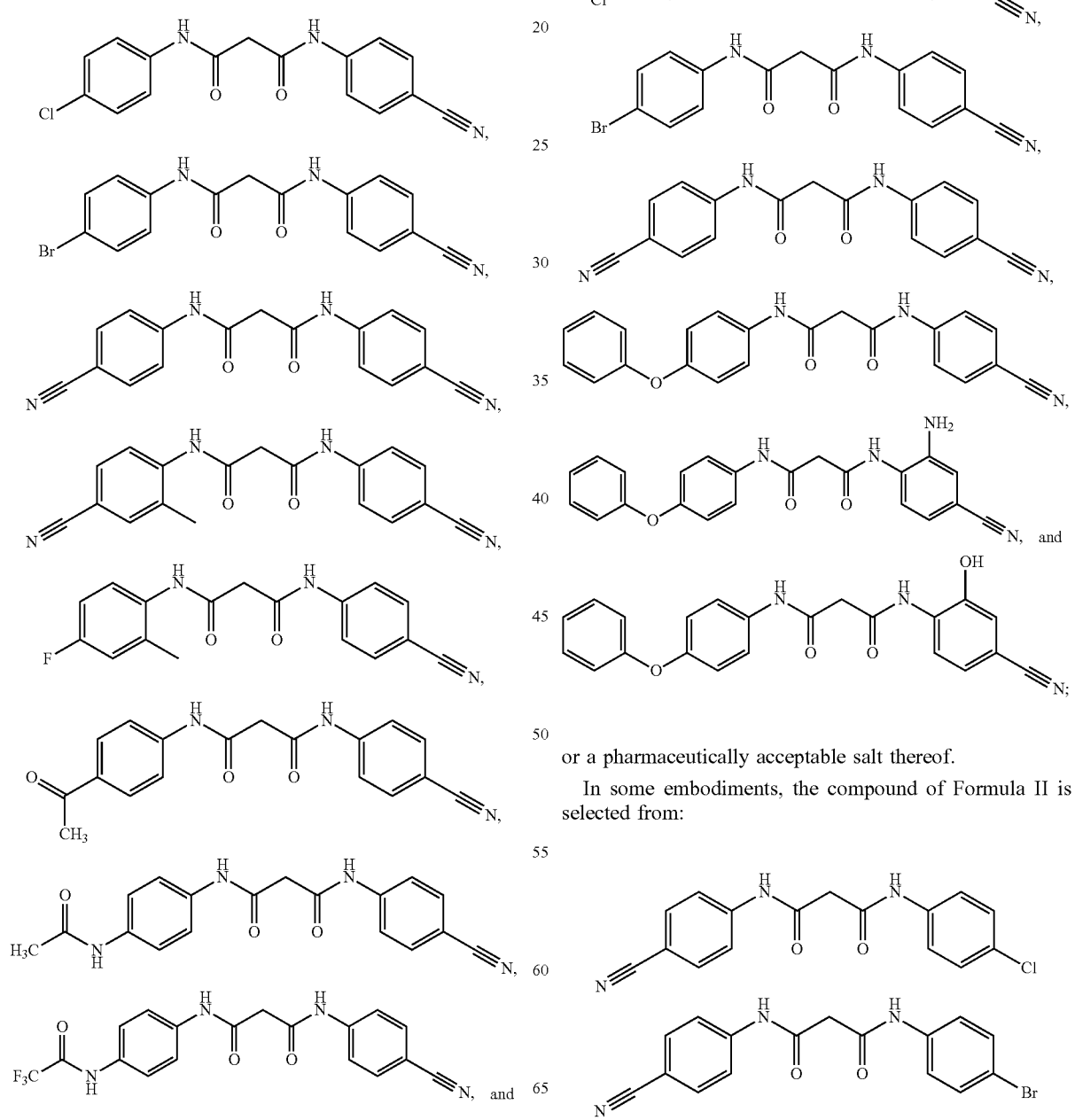
or a pharmaceutically acceptable salt thereof.
In some embodiments, the compound of Formula II is selected from:

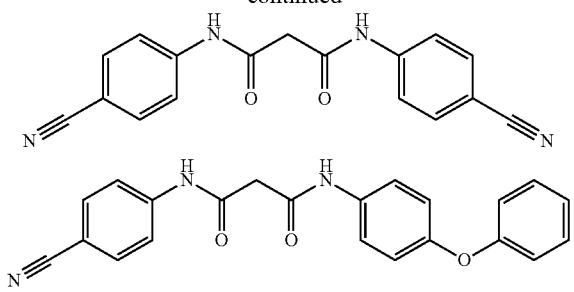
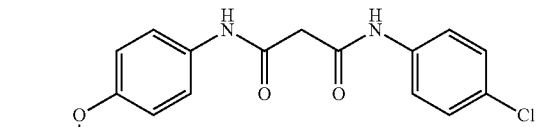
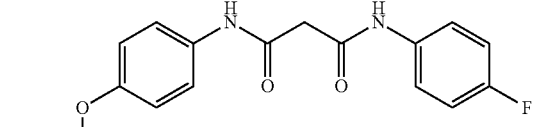
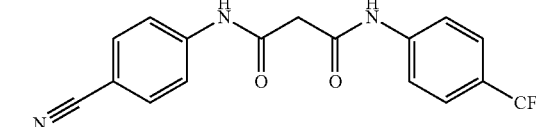
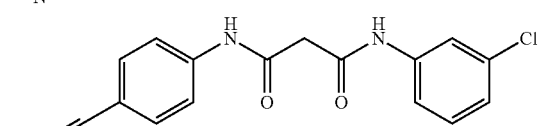
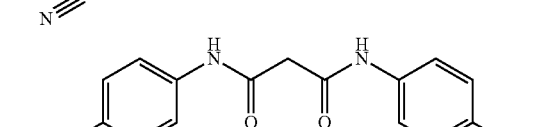
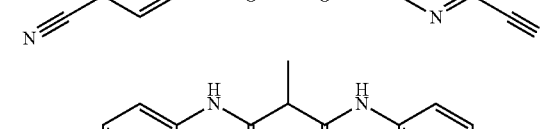
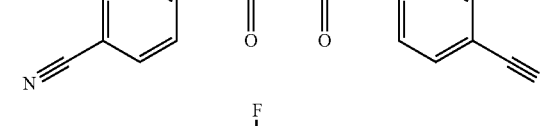
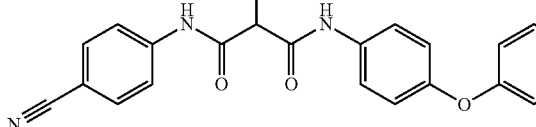
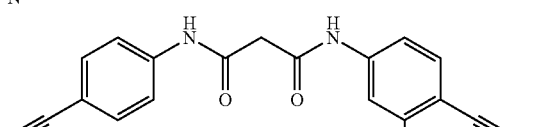
and
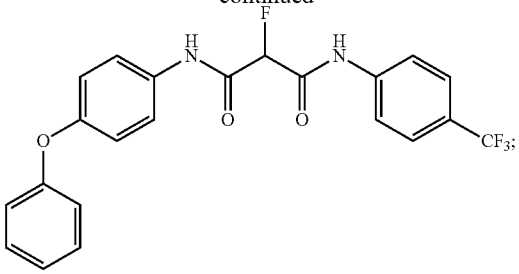
or a pharmaceutically acceptable salt thereof.
In some embodiments, the compound of Formula I is selected from:
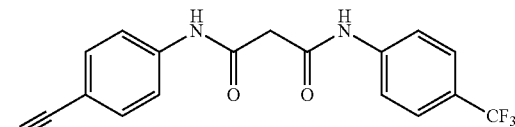
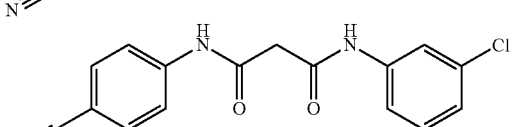
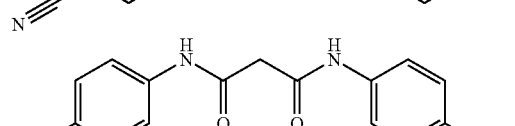
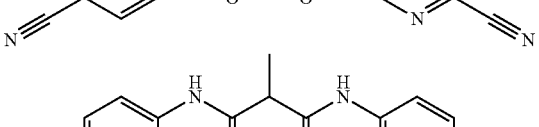
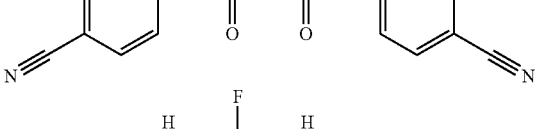
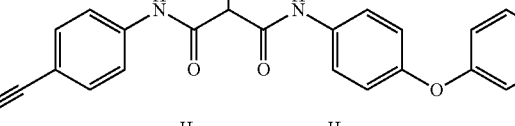
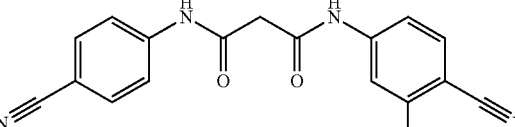
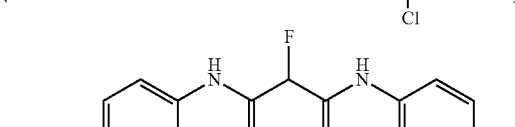
and
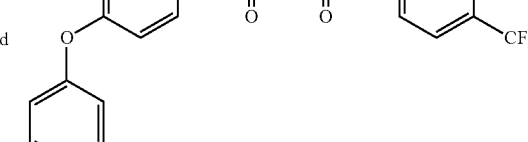
or a pharmaceutically acceptable salt thereof.
In some embodiments, the compound of Formula I or II is selected from:

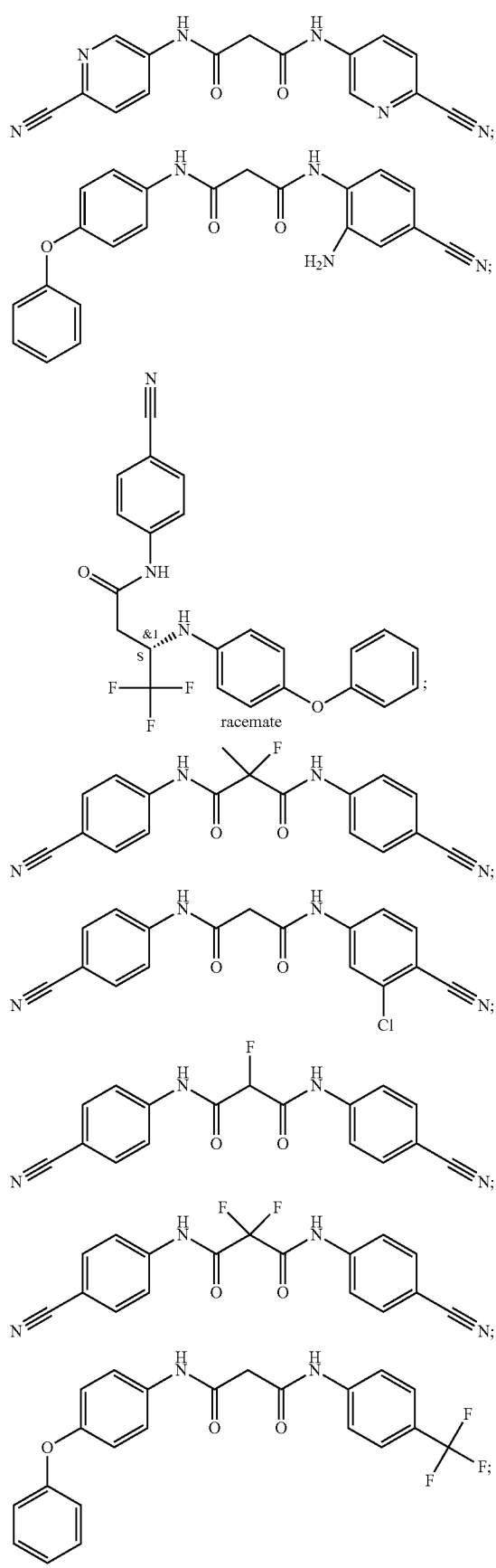

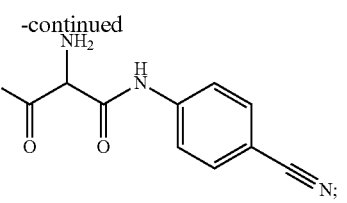

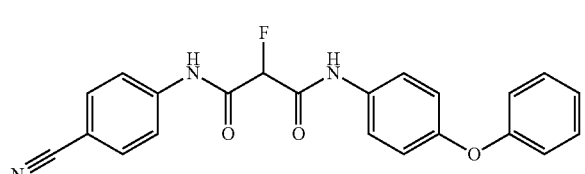

or a pharmaceutically acceptable salt thereof.

In some embodiments, the compound of Formula I or II is:

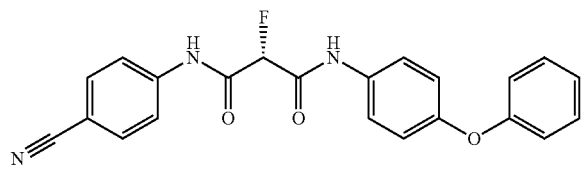 [SMILES: N#Cc1ccc(NC(=O)[C@H](F)C(=O)Nc2ccc(Oc3ccccc3)cc2)cc1]

or a pharmaceutically acceptable salt thereof.

In some embodiments, the compound of Formula I or II is:

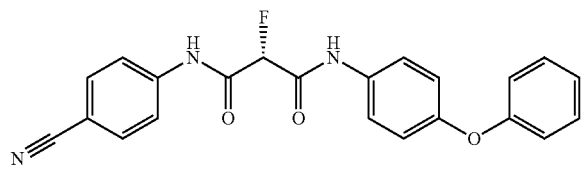 [SMILES: N#Cc1ccc(NC(=O)[C@H](F)C(=O)Nc2ccc(Oc3ccccc3)cc2)cc1]

or a pharmaceutically acceptable salt thereof.

Synthesis

Compounds of the present disclosure, including salts, hydrates, and solvates thereof, can be prepared using known organic synthesis techniques and can be synthesized according to any of numerous possible synthetic routes, e.g., as described herein.

Reactions for preparing compounds of the present disclosure can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the disclosure can involve the protection and deprotection of various chemical groups.

The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis,* 3rd. Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkylene" refers to a divalent alkyl linking group having n to m carbons. Examples of alkylene groups include, but are not limited to, methylene, ethan-1,2-diyl, propan-1,3-diyl, propan-1,2-diyl, and the like. In some embodiments, the alkylene moiety contains 1 to 6, 1 to 3, or 1 to 2 carbon atoms.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "halo" refers to F, Cl, Br, or I.

As used herein, the term "$C_{n-m}$ haloalkyl" refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only (e.g., a $C_{1-6}$ fluoroalkyl group). In some embodiments, the alkyl group has 1 to 6, 1 to 4, or 1 to 3 carbon atoms.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo (=O). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7, or 4-6 ring atoms with 1 or 2 heteroatoms independently selected from nitrogen, oxygen, or sulfur.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide-imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in Handbook of Pharmaceutical Salts: Properties, Selection, and Use, Wiley-VCH, 2002.

Methods of Use

The present disclosure provides methods for treating and/or preventing acute, chronic, and relapsing infections by administering to a subject a therapeutically effective amount of a compound described herein (e.g. a compound of Formula I or Formula II), or a pharmaceutically acceptable salt thereof. For example, the compounds described herein can be used to treat an acute infection caused by a pathogen and, as a result of treatment, inhibit or ameliorate the infection. The compounds described herein can be used to treat chronic, persistent infections caused by pathogens such as bacteria (e.g., gram negative bacteria such as *P. aeruginosa*; or gram positive bacteria) that have become tolerant to antibiotic treatment (i.e., bacterial tolerance), for example, as a result of activation of a QS system. In addition, the compounds described herein can be used for the treating gut permeability as a result of microbial involvement and bacterial infections that promote, for example, Crohn's disease (CD), a gastrointestinal inflammatory disorder.

The compounds described herein can treat individuals suffering from such chronic infections, e.g., by targeting the virulence factor pathways of these tolerant bacteria. In general, the methods can be used to treat any organism that is susceptible to bacterial infections, e.g., animals, including mammals, e.g., humans and non-human mammals, as well as plants.

In some embodiments, the method is a method of treating an antibiotic-tolerant infection in the subject. In some embodiments, the antibiotic-tolerant infection is an acute antibiotic-tolerant infection. In some embodiments, the antibiotic-tolerant infection is a relapsing antibiotic-tolerant infection.

In some embodiments, the infection is associated with a gram negative bacterium described herein. In some embodiments, the gram negative bacterium is selected from the group consisting of *Pseudomonas aeruginosa, E. coli, Acinetobacter,* and *Burkholderia* species. In some embodiments, the gram negative bacterium is *Pseudomonas aeruginosa.* In some embodiments, the gram negative bacterium is *Acinetobacter.* In some embodiments, the gram negative bacterium is *E. coli.* In some embodiments, the gram negative bacterium is *Burkholderia.* In some embodiments, the infection is associated with a gram positive bacterium described herein.

As used herein, the term "subject" or "patient" refers to any animal, including mammals and invertebrates. For example, a subject or a patient includes, but is not limited to, mice, rats, other rodents, rabbits, dogs, cats, swine, cattle, sheep, horses, primates, fish, and humans. In some embodiments, the subject is a human. In some embodiments, the subject is a mouse. In some embodiments, the methods provided herein comprise administering to the subject an effective amount of a compound or composition (e.g., a pharmaceutical composition) provided herein. In some embodiments, the methods described herein are in vitro methods. In some embodiments, the methods described herein are in vivo methods.

Patients suitable for such treatment may be identified by methods known in the art, e.g., by the detection of symptoms commonly associated with infection, such as fever, pain, pus, culture of organisms, and the like. Infections that can be treated with the compounds described herein include those caused by or due to pathogens. In some embodiments, the pathogen is a bacterium (e.g., a gram negative bacterium, e.g., *Pseudomonas,* such as *P. aeruginosa*; or a gram positive bacterium).

Exemplary clinical indications can include, but are not limited to: 1) burn and/or wound infections; 2) nosocomial pneumonia; 3) cystic fibrosis; 4) osteomyelitis; 5) sepsis in an immunosuppressed host; 6) a gastrointestinal infection (e.g., an infection associated with or resulting in intestinal hyperpermeability, or gastrointestinal inflammatory disorder); 7) a urinary tract infection; 8) an infection that modulates brain function, 9) an infection of the skin or soft tissue; or 10) any combination thereof. In some embodiments, the subject has an acute infection. In some embodiments, the subject has a chronic infection. A chronic infection can last three weeks or more, or if the infection is recurrent despite completion of antibiotic treatment. In some embodiments, the subject has a relapsing infection. In some embodiments, the following pathogenic infections can be treated using the compounds described herein (e.g. a compound of Formula II or Formula I), or a pharmaceutically acceptable salt thereof, according to the methods provided herein.

Invasive burn wound infections remains the most common cause of morbidity and mortality in extensively burned subjects. Infection is the predominant determinant of wound healing, incidence of complications, and outcome of burn subjects. The main organisms responsible are *Pseudomonas aeruginosa, S. aureus, Streptococcus pyogenes*, and various Gram-negative organisms.

Nosocomial pneumonias account for nearly 20% of all nosocomial infections. Subjects most at risk for developing nosocomial pneumonia are those in intensive care units, subjects with altered levels of consciousness, elderly subjects, subjects with chronic lung disease, ventilated subjects, smokers and post-operative subjects. In a severely compromised subject, multiantibiotic-resistant nosocomial pathogens are likely to be the cause of the pneumonia. The main organisms responsible are *P. aeruginosa, S. aureus, Klebsiella pneumoniae*, and *Enterobacter* spp.

Cystic fibrosis (CF) is the most common genetic disorder of the Caucasian population. Pulmonary disease is the most common cause of premature death in cystic fibrosis subjects. Optimum antimicrobial therapy for CF is not known, and it is generally believed that the introduction of better antipseudomonal antibiotics has been the major factor contributing to the increase in life expectancy for CF subjects. The most common organisms associated with lung disease in CF are *S. aureus, P. aeruginosa* and *H. influenzae. P. aeruginosa* is the leading pathogen.

Osteomyelitis causes the vascular supply to the bone to be compromised by infection extending into surrounding tissue. Within this necrotic and ischemic tissue, the bacteria may be difficult to eradicate even after an intense host response, surgery, and/or antibiotic therapy. The main organisms responsible are *S. aureus, E. coli*, and *P. aeruginosa*.

Treatment of infections in subjects who are immune-compromised by virtue of chemotherapy-induced granulocytopenia and immunosuppression related to organ or bone marrow transplantation can be a challenge. Neutropenic subjects are especially susceptible to bacterial infection. Organisms likely to cause infections in granulocytopenic subjects are: *S. epidermidis, S. aureus, S. viridans, Enterococcus* spp, *E. coli, Klebsiella* spp, *P. aeruginosa* and *Candida* spp.

Small bowel bacterial overgrowth syndrome (SBBOS), or small intestinal bacterial overgrowth (SIBO), also termed bacterial overgrowth; is a disorder of excessive bacterial growth in the small intestine. Certain species of bacteria are more commonly found in aspirates of the jejunum taken from patients with bacterial overgrowth. The most common isolates are *Escherichia coli, P. aeruginosa, Streptococcus, Lactobacillus, Bacteroides*, and *Enterococcus* species. See e.g. Kopacova et al. "Small Intestinal Bacterial Overgrowth Syndrome" *World J. Gastroenterol.* 16(24): 2978-2990, 2010. In some embodiments, the compounds described herein can be used to treat small intestinal bacterial overgrowth syndrome (SIBO).

Bacterial infections that promote Crohn's disease (CD), a gastrointestinal inflammatory disorder. CD is a chronic relapsing gastrointestinal inflammatory disorder that can lead to rectal bleeding, chronic diarrhea, and ultimately colorectal cancer. Intestinal microbiota of CD patients exhibit microbial population shifts characterized by a deficiency of beneficial, anti-inflammatory Firmicutes and Bacteroidetes populations and an excess of pro-inflammatory bacteria such as of the adherent-invasive *Escherichia coli* (AIEC) pathotype (see e.g., Chassaing et al, *Gastroenterology*, 2011, 140:1720-1728). Current antibiotic therapies are often contraindicated for CD since they further promote microbiota dysbiosis that promotes imbalance of the number and composition of intestinal microbes.

In some embodiments, the compounds described herein can be used to preventatively treat patients undergoing endoscopy. These patients are often found to be infected by *Pseudomonas aeruginosa* after undergoing endoscopic procedures.

In some embodiments, the compounds described herein can be used in the treatment of intestinal hyperpermeability (e.g., by reducing intestinal permeability in the subject). Burn-site infections, commonly due to *Pseudomonas aeruginosa*, have been associated with deranged intestinal integrity, allowing bacteria and their products to translocate from the gut to the circulation. The *P. aeruginosa* quorum sensing (QS) transcription factor MvfR (PqsR) controls the expression of many virulence factors, and the synthesis of several toxic products. As described herein, inhibition of MvfR function through the use of the compounds described herein significantly decreases the flux out of the gut, diminishes bacterial translocation from the intestine to mesenteric lymph nodes (MLNs), and improves tight junction (TJ) integrity. In some embodiments, the intestinal hyperpermeability is associated with a burn wound (e.g., a burn wound infection). In some embodiments, the treatment comprises reducing intestinal inflammation in the subject. In some embodiments, the present application further provides a method of treating intestinal hyperpermeability in a subject in need thereof.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Plants

Resistance of plant pathogens to antibiotics such as oxytetracycline is rare, but the emergence of streptomycin-resistant strains of *Erwinia amylovora, Pseudomonas* spp., and *Xanthomonas campestris* has impeded the control of several important plant diseases.

In some embodiments, the compounds described herein can be used to treat plant bacterial diseases. As used herein, "plants" refer to photosynthetic organisms, both eukaryotic and prokaryotic. Plants include trees and shrubs (e.g., conifers), herbs, bushes (greater than 100 different families), grasses (e.g., Gramineae, Cyperaceae, and Juncaceae), vines (any number of families using any climbing method), ferns (e.g., a species from the Psilotopsida, Equisetopsida, Marattiospida or Polypodiopsida class), mosses (i.e., bryophytes), fungi (e.g. edible and/or commercially useful varieties), and green algae (e.g., unicellular, *flagellates*, and filamentous).

Representative species of plants that may benefit from application of the compounds described herein, many of which are grown around the world for agronomic purposes, include, without limitation, corn (*Zea mays*), wheat (*Triticum* spp.), rice (*Oryza* spp.), tobacco (*Nicotiana* spp.), potatoes (*Solanum tuberosum*), cotton (*Gossypium hirsutum*), rapeseed and canola (*Brassica* spp.), and sunflower (*Helianthus annus*), as well as any number of fruits (e.g., *Malus* spp., *Citrus* spp., Vitus spp., and Musa spp.) or legumes (e.g., soybean (*Glycine max*), peas (*Pisum sativum*), and beans (from the Leguminosae family)). There are a number of flowering species (e.g., species of angiosperms) not included in any of the above-indicated plants that also may benefit from application of the compounds described herein.

Combination Therapies

When employed in methods of treating a disease, the compounds provided herein can be administered in combination with one or more additional therapeutic agents provided herein. Exemplary additional therapeutic agents include, but are not limited to, antivirulence agents, antibiotic agents and anesthetic agents (e.g., for use in combination with a surgical procedure).

In some embodiments, the compounds described herein can be used in combination with an antibiotic agent. The combination may be used to affect a synergistic or additive result, to overcome an acute, chronic, or relapsing infection, or to overcome bacterial tolerance (e.g., bacterial tolerance to the antibiotic agent).

Exemplary classes of antibiotics that can be used in combination with the compounds described herein include, but are not limited to, penicillins, cephalosporins, carbacephems, cephamycins, carbapenems, monobactams, quinolones, tetracyclines, aminoglycosides, macrolides, glycopeptides, chloramphenicols, glycylcyclines, licosamides, lipopeptides, oxazolidinones and fluoroquinolones.

Essential Structure of Quinolone Antibiotics

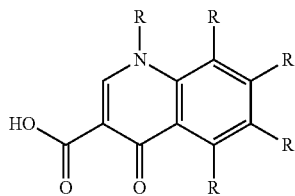

In some embodiments, the antibiotic that can be used in combination with the compounds described herein is a quinolone antibiotic. Exemplary quinolones include, but are not limited to, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, garenoxacin, delafloxacin, danofloxacin, difloxacin, enrofloxacin, ibafloxacin, marbofloxacin, orbifloxacin, and sarafloxacin.

In some embodiments, the compounds provided herein are administered in combination with rifaximin (e.g., for the treatment of SIBO).

In some embodiments, the compounds described herein can be used in combination with antibiotics that are used to treat plant bacterial diseases. Examples of antibiotics that can be used in combination include, but are not limited to, streptomycin, oxytetracycline, gentamicin, and oxolinic acid. See e.g. McManus et al. "Antibiotic Use in Plant Agriculture" *Annu. Rev. Phytopathol.* 40:443-65, 2002.

In some embodiments, the compounds are applied to the leaves of a plant (e.g., as part of a foliar spray or dust); in some embodiments, the compounds are applied to the soil surrounding a plant, or into which a plant, seed, or seedling will be placed. Compositions for use in plants can contain other agriculturally or horticulturally-acceptable or useful ingredients.

Pharmaceutical Formulations and Dosage Forms

When employed as pharmaceuticals, the compositions and therapeutic agents provided herein can be administered in the form of pharmaceutical formulations. These formulations can be prepared as described herein or elsewhere, and can be administered by a variety of routes, depending upon whether local or systemic treatment is desired and upon the area to be treated. In some embodiments, the administration is selected from the group consisting of pulmonary administration (e.g., by inhalation or insufflation of powders or aerosols, including by nebulizer, intratracheal administration, or intranasal administration), oral administration, or parenteral administration (e.g., intravenous, intraarterial, subcutaneous, intraperitoneal, intramuscular or injection or infusion, intracranial, intrathecal, intraventricular administration, and the like). In some embodiments, the administration is intravenous or nasal administration.

Parenteral administration can be in the form of a single bolus dose, or may be, for example, by a continuous perfusion pump. Conventional pharmaceutical carriers, aqueous, powder, or oily bases, thickeners and the like, may be necessary or desirable.

Also provided are pharmaceutical formulations which contain, as the active ingredient, a composition provided herein in combination with one or more pharmaceutically acceptable carriers (excipients). In making a pharmaceutical formulation provided herein, the nanoparticle composition may be, for example, mixed with an excipient or diluted by an excipient. When the excipient serves as a diluent, it can be a solid, semi-solid, or liquid material, which acts as a vehicle, carrier, or medium for the nanoparticle composition. Thus, the pharmaceutical formulations can be in the form of powders, lozenges, elixirs, suspensions, emulsions, solutions, syrups, aerosols (as a solid or in a liquid medium), sterile injectable solutions, sterile packaged powders, and the like.

Also provided herein are coatings comprising a therapeutically effective amount of a compound or composition provided herein. In some embodiments, the coating is preloaded onto a surface of a sterile instrument (e.g. a sterile surgical instrument). In some embodiments, the coating is preloaded onto a surface of a sterile bandage. In some embodiments, the coating is preloaded onto a surface of a sterile surgical staple. In some embodiments, the coating is preloaded onto a surface of a sterile surgical suture. In some embodiments, the coating is preloaded onto a surface of a sterile surgical sponge.

EXAMPLES

General Methods and Materials

The following statistical analysis will be applied for the experiments described in Examples 3-7. Median bacterial counts in lungs will be compared by the Kruskal-Wallis test for multiple comparisons, followed by Dunn's post-hoc test. Comparisons of means between multiple treatment groups will generally be performed by one-way analysis of variation (ANOVA), followed by Tukey's post-hoc test. Single mean comparisons of a treatment versus control group will generally be performed using a two-tailed, two-sample equal variance Student's t-test. GraphPad PRISM software will be used for these analyses. Differences will be considered significant at $P<0.05$.

Example 1. Structure-Activity Relationship (SAR) Studies

Structure activity relationship studies (SAR) of previously reported compounds (see e.g., Starkey et al, *PLoS Pathog.* 2014, 10:e1004321) yielded robust, stable, MvfR inhibitors. A list of compounds identified in the SAR studies described herein are shown below in Table 1.

TABLE 1

| Compound No. | Code | Structure |
|---|---|---|
| 1 | M17 | 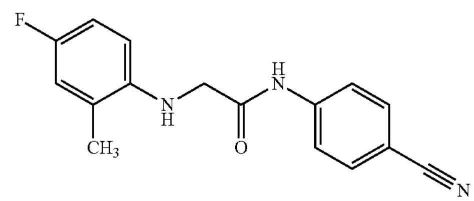 [SMILES: Cc1cc(F)ccc1NCC(=O)Nc1ccc(C#N)cc1] |
| 2 | G1 | 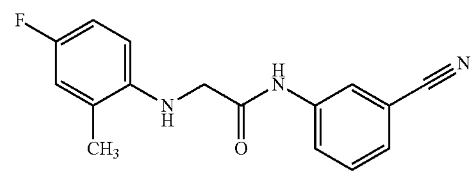 [SMILES: Cc1cc(F)ccc1NCC(=O)Nc1cccc(C#N)c1] |
| 3 | G2 | 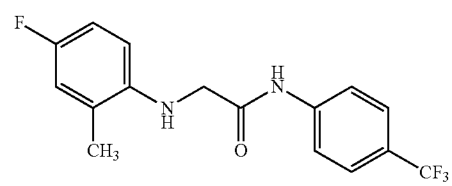 [SMILES: Cc1cc(F)ccc1NCC(=O)Nc1ccc(C(F)(F)F)cc1] |
| 4 | G3 | 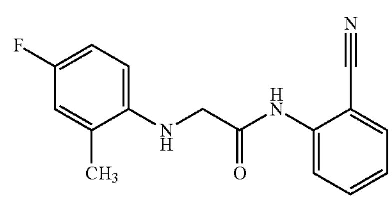 [SMILES: Cc1cc(F)ccc1NCC(=O)Nc1ccccc1C#N] |
| 5 | G4 | 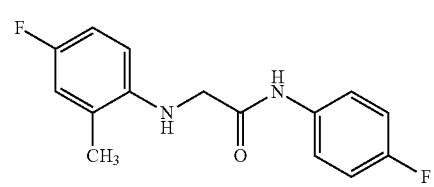 [SMILES: Cc1cc(F)ccc1NCC(=O)Nc1ccc(F)cc1] |
| 6 | G5 | 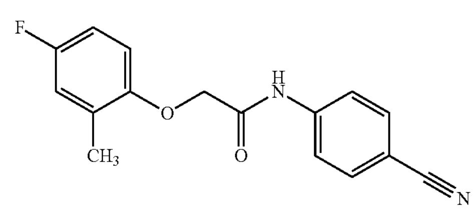 [SMILES: Cc1cc(F)ccc1OCC(=O)Nc1ccc(C#N)cc1] |

TABLE 1-continued

| Compound No. | Code | Structure |
|---|---|---|
| 7 | G6 | 4-fluoro-2-methylphenyl-NH-CH(CH₃)-C(=O)-NH-(4-cyanophenyl) |
| 8 | G7 | 4-fluoro-2-methylphenyl-O-CH₂-C(=O)-NH-(4-fluorophenyl) |
| 9 | G8 | 4-fluorophenyl-NH-CH₂-C(=O)-NH-(4-cyanophenyl) |
| 10 | G9 | 2-methylphenyl-NH-CH₂-C(=O)-NH-(4-cyanophenyl) |
| 11 | G10 | 4-chloro-2-methylphenyl-NH-CH₂-C(=O)-NH-(4-cyanophenyl) |
| 12 | G11 | 2-methylphenyl-N(CH₃)-CH₂-C(=O)-NH-(4-cyanophenyl) |
| 13 | D1 | 4-fluoro-2-methylphenyl-NH-CH(CH₃)-C(=O)-NH-(4-cyanophenyl) |
| 14 | D2 | 4-fluoro-2-methylphenyl-NH-CH₂-C(=O)-NH-(2-bromophenyl) |

TABLE 1-continued

| Compound No. | Code | Structure |
|---|---|---|
| 15 | D3 | 2-ethylphenyl-NH-CH2-C(=O)-NH-(4-cyanophenyl) |
| 16 | D4 | 2,4-difluorophenyl-NH-CH2-C(=O)-NH-(4-cyanophenyl) |
| 17 | D5 | 4-fluoro-2-methylphenyl-NH-CH2-C(=O)-NH-(4-morpholinophenyl) |
| 18 | D6 | 3-fluorophenyl-NH-CH2-C(=O)-NH-(4-cyanophenyl) |
| 19 | D7 | 4-fluoro-2-methylphenyl-NH-CH2-C(=O)-NH-(4-bromo-2-methylphenyl) |
| 20 | D8 | 4-acetylphenyl-NH-C(=O)-CH2-NH-(4-fluoro-2-methylphenyl) |
| 21 | D9 | 4-fluoro-2-methylphenyl-NH-CH2-C(=O)-NH-(4-(2-oxopyrrolidin-1-yl)phenyl) |

TABLE 1-continued

| Compound No. | Code | Structure |
|---|---|---|
| 22 | D10 | 2-(4-fluoro-2-methylphenylamino)-N-(2,6-difluorophenyl)acetamide |
| 23 | D11 | 2-(4-fluoro-2-methylphenylamino)-N-(methylcarbamoyl)acetamide |
| 24 | D12 | 2-(4-fluoro-2-methylphenylamino)-N-(2-bromo-4-methylphenyl)acetamide |
| 25 | D13 | 2-(4-fluoro-2-methylphenylamino)-N-(3-cyanophenyl)acetamide |
| 26 | D14 | 2-(4-fluoro-2-methylphenylamino)-N-(3-nitrophenyl)acetamide |
| 27 | D15 | 2-(4-fluoro-2-methylphenylamino)-N-(4-methoxyphenyl)acetamide |
| 28 | D16 | 2-(4-chlorophenylamino)-N-(4-cyanophenyl)acetamide |

TABLE 1-continued
| Compound No. | Code | Structure |
|---|---|---|
| 29 | D17 | 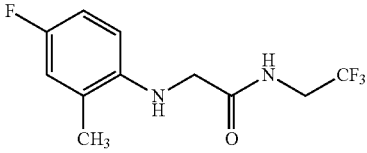 [SMILES: Cc1cc(F)ccc1NCC(=O)NCC(F)(F)F] |
| 30 | D18 | 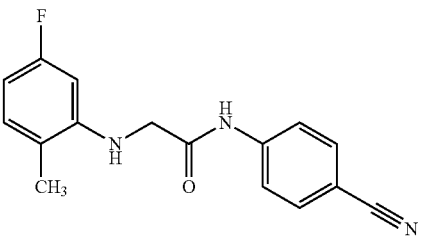 [SMILES: Cc1ccc(F)cc1NCC(=O)Nc1ccc(C#N)cc1] |
| 31 | D19 | 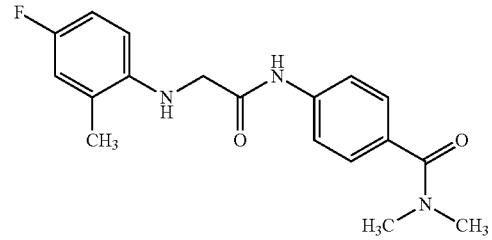 [SMILES: Cc1cc(F)ccc1NCC(=O)Nc1ccc(C(=O)N(C)C)cc1] |
| 32 | D20 | 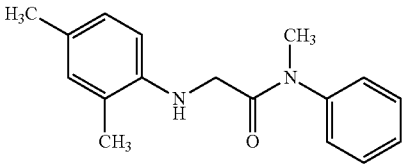 [SMILES: Cc1ccc(NCC(=O)N(C)c2ccccc2)c(C)c1] |
| 33 | D21 | 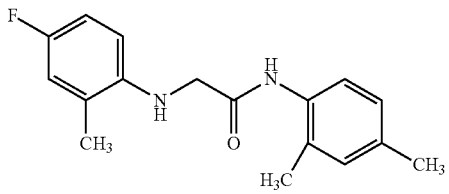 [SMILES: Cc1ccc(NC(=O)CNc2ccc(F)cc2C)c(C)c1] |
| 34 | D22 | 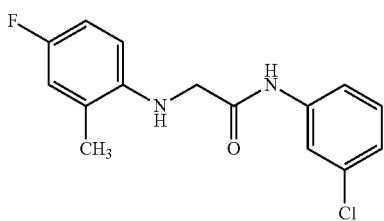 [SMILES: Cc1cc(F)ccc1NCC(=O)Nc1cccc(Cl)c1] |
| 35 | D23 | 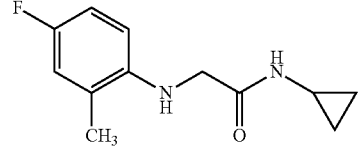 [SMILES: Cc1cc(F)ccc1NCC(=O)NC1CC1] |

TABLE 1-continued
| Compound No. | Code | Structure |
|---|---|---|
| 36 | D24 | 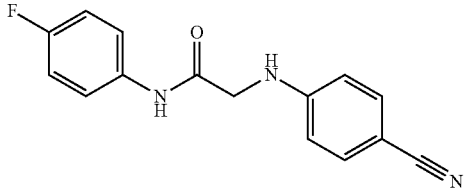 [SMILES: N#Cc1ccc(NCC(=O)Nc2ccc(F)cc2)cc1] |
| 37 | D25 | 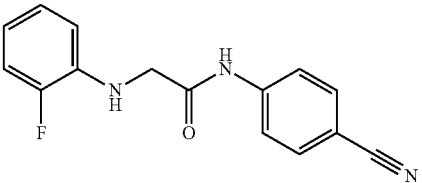 [SMILES: N#Cc1ccc(NC(=O)CNc2ccccc2F)cc1] |
| 38 | D26 | 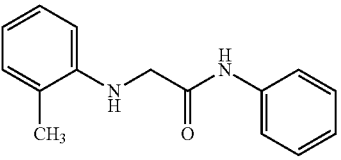 [SMILES: Cc1ccccc1NCC(=O)Nc1ccccc1] |
| 39 | D27 | 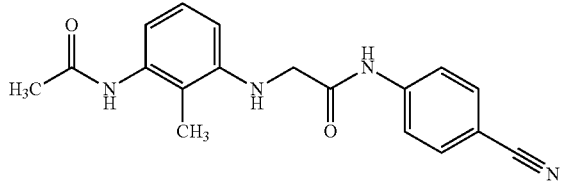 [SMILES: CC(=O)Nc1cccc(NCC(=O)Nc2ccc(C#N)cc2)c1C] |
| 40 | D28 | 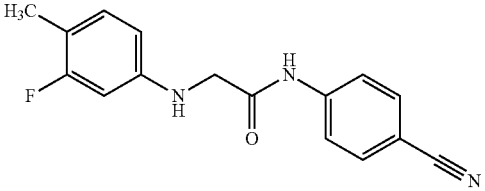 [SMILES: Cc1ccc(NCC(=O)Nc2ccc(C#N)cc2)cc1F] |
| 41 | D29 | 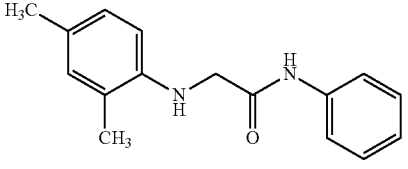 [SMILES: Cc1ccc(NCC(=O)Nc2ccccc2)c(C)c1] |
| 42 | D30 | 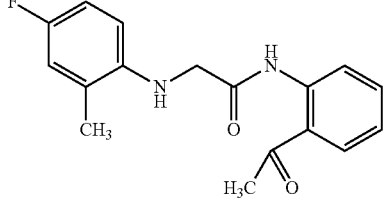 |
| 43 | D31 | 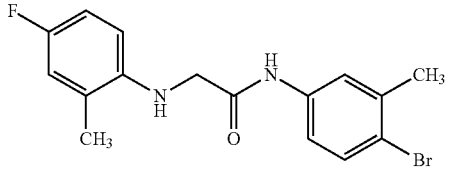 [SMILES: Cc1cc(NC(=O)CNc2ccc(F)cc2C)ccc1Br] |

TABLE 1-continued

| Compound No. | Code | Structure |
|---|---|---|
| 44 | D32 | 4-fluoro-2-methylphenyl-NH-CH2-C(=O)-NH-(3-methoxyphenyl) |
| 45 | D33 | 4-isopropylphenyl-NH-CH2-C(=O)-NH-(4-cyanophenyl) |
| 46 | D34 | 4-fluorophenyl-NH-CH2CH2-C(=O)-NH-(4-cyanophenyl) |
| 47 | D35 | 2,4-difluorophenyl-NH-CH2CH2-C(=O)-NH-(4-cyanophenyl) |
| 48 | D36 | 4-fluorophenyl-NH-C(=O)-CH2-C(=O)-NH-(4-cyanophenyl) |
| 49 | D37 | 4-fluorophenyl-NH-C(=O)-C(=O)-NH-(4-cyanophenyl) |
| 50 | D38 | 1-(4-fluoro-2-methylphenyl)piperidin-3-yl-NH-C(=O)-(4-cyanophenyl) |
| 51 | D39 | 4-fluoro-2-methylphenyl-CH2CH2-NH-C(=O)-(4-cyanophenyl) |

TABLE 1-continued

| Compound No. | Code | Structure |
|---|---|---|
| 52 | D40 | 4-fluoro-2-methylphenyl-NH-C(=O)-CH2-(4-cyanophenyl) |
| 53 | D41 | 4-chlorophenyl-NH-C(=O)-CH2-C(=O)-NH-(4-cyanophenyl) |
| 54 | D42 | 4-bromophenyl-NH-C(=O)-CH2-C(=O)-NH-(4-cyanophenyl) |
| 55 | D42 Br1 | 4-cyanophenyl-NH-C(=O)-CH2-C(=O)-NH-(2-bromophenyl) |
| 56 | D42 Br2 | 4-cyanophenyl-NH-C(=O)-CH2-C(=O)-NH-(3-bromophenyl) |
| 57 | D43 | 4-cyanophenyl-NH-C(=O)-CH2-C(=O)-NH-(4-cyanophenyl) |
| 58 | D44 | 4-fluorophenyl-C(=O)-NH-CH2-C(=O)-NH-(4-cyanophenyl) |
| 59 | D45 | 4-fluorophenyl-N(CH3)-C(=O)-CH2-C(=O)-NH-(4-cyanophenyl) |
| 60 | D46 | 4-fluorophenyl-NH-C(=S)-CH2-C(=S)-NH-(4-cyanophenyl) |

TABLE 1-continued

| Compound No. | Code | Structure |
|---|---|---|
| 61 | D47 | 4-F-C6H4-NH-C(O)-CH2CH2-C(O)-NH-C6H4-4-CN |
| 62 | D48 | 4-F-2-Me-C6H3-NH-C(O)-CH2-C(O)-NH-C6H4-4-CN |
| 63 | D49 | 4-(CH3C(O))-C6H4-NH-C(O)-CH2-C(O)-NH-C6H4-4-CN |
| 64 | D50 | 4-(CF3C(O))-C6H4-NH-C(O)-CH2-C(O)-NH-C6H4-4-CN |
| 65 | D51 | 4-O2N-C6H4-NH-C(O)-CH2-C(O)-NH-C6H4-4-CN |
| 66 | D51P | 4-NC-C6H4-NH-C(O)-CH2-C(O)-NH-C6H4-4-NO2 |
| 67 | D52 | 4-H2N-C6H4-NH-C(O)-CH2-C(O)-NH-C6H4-4-CN |
| 68 | D53 | 4-(CH3C(O)NH)-C6H4-NH-C(O)-CH2-C(O)-NH-C6H4-4-CN |
| 69 | D54 | 4-(CF3C(O)NH)-C6H4-NH-C(O)-CH2-C(O)-NH-C6H4-4-CN |

TABLE 1-continued

| Compound No. | Code | Structure |
|---|---|---|
| 70 | D55 | 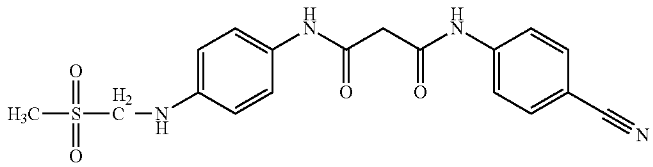 [SMILES: CS(=O)(=O)CNc1ccc(NC(=O)CC(=O)Nc2ccc(C#N)cc2)cc1] |
| 71 | D56 | 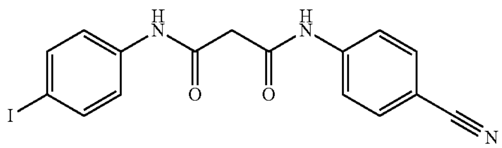 [SMILES: N#Cc1ccc(NC(=O)CC(=O)Nc2ccc(I)cc2)cc1] |
| 72 | D57 | 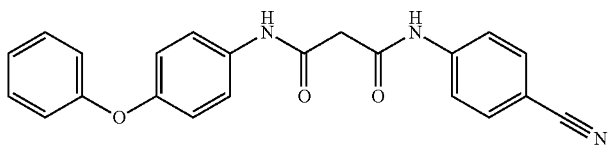 [SMILES: N#Cc1ccc(NC(=O)CC(=O)Nc2ccc(Oc3ccccc3)cc2)cc1] |
| 73 | D58 | 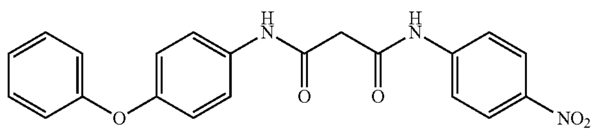 [SMILES: O=C(CC(=O)Nc1ccc([N+](=O)[O-])cc1)Nc1ccc(Oc2ccccc2)cc1] |
| 74 | D59 | 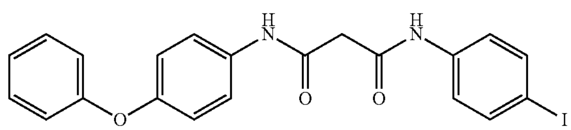 [SMILES: O=C(CC(=O)Nc1ccc(Oc2ccccc2)cc1)Nc1ccc(I)cc1] |
| 75 | D60 | 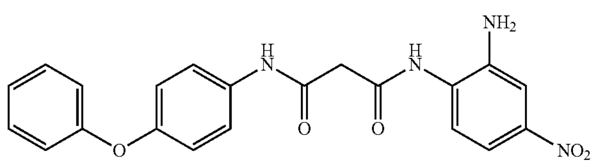 [SMILES: Nc1cc([N+](=O)[O-])ccc1NC(=O)CC(=O)Nc1ccc(Oc2ccccc2)cc1] |
| 76 | D61 | 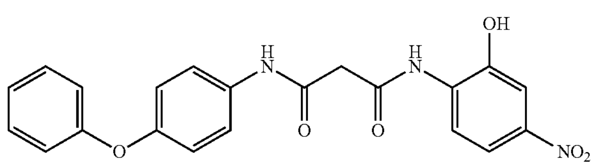 [SMILES: O=C(CC(=O)Nc1ccc([N+](=O)[O-])cc1O)Nc1ccc(Oc2ccccc2)cc1] |
| 77 | D62 | 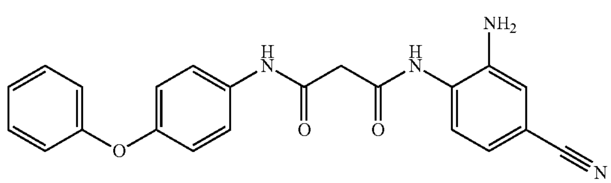 |
| 78 | D63 | 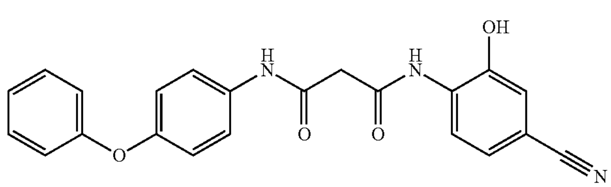 [SMILES: N#Cc1ccc(NC(=O)CC(=O)Nc2ccc(Oc3ccccc3)cc2)c(O)c1] |

TABLE 1-continued

| Compound No. | Code | Structure |
|---|---|---|
| 79 | D64 | 4-phenoxyphenyl-NH-C(O)-CH2-C(O)-NH-(4-bromophenyl) |
| 80 | D65 | 4-phenoxyphenyl-NH-C(O)-CH2-C(O)-N(6-cyano-2-oxo-benzoxazol-3-yl) |
| 81 | D66 | 4-phenoxyphenyl-NH-C(O)-CH2-C(O)-N(6-cyano-2-oxo-2,3-dihydro-1H-benzimidazol-1-yl) |
| 82 | D67 | 4-phenoxyphenyl-NH-C(O)-CH2-C(O)-NH-(4-chlorophenyl) |
| 83 | D68 | 4-phenoxyphenyl-NH-C(O)-CH2-C(O)-NH-(4-fluorophenyl) |
| 84 | D69 | 4-cyanophenyl-NH-C(O)-CH2-C(O)-NH-(4-trifluoromethylphenyl) |
| 85 | D70 | 4-cyanophenyl-NH-C(O)-CH2-C(O)-NH-(3-methylphenyl) |
| 86 | D71 | 4-cyanophenyl-NH-C(O)-CH2-C(O)-NH-(3-chlorophenyl) |
| 87 | D72 | 4-cyanophenyl-NH-C(O)-CH2-C(O)-NH-(3-fluorophenyl) |
| 88 | D73 | 4-cyanophenyl-NH-C(O)-CH2-C(O)-NH-(5-fluoropyridin-2-yl) |

TABLE 1-continued

| Compound No. | Code | Structure |
|---|---|---|
| 89 | D74 | 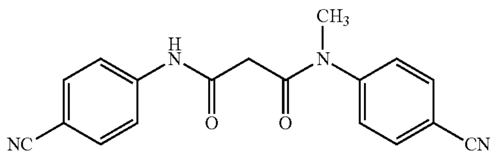 [SMILES: CN(C(=O)CC(=O)Nc1ccc(C#N)cc1)c1ccc(C#N)cc1] |
| 90 | D75 | 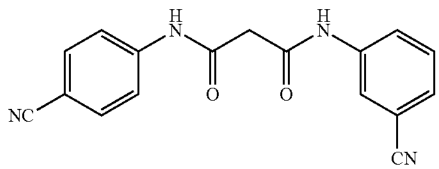 [SMILES: N#Cc1ccc(NC(=O)CC(=O)Nc2cccc(C#N)c2)cc1] |
| 91 | D76 | 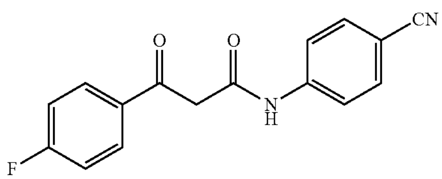 [SMILES: N#Cc1ccc(NC(=O)CC(=O)c2ccc(F)cc2)cc1] |
| 92 | D77 | 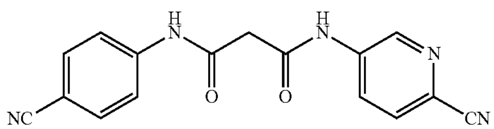 [SMILES: N#Cc1ccc(NC(=O)CC(=O)Nc2ccc(C#N)nc2)cc1] |
| 93 | D78 | 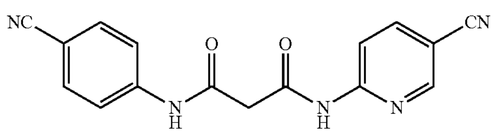 [SMILES: N#Cc1ccc(NC(=O)CC(=O)Nc2ccc(C#N)cn2)cc1] |
| 94 | D79 | 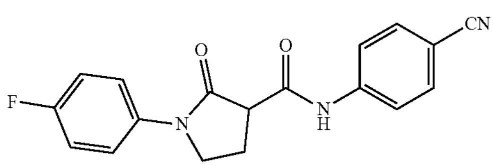 [SMILES: N#Cc1ccc(NC(=O)C2CCN(c3ccc(F)cc3)C2=O)cc1] |
| 95 | D80 | 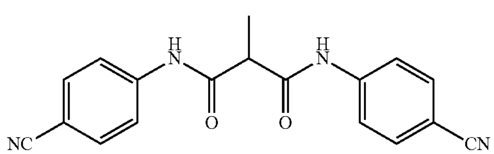 [SMILES: CC(C(=O)Nc1ccc(C#N)cc1)C(=O)Nc1ccc(C#N)cc1] |
| 96 | D81 | 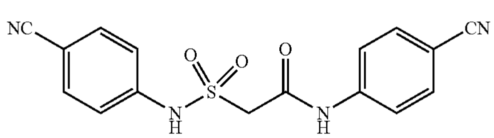 [SMILES: N#Cc1ccc(NC(=O)CS(=O)(=O)Nc2ccc(C#N)cc2)cc1] |
| 97 | D82 | 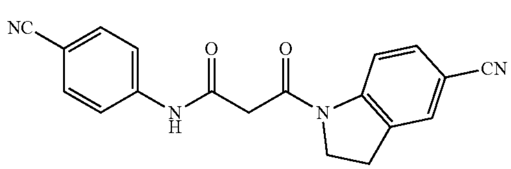 [SMILES: N#Cc1ccc(NC(=O)CC(=O)N2CCc3cc(C#N)ccc32)cc1] |

TABLE 1-continued

| Compound No. | Code | Structure |
|---|---|---|
| 98 | D83 | 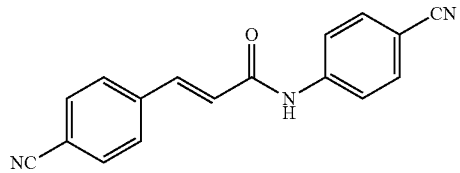 [SMILES: N#Cc1ccc(/C=C/C(=O)Nc2ccc(C#N)cc2)cc1] |
| 99 | D84 | 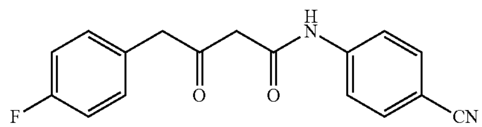 [SMILES: N#Cc1ccc(NC(=O)CC(=O)Cc2ccc(F)cc2)cc1] |
| 100 | D85 | 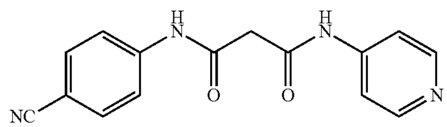 [SMILES: N#Cc1ccc(NC(=O)CC(=O)Nc2ccncc2)cc1] |
| 101 | D86 | 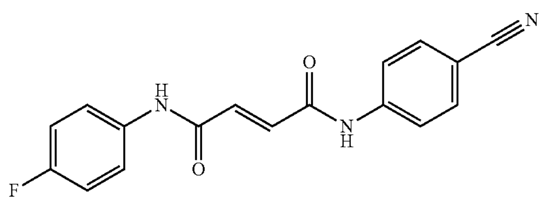 [SMILES: N#Cc1ccc(NC(=O)/C=C/C(=O)Nc2ccc(F)cc2)cc1] |
| 102 | D87 | 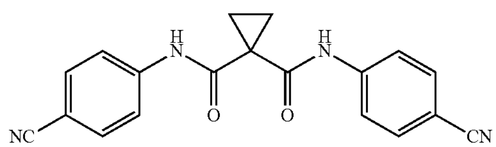 [SMILES: N#Cc1ccc(NC(=O)C2(C(=O)Nc3ccc(C#N)cc3)CC2)cc1] |
| 103 | D88 | 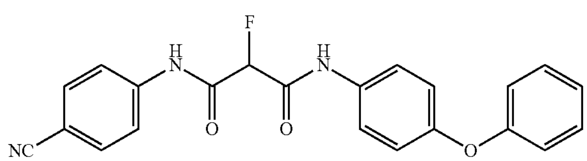 [SMILES: N#Cc1ccc(NC(=O)C(F)C(=O)Nc2ccc(Oc3ccccc3)cc2)cc1] |
| 104 | D89 | 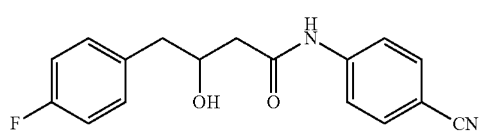 |
| 105 | D90 | 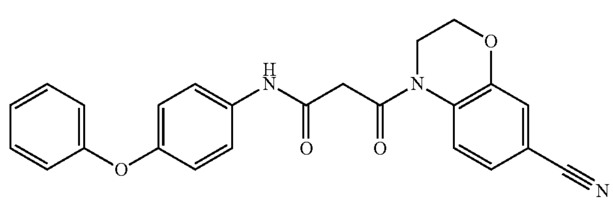 [SMILES: N#Cc1ccc2c(c1)OCCN2C(=O)CC(=O)Nc1ccc(Oc2ccccc2)cc1] |
| 106 | D91 | 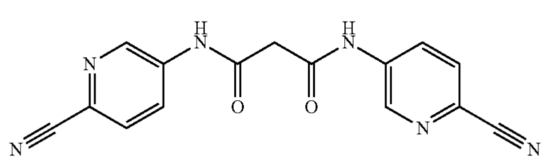 |

TABLE 1-continued
| Compound No. | Code | Structure |
|---|---|---|
| 107 | D92 | 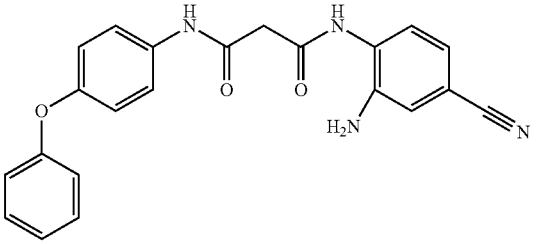 [SMILES: N#Cc1ccc(NC(=O)CC(=O)Nc2ccc(Oc3ccccc3)cc2)c(N)c1] |
| 108 | D93 | 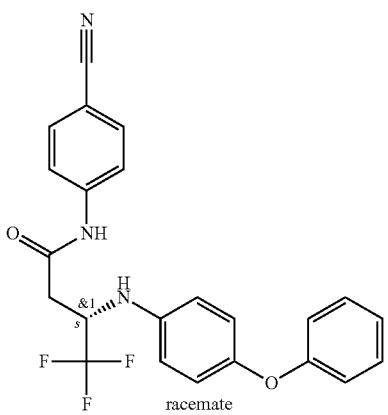 [SMILES: N#Cc1ccc(NC(=O)C[C@H](Nc2ccc(Oc3ccccc3)cc2)C(F)(F)F)cc1] |
| 109 | D94 | 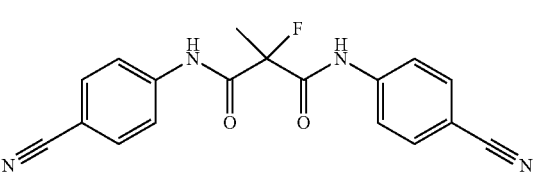 [SMILES: CC(F)(C(=O)Nc1ccc(C#N)cc1)C(=O)Nc1ccc(C#N)cc1] |
| 110 | D95 | 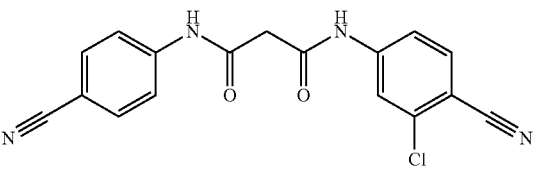 [SMILES: N#Cc1ccc(NC(=O)CC(=O)Nc2ccc(C#N)c(Cl)c2)cc1] |
| 111 | D96 | 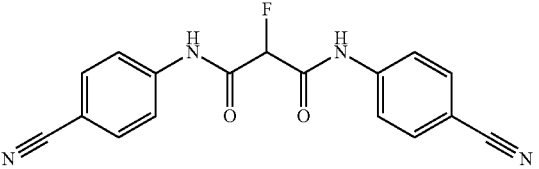 [SMILES: N#Cc1ccc(NC(=O)C(F)C(=O)Nc2ccc(C#N)cc2)cc1] |
| 112 | D97 | 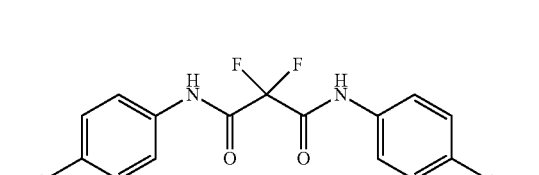 |

TABLE 1-continued

| Compound No. | Code | Structure |
|---|---|---|
| 113 | D98 | 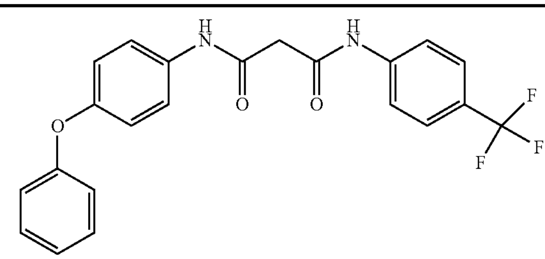 |
| 114 | D99 | 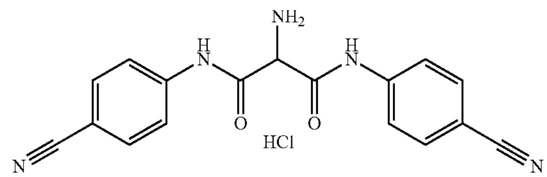 [SMILES: N#Cc1ccc(NC(=O)C(N)C(=O)Nc2ccc(C#N)cc2)cc1 ; Cl] |
| 115 | D100 | 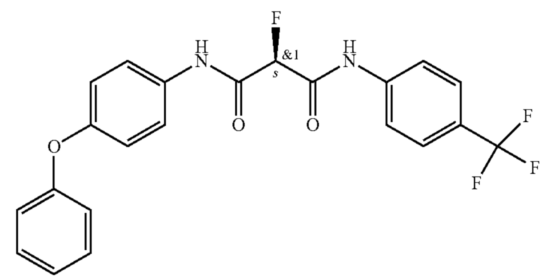 [SMILES: O=C(Nc1ccc(Oc2ccccc2)cc1)[C@@H](F)C(=O)Nc1ccc(C(F)(F)F)cc1] |

Figure 5A:
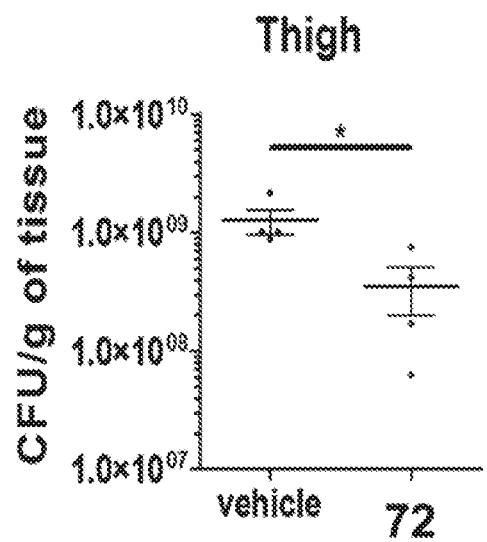
FIGS. 5A-5D show that Compounds 54 and 72 decrease bacterial dissemination and titer at the infection site in a thigh and lung model. Mice were infected with $5 \times 10^5$ and $5 \times 10^6$ PA14 cells for the thigh and lung infection model respectively.
Figure 5B:
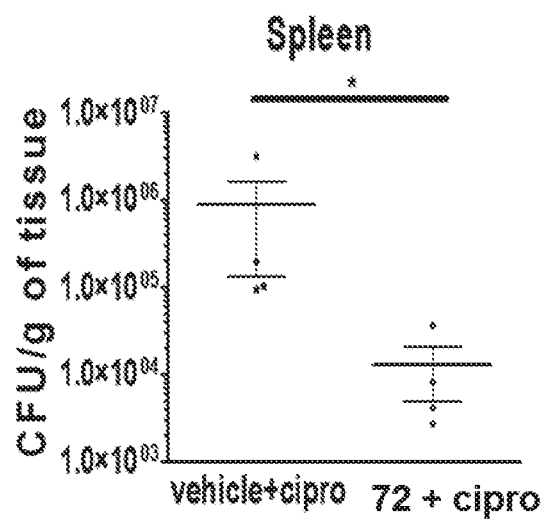
Figure 5C:
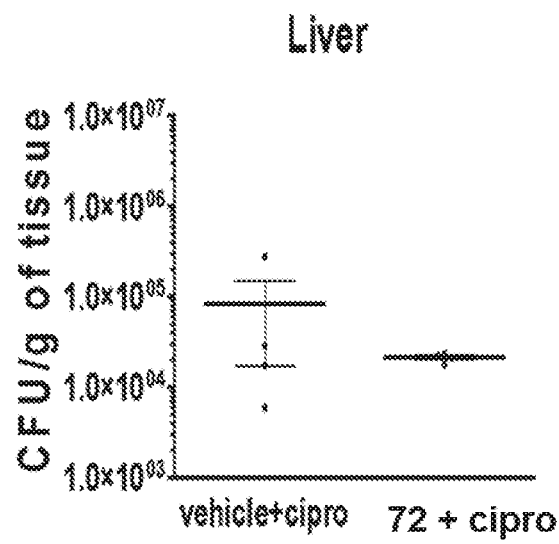
Figure 5D:
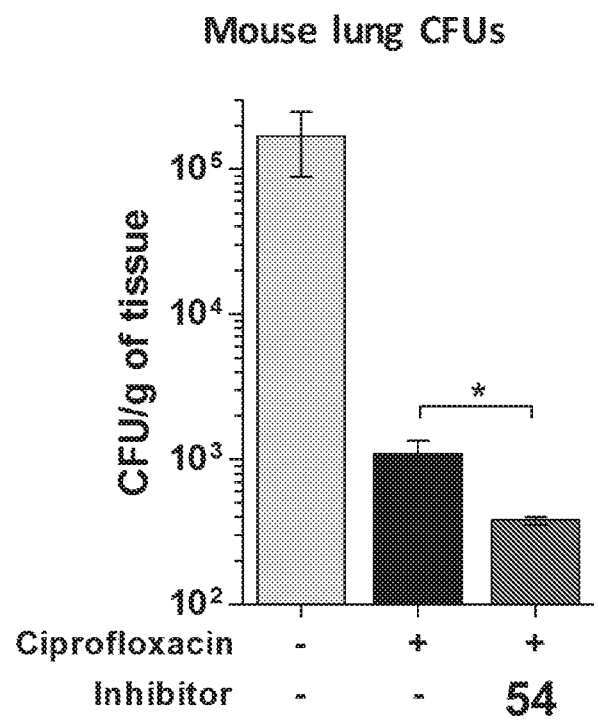
Figures 6A, 6B, 6C, 6D, 6E:
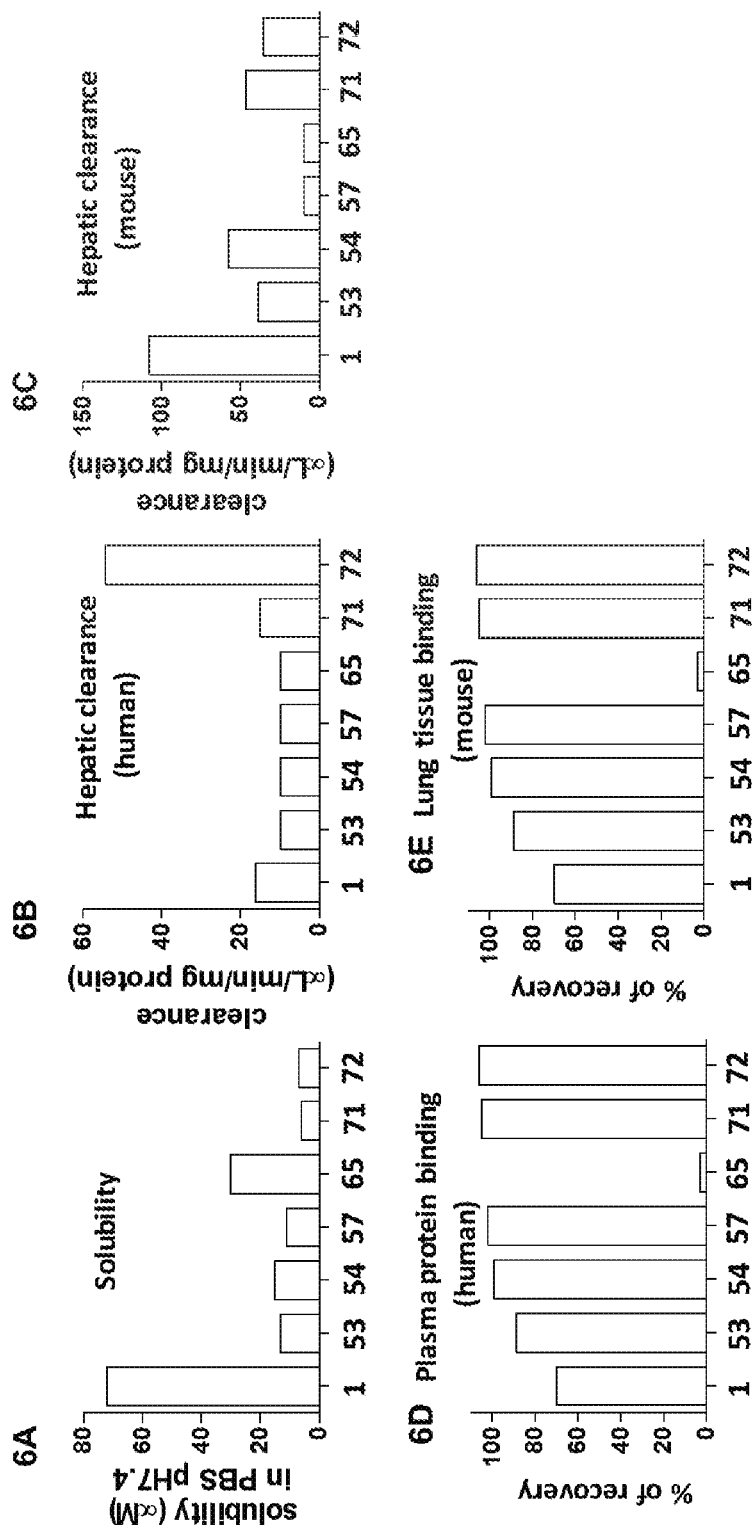
FIGS. 6A-6E show pharmacological properties of a representative group of MvfR inhibitors.

Representative examples showing the potency of inhibitors resulting from the SAR studies are shown in FIGS. 1A-2C and 4A-4G. For example, in vitro persistence analyses have demonstrated that Compounds 53-54 can inhibit persistence at a concentration of 50 µM, as shown in FIG. 1A. Furthermore, these inhibitors bind to MvfR with high affinity, as shown in FIG. 1B, and significantly reduce hydroxy-2-alkylquinoline (HAQ) and 2-AA production 5 to 10-fold, as shown in FIG. 1C (data shown for Compound 54). Preliminary acute lung infection studies suggest that Compound 54 reduces the recoverable CFUs from infected lungs, as shown in FIG. 1E. Moreover, Compound 54 potentiates ciprofloxacin efficacy in reducing PA cells in mice lungs, and significant reductions in bacterial load were observed, as shown in FIG. 5D.

Figure 1E:
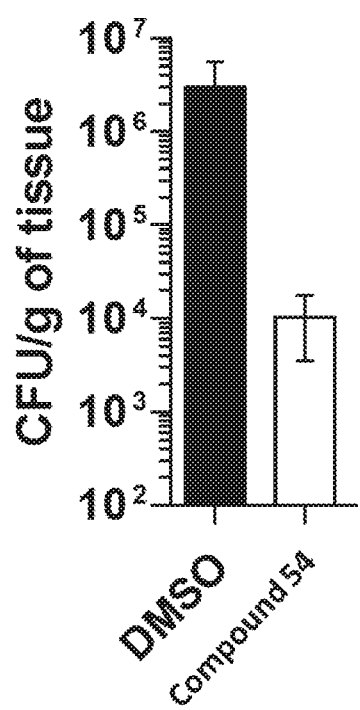
FIG. 1E shows preliminary data of Compound 54 efficacy in vivo. Mice were intranasally infected with P. aeruginosa according to reported procedures (see e.g., Starkey et al, PLoS Pathog. 2014, 10:e1004321) and treated with 10 mg/kg Compound 54 or vehicle (DMSO) control. Data are expressed as CFUs per gram of lung homogenate (n=3 per group).
Figure 1F:
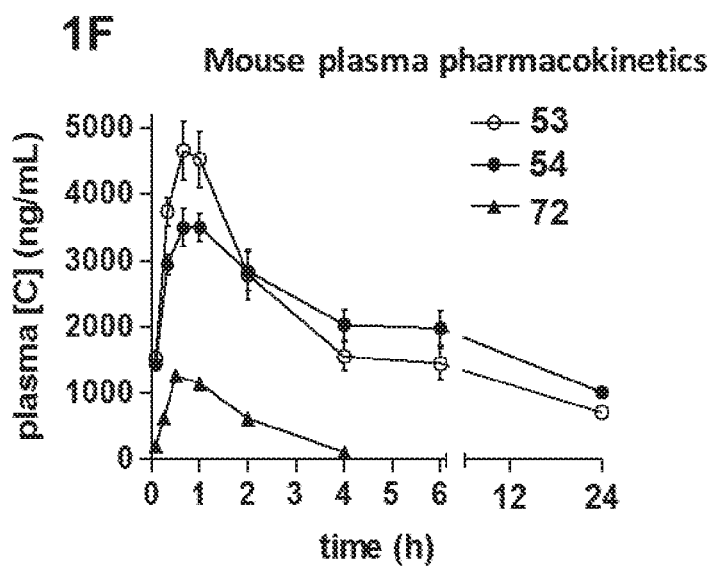
FIGS. 1F-1G show pharmacokinetics measured in mouse plasma (FIG. 1F) and lung (FIG. 1G) following a single subcutaneous injection of Compounds 53, 54, or 72 at 10 mg/kg.
Figure 1G:
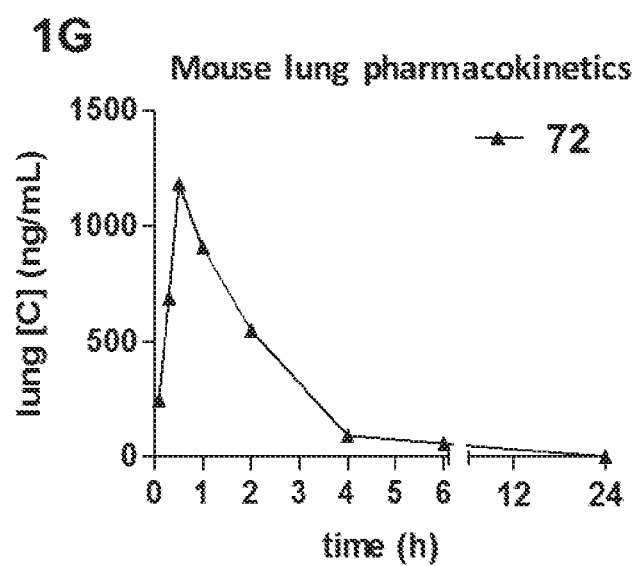
Figure 1H:
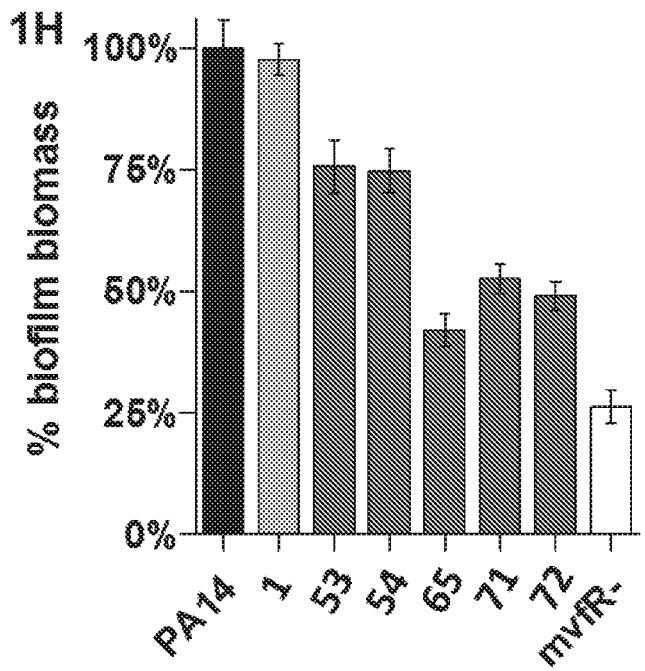
FIG. 1H shows biofilm biomass quantified by crystal violet measured at 24 hours of PA cells grown in presence 50 µM of single compounds. (p<0.005, unpaired t test with Bonferroni correction).
Figure 1I:
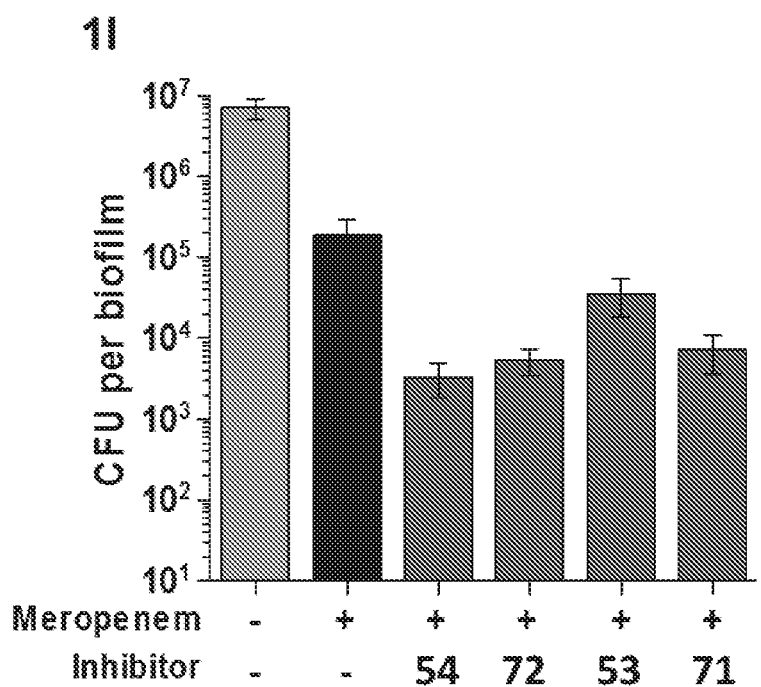
FIG. 1I shows biofilm tolerance to the antibiotic meropenem measured after 48 hours of biofilm development. Compounds were added at 50 µM simultaneously with antibiotics to disrupt preformed biofilms. Error bars show mean±SEM of at least three replicates.
Figure 2A:
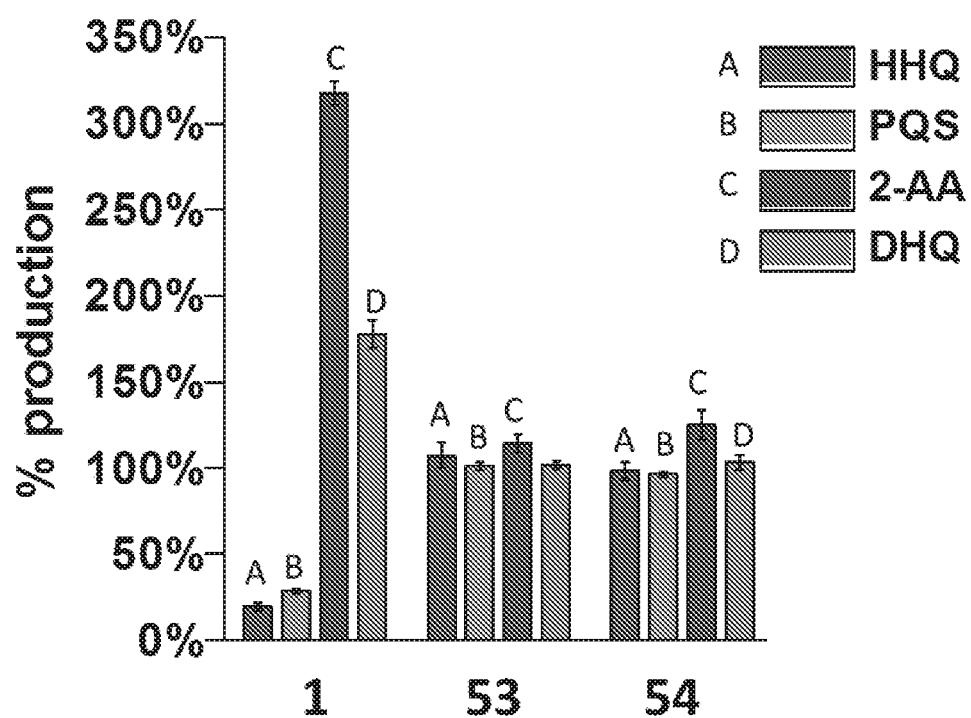
FIG. 2A shows HAQs measured in an mvfR mutant strain constitutively expressing the pqs operon to discriminate between anti-MvfR or anti-PQS operon enzymatic activity.
Figure 2B:
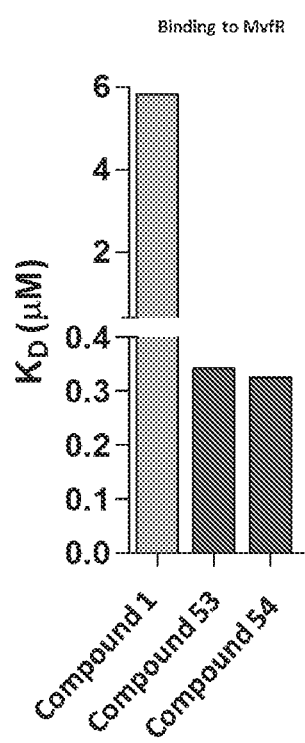
FIG. 2B shows compound interference with MvfR assessed by measuring the ability to bind MvfR via surface plasmon resonance (SPR) using a wide range of compound concentrations.
Figure 2C:
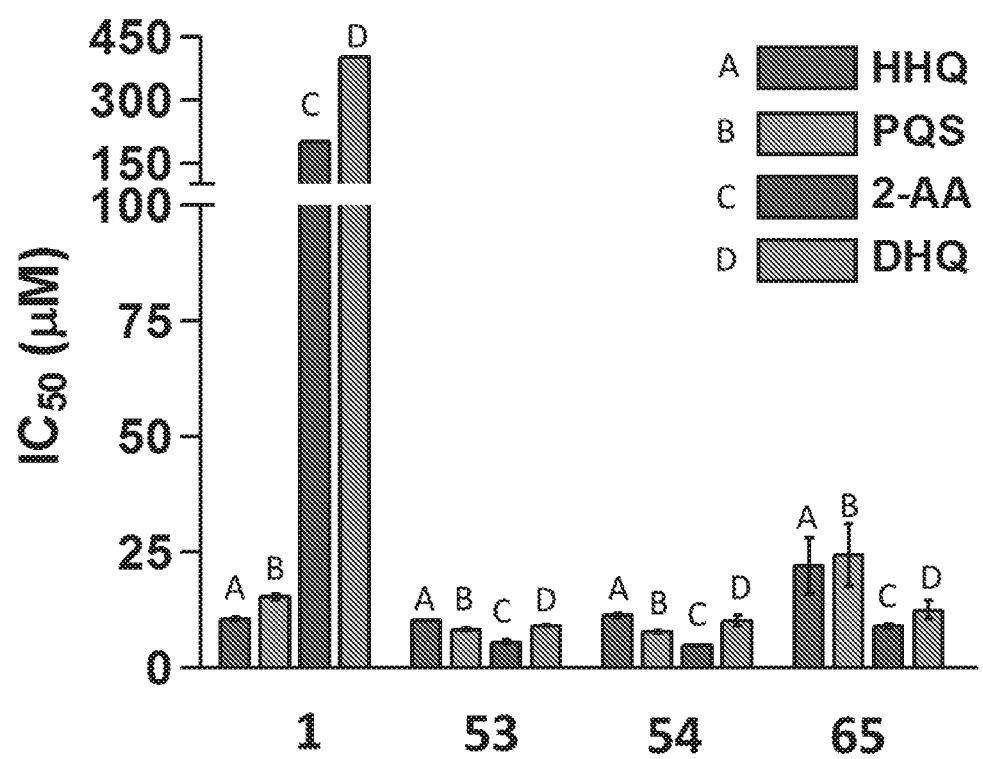
FIG. 2C shows $IC_{50}$ of Compounds 1, 53, 54, and 65 and the potency at reducing HHQ, PQS, 2-AA, and DHQ in live PA14 cells measured over a range of compound concentrations.
Figure 2D:
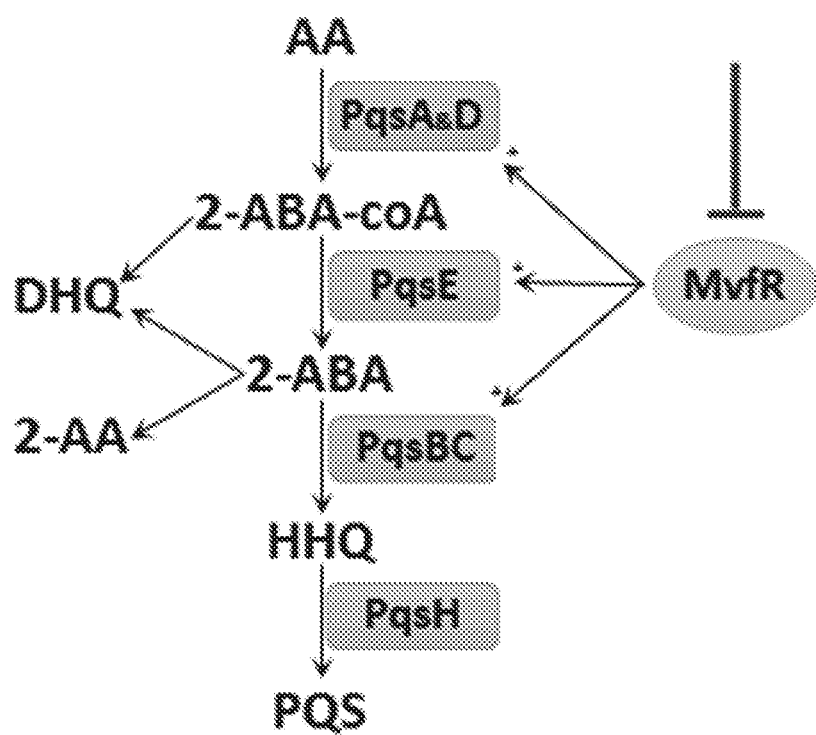
FIG. 2D shows a representative biosynthetic pathway model showing that inhibition of MvfR results in decrease or no expression of the genes indicated by the arrows.
Figure 2E:
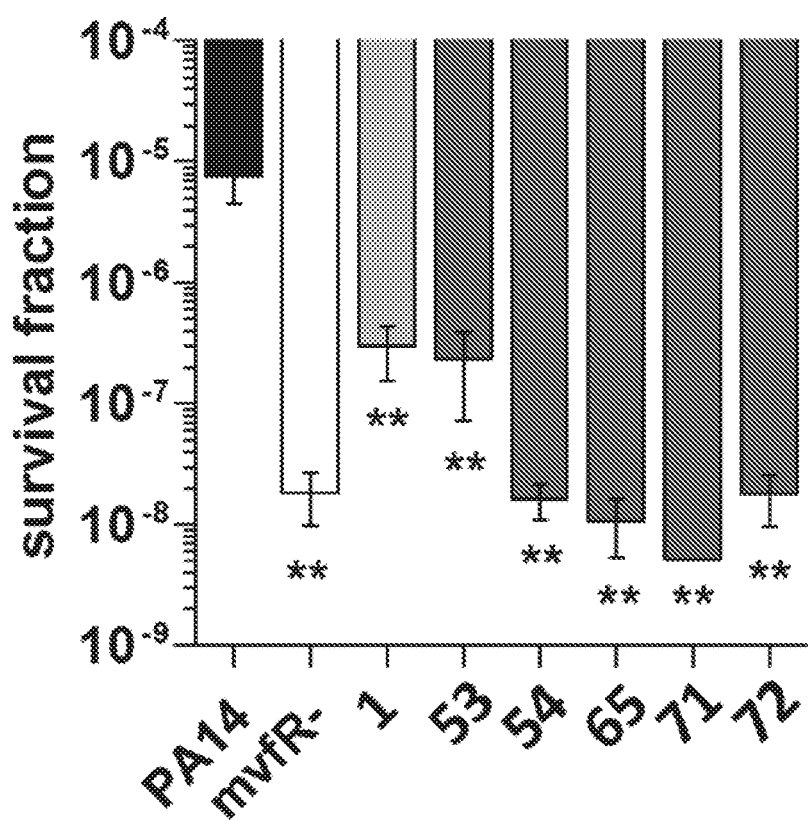
FIG. 2E shows the ability of Compounds 1, 53, 54, 65, 71, and 72 to reduce PA14 tolerance to 10 µg/mL of the antibiotic meropenem. Data are presented as Colony Forming Units (CFU) presenting the survival fraction of antibiotic tolerant/persister cells.
Figure 2F:
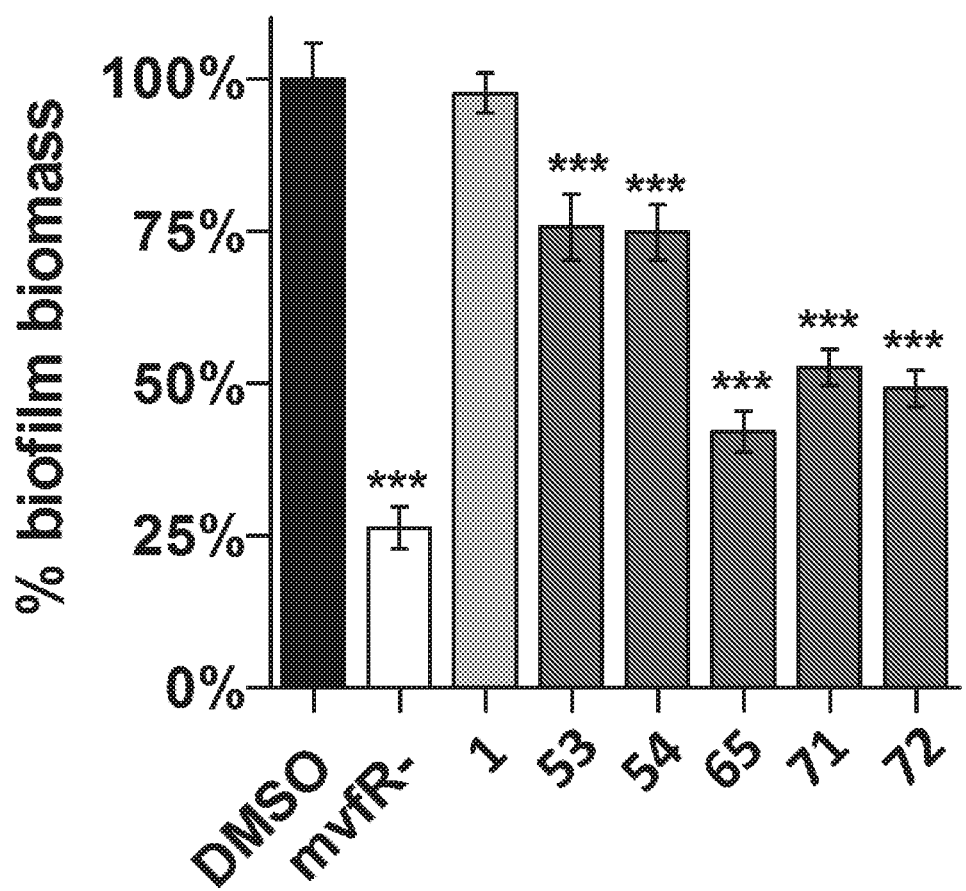
FIG. 2F shows the ability of Compounds 1, 53, 54, 65, 71, and 72 to reduce PA14 biofilm formation.
Figure 3A:
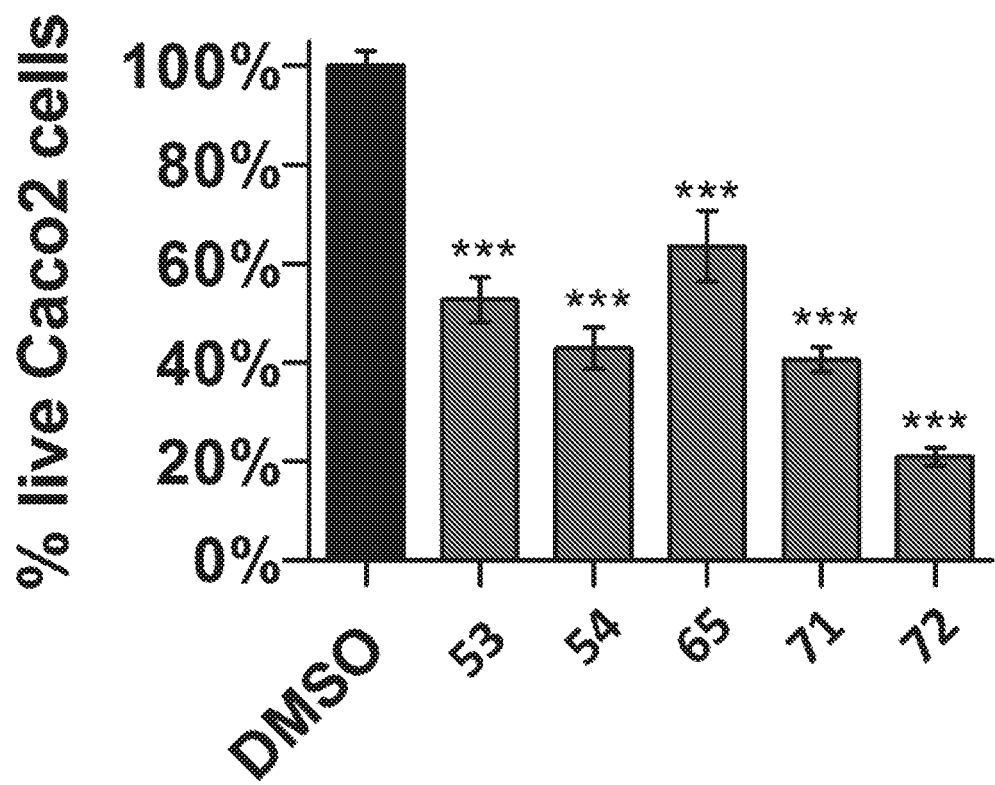
FIG. 3A shows intracellular concentration of the AIEC strain LF82 3 hours after infection of Caco2 intestinal epithelial cells, in the presence or absence of 25 µM of Compounds 53, 54, 65, 71, and 72, and vehicle (DMSO).
Figure 3B:
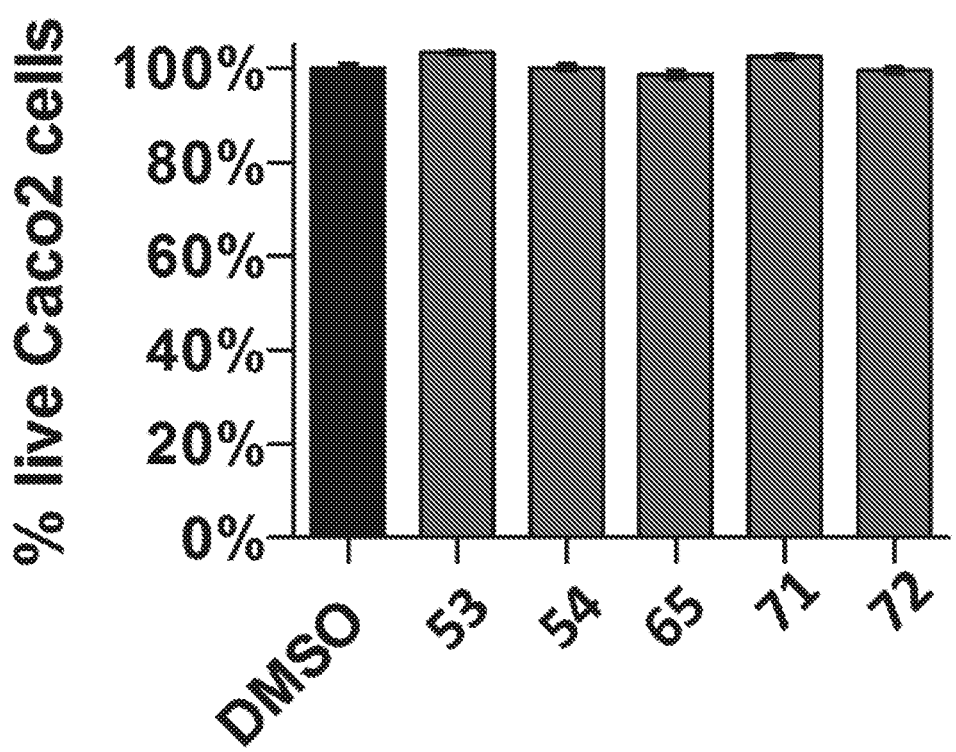
FIG. 3B shows survival of Caco2 cells after 3 hours exposure to 25 µM of Compounds 53, 54, 65, 71, and 72, and vehicle (DMSO), confirming that compounds are not toxic to Caco2.
Figure 3C:
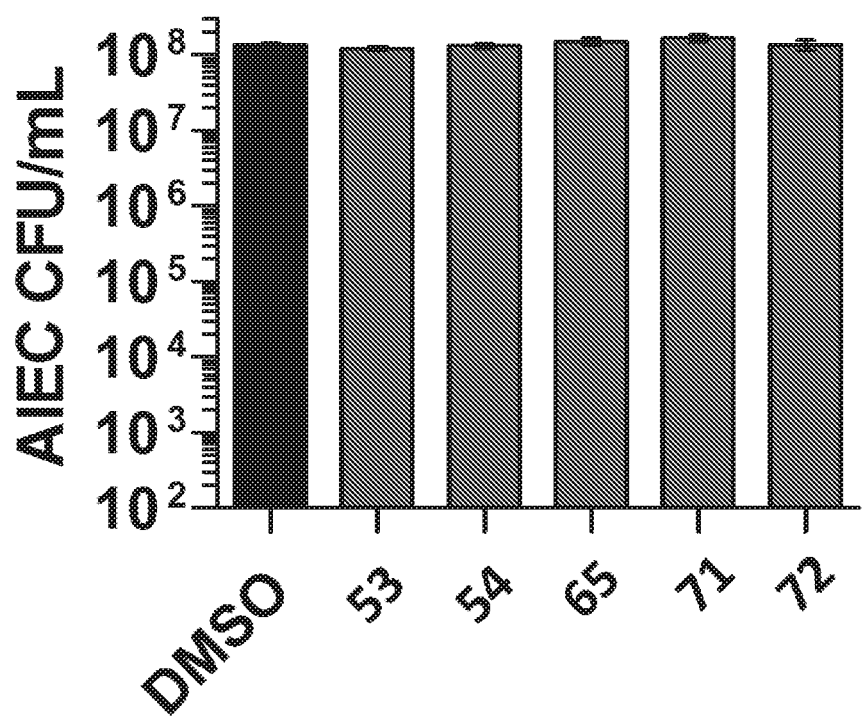
FIG. 3C shows AIEC counts after 3 hours of incubation in cell culture media in the presence of 25 µM of Compound 53, Compound 54, or vehicle (DMSO).
Figure 3D:
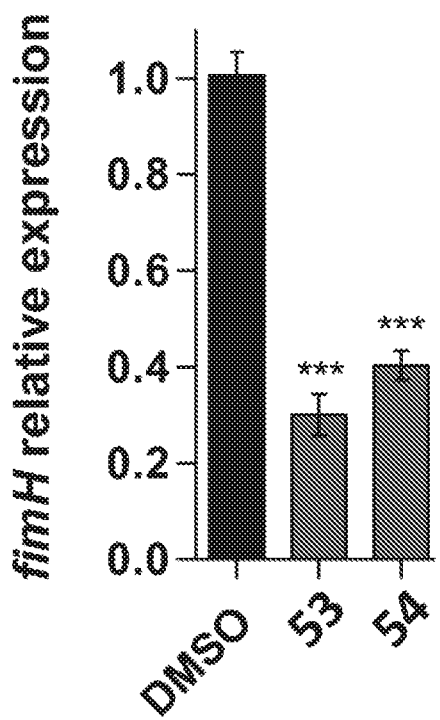
FIG. 3D shows fimH expression measured by RTqPCR in stationary phase (OD 4.8) cultures of LF82 in the presence of 50 µM of Compound 53, Compound 54, or vehicle (DMSO).
Figure 4A:
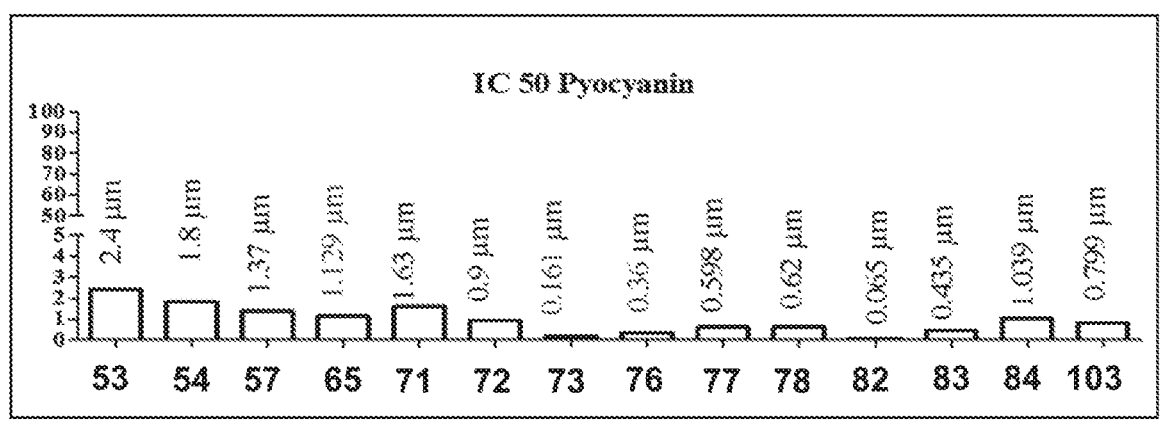
Figure 4E:
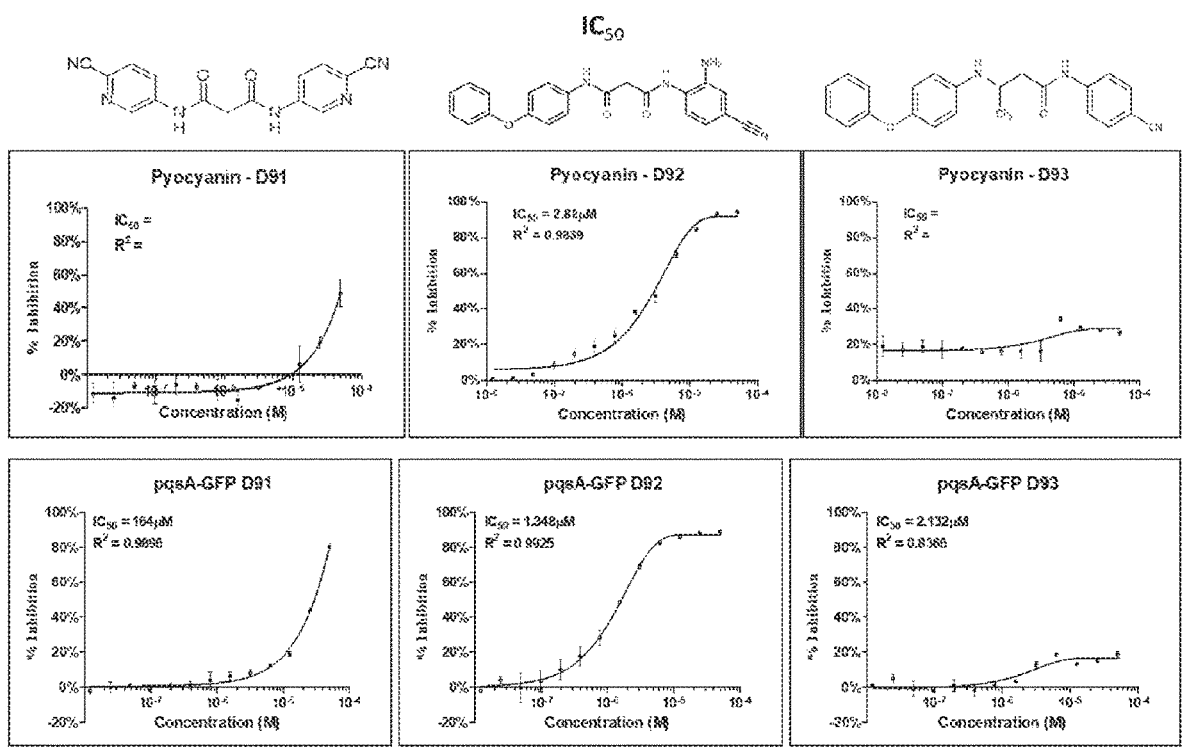
Figure 4F:
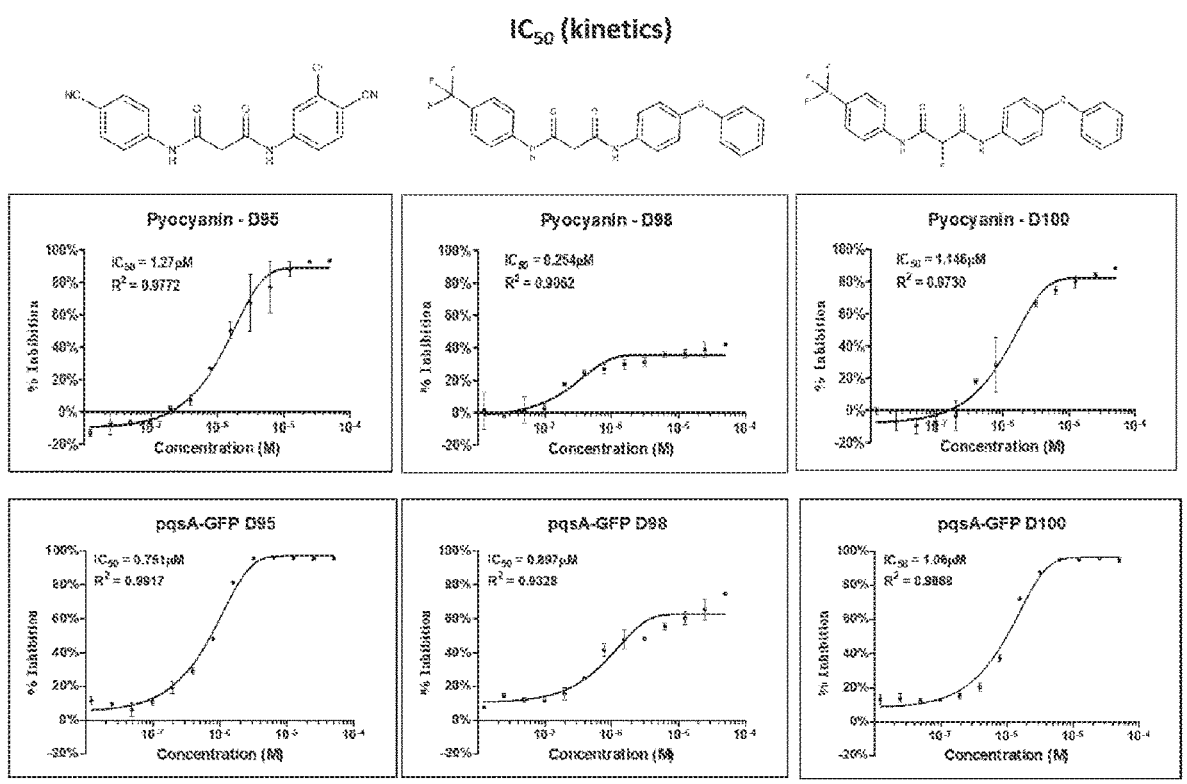
Figure 4G:
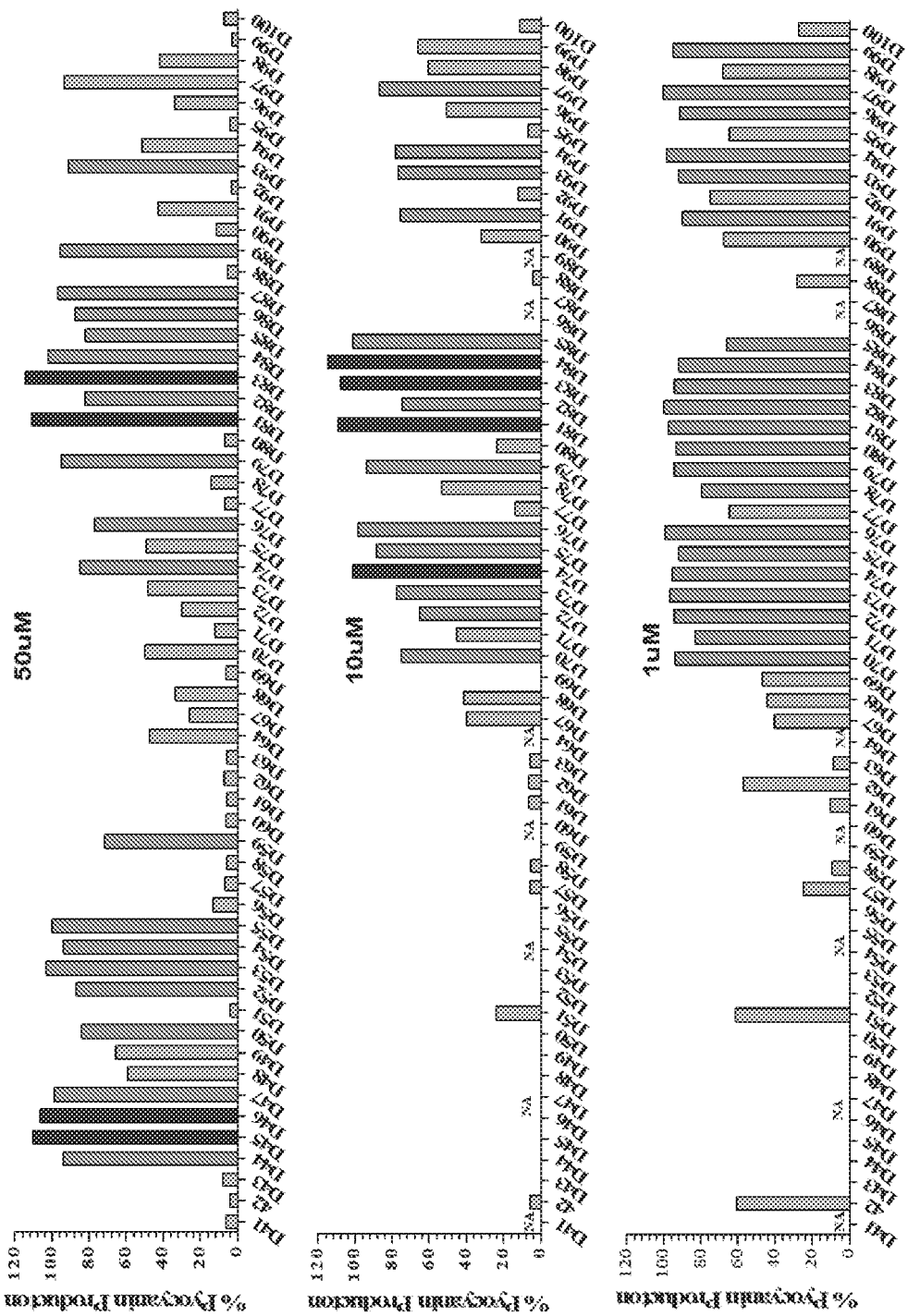

PK studies show that Compounds 53-54, and 72 are also stable in vivo, retaining a relatively high serum concentration even after 24 h, as shown in FIGS. 1F-1G. This is an additional improvement relative to potent known benzamide-benzamidazole (BB) compounds (see e.g., M64, reported in U.S. Pat. No. 8,877,940), which has much lower serum stability (half-life of 30 min).

Additional pharmacokinetic data are shown in FIGS. 6A-6E. Among the compounds evaluated, Compounds 53, 54, and 72 exhibited promising pharmacokinetics. For example, Compound 72, although not the most potent inhibitor, showed good lung exposure with a half-life of 1.19 hours and plasma a half-life of 1.13 h and $T_{last}$ of ~6 h. The PK profile of Compound 72 is therefore suitable for subcutaneous (SC) administration and would allow sufficient level for efficacy study alone and/or in combination with a selected antibiotic (e.g., ciprofloxacin).

Example 2. Screening Assays

Experiments were performed to identify compounds that inhibit the MvfR regulon without altering growth, ultimately attenuating *P. aeruginosa* infection. MvfR is a LysR-type transcriptional regulator that directs HAQs synthesis, including that of its ligands, 4-hydroxy-2-heptylquinoline (HHQ) and 3,4-dihydroxy-2-heptylquinoline (PQS). MvfR regulates the production of many virulence factors including pyocyanin, elastase, and lectins as well as a myriad of low molecular weight molecules; and both MvfR and PQS have been demonstrated as essential for pathogenesis in several host models.

MvfR promotes the production of HAQs by binding to and activating the pqs operon, which encodes enzymes for HAQ synthesis. Anthranilic acid (AA), derived from the phnAB, kynABU, and trpEG pathways, is the precursor for HAQs. pqsA encodes an anthranilate-coenzyme A ligase, which activates anthranilic acid and catalyzes the first committed step to HAQ production. The exact roles of PqsB and PqsC are unknown, though both show homology to acyl-carrier-proteins and both are required for HHQ and PQS production. PqsD is a condensing enzyme that along with PqsA has been shown to be necessary and sufficient for the production of 2,4-dihydroxyquinoline (DHQ), a molecule whose biological role has yet to be determined. The final gene of the operon, pqsE encodes for a putative hydrolase, and while the protein is not required for the synthesis of HAQs, it is necessary for pyocyanin production.

Bacterial Strains and Growth Conditions

PA14 is the wild-type *P. aeruginosa* strain. *Burkholderia thailandensis* is closely related to *Burkholderia pseudomallei*. All strains were routinely cultured in LB at 37° C., with antibiotics where necessary: 75 μg/mL tetracycline, 100 μg/mL rifampicin, and 300 μg/mL carbenicillin.

Quantification of Pyocyanin

Pyocyanin levels were determined by measuring $OD_{520nm}$ of chloroform-extracted cultures.

Quantification of Antibiotic Tolerance/Persister Cell Formation

AT/P efficacy of compounds using CFU plating was assessed by growning over-night, cultures diluted 1:100 in triplicate in fresh LB medium in the presence or absence of inhibitor, and re-grown to an OD600 of 2.0 while shaking under aeration at 37° C. Before the antibiotic treatment, aliquots were plated to obtain reference colony counts. The cultures were then treated with 10 mg/L of meropenem (100× of MIC), a beta-lactam representative, and incubated at 37° C. for 48 h while shaking under aeration. At 24-h and 48-h time points, the number of surviving bacteria were assessed by plating. The survival fraction of AT/P cells was calculated by dividing the number of surviving bacteria by the number of live bacteria that were present before the antibiotic treatment (reference datum) and expressed as a mean (±SD) of at least three replicate experiments. Using the same CFU plating assay, the efficacy of all compounds identified will be tested against additional antibiotic classes: b-lactams (ceftazidime, cefepime and imipenem), quinolones (ciprofloxacin, moxifloxacin, and levofloxacin), and aminoglycosides (gentamicin and tobramycicn). The surviving cells were confirmed to be truly antibiotic tolerant and not resistant mutants; this tolerance characteristic was demonstrated as above by their unchanged minimal inhibitory concentrations (MICs) and by repetition of the killing curve for a culture inoculated from single surviving colonies, which further confirms that the surviving cells are not antibiotic resistant.

LC/MS Analyses for Hydroxy-2-Alkylquinoline (HAQ) Determination

The quantification of HAQs in bacterial culture supernatants was performed. The HAQs were separated on a C18 reverse-phase column connected to a triple quadrupole mass spectrometer, using a water/acetonitrile gradient. Positive electrospray in MRM mode with $2\times10^{-3}$ mTorr argon and 30 V as the collision gas and energy was employed to quantify HAQs, using the ion transitions HHQ 244>159, HHQ-D4 248>163, HQNO 260>159, PQS 260>175, and PQS-D4 264>179. B. thailandensis HAQs were assessed as above. The pseudomolecular ions of each compound were monitored in full scan mode, using the unsaturated PA14 HAQ response factors.

Compounds were tested at various concentrations and the resulting data are shown below in Tables 2A-2C and FIGS. 1A-1C, 2A-2C, and 4A-4D.

TABLE 2A

| Code | pyocyanin @50 uM (%) | pyocyanin @10 uM (%) | pyocyanin @1 uM (%) | pqsA @50 uM (%) | pqsA @10 uM (%) | HHQ @50 uM (%) | PQS @50 uM (%) | HQNO @50 uM (%) |
|---|---|---|---|---|---|---|---|---|
| M17 | 66.83 | | | 32.40 | | 2.67 | 10.50 | 17.00 |
| G1 | 102.49 | | | 84.13 | | 100.33 | 109.47 | 101.44 |
| G2 | 60.90 | | | 46.00 | | 109.69 | 93.37 | 86.47 |
| G3 | 113.18 | | | 95.86 | | 99.15 | 121.58 | 110.82 |
| G4 | 83.60 | | | 92.00 | | 94.57 | 88.49 | 92.31 |
| G5 | 98.40 | | | 98.00 | | 113.88 | 113.88 | 111.41 |
| G6 | 110.20 | | | 86.84 | | 105.67 | 115.29 | 130.73 |
| G7 | 91.10 | | | 78.00 | | 83.49 | 94.72 | 93.96 |
| G8 | 85.57 | | | 63.23 | | 87.13 | 123.87 | 107.69 |
| G9 | 94.30 | | | 92.90 | | 76.37 | 123.85 | 92.49 |
| G10 | | | | | | | | |
| G11 | 96.00 | | | 95.66 | | 73.39 | 95.55 | 91.21 |
| D1 | 101.56 | | | 88.58 | | | | |
| D2 | 100.78 | | | 96.21 | | | | |
| D3 | 97.28 | | | 92.02 | | | | |
| D4 | 89.11 | | | 56.31 | | | | |
| D5 | 102.33 | | | 99.75 | | | | |
| D6 | 91.26 | | | 68.00 | | | | |
| D7 | 88.72 | | | 70.02 | | | | |
| D8 | 101.95 | | | 97.71 | | | | |
| D9 | 106.61 | | | 104.64 | | | | |
| D10 | 89.88 | | | 89.18 | | | | |
| D11 | 101.17 | | | 97.01 | | | | |
| D12 | 107.78 | | | 92.27 | | | | |
| D13 | 100.39 | | | 90.17 | | | | |
| D14 | 85.21 | | | 76.51 | | | | |
| D15 | 101.95 | | | 86.93 | | | | |
| D16 | 43.19 | | | 17.71 | | | | |
| D17 | 109.73 | | | 70.02 | | | | |
| D18 | 68.48 | | | 28.05 | | | | |
| D19 | 108.95 | | | 99.80 | | | | |
| D20 | 111.28 | | | 88.03 | | | | |
| D21 | 112.45 | | | 87.28 | | | | |
| D22 | 96.11 | | | 70.87 | | | | |
| D23 | 107.39 | | | 92.47 | | | | |
| D24 | 59.14 | | | 25.50 | | | | |
| D25 | 97.28 | | | 83.99 | | | | |
| D26 | 102.33 | | | 95.41 | | | | |
| D27 | 93.39 | | | 99.55 | | | | |
| D28 | 59.53 | | | 42.02 | | | | |
| D29 | 94.55 | | | 92.77 | | | | |
| D30 | 91.44 | | | 94.16 | | | | |
| D31 | 68.48 | | | 47.01 | | | | |

TABLE 2A-continued

| Code | pyocyanin @50 uM (%) | pyocyanin @10 uM (%) | pyocyanin @1 uM (%) | pqsA @50 uM (%) | pqsA @10 uM (%) | HHQ @50 uM (%) | PQS @50 uM (%) | HQNO @50 uM (%) |
|---|---|---|---|---|---|---|---|---|
| D32 | 92.22 | | | 93.67 | | | | |
| D33 | 59.14 | | | 52.77 | | | | |
| D34 | 90.78 | | | 79.63 | | 96.98 | 97.16 | 95.77 |
| D35 | 88.27 | | | 74.30 | | 109.39 | 108.28 | 100.62 |
| D36 | 15.70 | | | 9.70 | | 56.80 | 46.73 | 58.50 |
| D37 | 106.32 | | | 96.88 | | 97.87 | 110.42 | 99.47 |
| D38 | 107.9 | | | 89.9 | | 98.46 | 96.13 | 100.47 |
| D39 | 109.9 | | | 91.4 | | 96.24 | 93.47 | 101.84 |
| D40 | 114.6 | | | 95.7 | | 102.42 | 99.76 | 108.72 |
| D41 | 6.23 | | | 7.97 | 1.55 | 1.63 | 8.37 | 13.87 |
| D42 | 5.70 | 5.9 | 60.8 | 7.93 | 8.80 | 1.76 | 7.40 | 12.50 |
| D42 Br1 | 86.26 | 70.65 | 99.02 | | 94.04 | | | |
| D42 Br2 | 17.17 | 41.38 | 79.91 | | 64.23 | | | |
| D43 | 8.07 | | | 8.30 | | 18.13 | 22.33 | 36 |
| D44 | 94.03 | | | 70.67 | 11.04 | 77.77 | 85.13 | 85.93 |
| D45 | 110.13 | | | 105.40 | 110.20 | 75.93 | 86.57 | 85.33 |
| D46 | 106.23 | | | 80.67 | 117.22 | 66.57 | 83.60 | 77.03 |
| D47 | 99.03 | | | 77.77 | 112.19 | 79.03 | 87.20 | 85.47 |
| D48 | 59.47 | | | 43.57 | 109.74 | 79.63 | 83.47 | 86.47 |
| D49 | 65.60 | | | 28.03 | 86.55 | 119.56 | 118.59 | 100.65 |
| D50 | 83.98 | | | 101.93 | 107.09 | 106.53 | 103.53 | 102.58 |
| D51 | 3.40 | 29.70 | 80.30 | 9.50 | | 2.88 | 6.32 | 18.38 |
| D51P | 4.00 | 24.86 | 61.28 | | 1.51 | | | |
| D52 | 87.20 | | | 89.70 | 97.91 | 92.35 | 86.36 | 91.69 |
| D53 | 103.13 | | | 84.85 | 94.22 | 74.65 | 87.63 | 84.58 |
| D54 | 93.85 | | | 84.92 | 94.22 | 103.31 | 100.80 | 101.24 |
| D55 | 99.70 | | | 131 | 94.65 | 130.33 | 115.26 | 98.35 |
| D56 | 13.33 | | | 6.03 | 13.32 | | | |
| D57 | 6.06 | 16.79 | 14.01 | 3.70 | 1.08 | | | |
| D58 | 5.90 | 5.20 | 9.20 | 8.90 | 1.95 | | | |
| D59 | 71.80 | | | 81.20 | 86.05 | | | |
| D60 | 6.13 | | | | 9.83 | | | |
| D61 | 5.60 | 6.17 | 10.50 | 6.70 | 10.04 | | | |
| D62 | 7.30 | 6.17 | 57.50 | 6.20 | 1.51 | | | |
| D63 | 5.90 | 5.73 | 8.80 | 7.30 | 9.63 | | | |
| D64 | 47.70 | | | 60.50 | 64.54 | | | |
| D65 | | | | | | | | |
| D66 | | | | | | | | |
| D67 | 25.97 | 39.88 | 40.28 | | 28.79 | | | |
| D68 | 33.47 | 41.34 | 44.67 | | 27.71 | | | |
| D69 | 6.1 | 6.98 | 46.77 | | 6.98 | | | |
| D70 | 49.7 | 75.35 | 93.97 | | 84.81 | | | |
| D71 | 12.5 | 45.44 | 83.17 | | 59.82 | | | |
| D72 | 30.2 | 65.45 | 94.59 | | 77.76 | | | |
| D73 | 48.3 | 77.66 | 96.99 | | 95.07 | | | |
| D74 | 84.8 | 101.70 | 95.65 | | 98.46 | | | |
| D75 | 49.4 | 88.45 | 91.79 | | 97.18 | | | |
| D76 | 77.1 | 98.27 | 99.21 | | 87.37 | | | |
| D77 | 6.8 | 13.89 | 64.55 | | 25.42 | | | |
| D78 | 14.3 | 53.45 | 79.61 | | 61.29 | | | |
| D79 | 95.2 | 93.97 | 94.60 | | 108.72 | | | |
| D80 | 7.0 | 23.88 | 93.49 | | 45.72 | | | |
| D81 | 110.9 | 109.28 | 97.35 | | 118.14 | | | |
| D82 | 82.3 | 74.50 | 99.89 | | 99.74 | | | |
| D83 | 114.1 | 107.70 | 94.54 | | 113.65 | | | |
| D84 | 102.0 | 114.90 | 92.01 | | 96.30 | | | |
| D85 | 81.9 | 101.34 | 66.29 | | 88.94 | | | |
| D86 | 87.8 | | | | 96.31 | | | |
| D87 | 96.77 | | | | 93.42 | | | |
| D88 | 5.58 | 4.40 | 28.11 | | 1.95 | | | |
| D89 | 95.26 | | | | 97.30 | | | |
| D90 | 11.37 | 31.97 | 67.97 | | 47.33 | | | |
| D91 | 43.10 | 75.63 | 89.95 | 38.94 | 80.00 | | | |
| D92 | 3.51 | 12.09 | 75.00 | 1.40 | 2.10 | | | |
| D93 | 90.98 | 76.84 | 91.89 | 88.42 | 87.01 | | | |
| D94 | 51.50 | 78.21 | 98.57 | 84.94 | 87.01 | | | |
| D95 | 4.12 | 6.80 | 64.69 | 5.61 | 1.75 | | | |
| D96 | 34.03 | 50.77 | 91.68 | 41.75 | 62.80 | | | |
| D97 | 93.60 | 87.06 | 100.66 | 95.08 | 95.43 | | | |
| D98 | 42.10 | 60.94 | 68.03 | 28.77 | 37.19 | | | |
| D99 | 2.85 | 66.14 | 94.86 | 1.75 | 58.94 | | | |
| D100 | 7.08 | 11.42 | 27.05 | 1.75 | 1.05 | | | |

TABLE 2B

| Compound No. | Code | 2-AA @50 uM | DHQ @50 uM | AA @50 uM |
|---|---|---|---|---|
| 1 | M17 | 100.63% | 135.40% | 100.33% |
| 2 | G1 | 122.46% | | |
| 3 | G2 | 68.29% | 81.45% | |
| 4 | G3 | 122.73% | | |
| 5 | G4 | 80.36% | 84.71% | |
| 6 | G5 | 63.36% | 82.65% | |
| 7 | G6 | 152.45% | | |
| 8 | G7 | 71.65% | 67.84% | |
| 9 | G8 | 112.30% | | |
| 10 | G9 | 63.85% | 59.49% | |
| 12 | G11 | 63.08% | 51.45% | |
| 46 | D34 | 112.66% | 99.54% | 101.21% |
| 47 | D35 | 100.05% | 99.35% | 129.08% |
| 48 | D36 | 37.27% | 68.30% | 186.73% |
| 49 | D37 | 103.09% | 105.43% | 89.75% |
| 50 | D38 | 101.29% | 84.18% | 54.49% |
| 51 | D39 | 106.00% | 95.53% | 68.03% |
| 52 | D40 | 112.79% | 84.88% | 80.69% |
| 53 | D41 | 5.87% | 10.30% | 738.77% |
| 54 | D42 | 5.63% | 10.63% | 700.80% |
| 57 | D43 | 19.97% | 31.90% | 530.90% |
| 58 | D44 | 86.63% | 89.80% | 32.27% |
| 59 | D45 | 97.26% | 90.96% | 35.47% |
| 60 | D46 | 104.27% | 82.87% | 28.17% |
| 61 | D47 | 93.60% | 93.03% | 42.40% |
| 62 | D48 | 72.70% | 84.70% | 58.70% |
| 63 | D49 | 89.91% | 106.35% | 130.61% |
| 64 | D50 | 140.26% | 88.82% | 176.02% |
| 65 | D51 | 6.94% | 12.28% | 2629% |
| 67 | D52 | 100.92% | 103.07% | 115.09% |
| 68 | D53 | 92.75% | 98.21% | 55.95% |
| 69 | D54 | 117.10% | 107.75% | 82.43% |
| 70 | D55 | 94.75% | 80.05% | 117.29% |

TABLE 2C

| Compound No. | Code | $IC_{50}$ pyocyanin (μM) | $IC_{50}$ pqsA (μM) | $IC_{50}$ HHQ (μM) | $IC_{50}$ PQS (μM) | $IC_{50}$ HQNO (μM) | $IC_{50}$ 2-AA (μM) | $IC_{50}$ DHQ (μM) | $IC_{50}$ AA (increase; μM) |
|---|---|---|---|---|---|---|---|---|---|
| 1 | M17 | 70.6 | 20.2 | 10.4 | 15.1 | 20.3 | | | |
| 28 | D16 | 20.4 | 24.6 | | | | | | |
| 48 | D36 | 7.1 | 5.5 | 47.5 | 36.5 | 33.7 | 20.9 | 33.0 | 42.5* |
| 53 | D41 | 2.4 | 1.25 | 10.3 | 8.3 | 7.3 | 5.6 | 9.1 | 14.5* |
| 54 | D42 | 1.8 | 1.28 | 11.2 | 7.8 | 8.7 | 4.7 | 10.1 | 11.3* |
| 57 | D43 | 1.37 | 0.94 | | | | | | |
| 63 | D49 | | 57.08 | | | | | | |
| 65 | D51 | 4.48 | 2.54 | 21.21 | 23.02 | 23.29 | 8.95 | 11.31 | 33.98* |
| 66 | D51P | 0.84 | | | | | | | |
| 71 | D56 | 1.63 | 0.72 | | | | | | |
| 72 | D57 | 0.891 | 0.52 | | | | | | |
| 73 | D58 | 0.398 | 0.21 | | | | | | |
| 76 | D61 | 0.368 | 0.42 | | | | | | |
| 78 | D63 | 0.618 | 0.938 | | | | | | |
| 82 | D67 | 0.09 | | | | | | | |
| 83 | D68 | 0.83 | | | | | | | |
| 84 | D69 | 0.45 | | | | | | | |
| 86 | D71 | 1.54 | | | | | | | |
| 92 | D77 | 1.61 | | | | | | | |
| 95 | D80 | 1.35 | | | | | | | |
| 103 | D88 | 0.95 | | | | | | | |
| 105 | D90 | 2.78 | | | | | | | |

Compounds identified to interfere with MvfR were confirmed for the direct physical interaction with this protein. Using SPR, the percentage of compound's binding to the purified MvfR protein was analyzed and used to determine the binding parameters ($K_D$, $k_{on}$ and $k_{off}$)—thus determining the kinetic of interaction with MvfR.

The recombinant MvfR co-inducer binding domain was purified using Ni-NTA chromatography, as previously reported (see e.g., Xiao et al, *Microbiology*, 2006, 152:1679-1686; Starkey et al, *PLoS Pathog.* 2014, 10:e1004321; and Kefala et al, *Acta. Crystallogr. Sect. F. Struct. Biol. Cryst. Commun.* 2012, 68:695-697). The purified protein was immobilized with the amine coupling method at a target level of 5000 RU on Chip. SPR was performed according to previously reported procedures (see e.g., Starkey et al, *PLoS Pathog.* 2014, 10:e1004321; Maura et al, *ACS Chemical Biology,* 2017, 12:1435-1443; and Kitao et al, *MBIO,* in press). Some of the compounds (e.g. Compounds 53, 54, 57, and 71) exhibited a 40 times higher binding intensity than the parent Compound 1 with a mean $K_D$ value of ~0.25 μM. Table 3 lists the steady-state $K_D$ data measured by SPR. Even the lower binding intensity displayed by some compounds was significant, as the $K_D$ of those inhibitors is in the same order of magnitude to that of HHQ and PQS two well-established MvfR native ligands (see e.g., Starkey et al, *PLoS Pathog.* 2014, 10:e1004321; and Maura et al, *ACS Chemical Biology,* 2017, 12:1435-1443).

Example 3. Surface Plasmon Resonance (SPR)

To obtain direct demonstration of the physical interaction between inhibitor and target, an imperative and critical step in drug discovery, an assessment of the binding affinity of several compounds using surface plasmon resonance (SPR) was performed and the resulting data is shown in Table 3.

TABLE 3

| Compound | Code | Steady State Binding Affinity $K_D$ [M] | Steady State Binding Affinity $K_D$ (μM) | Signal Intensity $R_{max}$ |
|---|---|---|---|---|
| 1 | M17 | 9.19E−06 | 9.185 | 23.41 |
| 78 | D63 | 4.94E−07 | 0.494 | 34.69 |

TABLE 3-continued

| Compound | Code | Steady State Binding Affinity | | Signal Intensity |
| | | $K_D$ [M] | $K_D$ (µM) | $R_{max}$ |
| --- | --- | --- | --- | --- |
| 76 | D61 | 4.78E−07 | 0.478 | 36.46 |
| 73 | D58 | 7.55E−07 | 0.755 | 33.31 |
| 53 | D41 | 2.44E−07 | 0.244 | 26.52 |
| 54 | D42 | 2.75E−07 | 0.275 | 28.21 |
| 57 | D43 | 2.86E−07 | 0.286 | 27.05 |
| 72 | D57 | 1.09E−06 | 1.094 | 34.24 |
| 65 | D51 | 3.99E−07 | 0.399 | 29.51 |
| 71 | D56 | 2.59E−07 | 0.259 | 30.74 |

Example 4. Assessment of Early Steps of Biofilm Formation

Inhibition of biofilm formation was assessed by quantifying initiation of biofilm formation via assessment of surface adhesion of PA using the microtiter biofilm assay as described in O'Toole, G A. *J. Vis. Exp.* 2011, *Microtiter Dish Biofilm Formation Assay*. Using single optimized agents, this assay allowed for various concentrations of each compound and several incubation times to be investigated in an HTS manner. Results of the biofilm formation assays are shown in FIGS. 1I-1J and 2E-2F.

Example 5. Disruption of Preformed Biofilms

To further evaluate the utility the compounds described herein, the efficacy in disrupting established biofilms was analyzed. Biofilms were grown for 48 hours on peg lids in microtiter plates containing M63 minimal media supplemented with 0.2% glucose, 0.5% Casamino Acids, and 1 mM $MgSO_4$ as previously described (see e.g., Maura et al, *ACS Chemical Biology*, 2017, 12:1435-1443). A portion of the biofilm pegs was used for CFU counts, while the rest was incubated in the presence of 10 µM of selected molecules or vehicle control for 24 hours. For CFU counts, pegs were washed in PBS, then aseptically cut out and sonicated in the presence of PBS to detach the biofilm from pegs as described in Maura et al, *Sci. Rep.* 2016, 6:34083. Samples were then diluted and plated on agar plates to count CFUs. In addition, it was determined whether concomitant addition of compound and antibiotics would increase the antibiotic efficacy against preformed biofilms, or whether optimized compounds could only be active when added prophylactically. Biofilms were grown for 48 hours and were then simultaneously treated with 10 µM of compound and antibiotics (i.e., 10 µg/mL of Meropenem or Tobramycin) for 24 hours. Biofilms were processed as above to count CFUs, and the resulting data is shown in FIG. 1J (data for Meropenem).

Example 6. Combination Drug Assays

Using the same set-up as above we will determine whether selected optimized compounds improve antibiotic efficacy to clear biofilms. Two-drug combination assays will be set up to test potential synergism as we described in (see e.g., Maura et al, *ACS Chemical Biology*, 2017, 12:1435-144). Antibiotics of the 3 classes described above (see Example 2, *Quantification of antibiotic tolerance/persister cell formation*) will be used to compare lead molecules efficacy using the experimental set up as above.

Example 7. Assessment of Efficacy Against *P. aeruginosa* Adherent to Cystic Fibrosis Airway Cells For these experiments, CF airway cells (CFBE41o-) will be grown in multiwell plates for 7-10 days, which will allow for confluence and tight junction formation (see e.g., Anderson et al, *Infect. Immun.* 2008, 76:1423-1433). *P. aeruginosa* (PA14 and/or CF clinical isolates) will be applied to the monolayer surface (MOI 30:1) and the bacteria incubated with the monolayer for one hour to allow the bacteria to adhere. After one hour, the cells will be washed twice with media to remove the non-adherent bacteria. At this point the inhibitor will be applied at one or more concentrations (10 µM-100 µM) in conjunction with vehicle (DMSO) control, inhibitor alone, and no treatment controls, and the treatments will co-incubate for another 5 hours. The media from the coculture (PA/CF cells) experiments will be removed, centrifuged at high speed to pellet and remove any bacteria and cell debris, and used to quantify LDH release as a measurement of cytotoxicity (Cytotox 96, Promega) promoted by the adherent bacteria. In addition, the release of four cytokines will be assessed (IL-8, IL-6, CXCL1 and CXCL2 by ELISA (Promokine); see e.g., Hampton et al, *Am. J. Physiol. Lung Cell Mol. Physiol.* 2012, 303:509-518). CFU measurements can be made by washing and disrupting adherent (biofilm) bacteria using 0.1% triton X-100 to lyse the monolayer (as described in Anderson et al, *Infect. Immun.* 2008, 76:1423-1433). To diminish the possibility of off-target effects, PA14 isogenic mvfR and pqsBC mutants will be also tested in presence and absence of the inhibitors in the same setting.

Example 8. *B. thailandensis* Coculture Model of Infection

*B. thailandensis* does not elicit the significant cytotoxic effect observed with *P. aeruginosa* in the coculture biofilm model of infection so an alternative planktonic coinfection model has been developed to assess the cytoxicity promoted by this bacterium. The CFBE cells are cultured and washed as described above in Example 7. *B. thailandensis* is inoculated at an MOI of 500 and at this time the inhibitors (10 µM-100 µM) and controls are added. The *B. thailandensis* are coincubated for 9 hours, at which time inflammation and cytotoxicity markers can be assessed as described above in Example 7. Because MvfR inhibitors target a protein not present in *B. thailandensis*, these will be included as negative controls. Target specificity will be validated using an hmqBC mutant. Several clinical *Burkholderia* CF isolates will also be tested to cross validate the efficacy of the compound(s) selected.

Example 9. In Vivo Inflammation with Single and/or Combination of Inhibitors to Treat *Pseudomonas* and *Burkholderia* Infections For MvfR and PqsBC inhibitors showing positive results in the ex-vivo model of infection additional in vivo testing will be conducted using established respiratory infection model (see e.g., Starkey et al, *PLoS Pathog.* 2014, 10:e1004321). Previous work has demonstrated that treatment with either an mvfR mutant or co-administration of the MvfR benzamide-benzamidazole (BB) inhibitor M64 with PA14 cells significantly reduces mouse mortality (Id.). AB. *thailandensis* model of infection was developed that will allow for examination of the effects of the PqsBC inhibitors for this pathogen.

Example 10. Acute Mouse Respiratory Infection Model

Mice were anesthetized with a combination of xylazine and ketamine. The anesthetized mice were inoculated with 5×10⁶ CFU PA14 and/or 2×10⁷ CFU *B. thailandensis* in 40 µL of 10 mM MgSO$_4$ directly introduced into the nares with a micropipette as described previously (Id.). Mice received daily subcutaneous injections of the inhibitor(s) at a concentration of 10 mg/kg. Groups include; 1) *P. aeruginosa* with vehicle (control); 2) *B. thailandensis* with vehicle (control); 3) *B. thailandensis* and *P. aeruginosa* with vehicle (control); 4) *P. aeruginosa* with inhibitors combination; 5) *B. thailandensis* with inhibitors combination; 6) *B. thailandensis* and *P. aeruginosa* with inhibitors combination; and 7) inhibitors combination alone (control). Mice were sacrificed at 48 h post infection, lungs were extracted, weighed, CFUs will be measured using selective media and representative data is shown in FIG. 1E (Groups shown include; 1) *P. aeruginosa* with vehicle (control); and 2) *P. aeruginosa* with inhibitors combination). For each bacterium and neutrophil, recruitment to the lungs will be assessed by myeloperoxidase assay (see e.g., Pulli et al, *PLOS One*, 2013, 8). Serum cytokines will be measured by ELISA (Promokine).

Example 11. Preventing Persistence in a Relapsing Lung Infection Model

A relapsing infection model has previously been developed to examine persistence with the benzamide-benzamidazole (BB) inhibitor, M64, in combination with an antibiotic (see e.g., Starkey et al, *PLoS Pathog.* 2014, 10:e1004321). To model relapsing lung infection, mice will be immunocompromised with cyclophosphamide (100 mg/kg days −4, −1, +2) to prevent premature clearance of the bacterial infection. The mice will be anesthetized with a combination of xylazine and ketamine. The anesthetized mice will be inoculated with 1×10⁶ CFU PA14 in 40 µL of 10 mM MgSO$_4$ directly introduced into the nares with a micropipette using reported procedures (Id.). Mice will receive intravenous ciprofloxacin (10 mg/kg) for four days, or until no CFUs are detected, and subcutaneous injections of the inhibitors (10 mg/kg) or vehicle for six days. Two groups will be used, with the first group receiving inhibitors and ciprofloxacin, and the second group ciprofloxacin and vehicle control group. CFU plating and histopathology will be performed 1, 3, 5, 10 and 14 days post infection. MIC assays will be performed on isolates to confirm that relapsing infection is caused by AT/P cells and not antibiotic resistant cells using previously reported techniques (Id.)

Example 12. Rat Chronic Lung Infection Model

*P. aeruginosa* cells are imbedded in agar beads to retain the bacteria physically into the airways and create an environment that mimics bacterial biofilms and microaerobiosis present in the CF lung, leading to long lasting infection and persistent stimulation of host defenses typical of CF (see e.g., Kukavica-Ibrulj et al, *Methods Mol. Biol.* 2014, 1149: 757-771. This model presents the following advantages over an acute lung infection model: 1) the infection lasts for 15 days or longer with only a modest decline in CFUs and very low mortality rates; and 2) rodents do not need to be immunocompromised for the experiment since the agar beads prevent clearance, therefore high infectious doses can be used to sustain long-term infection.

Briefly, CD male rats (225 g) will be anesthetized and infected with 1×10⁶ cells of Xen41, a bioluminescent strain of *P. aeruginosa*, and will be embedded in agar beads (see e.g., Vogt et al, *Infect. Immun.* 2011, 79:4094-4104). If necessary, mutants of mvfR and pqsBC will be used as negative controls. Rats will receive subcutaneous injections of the inhibitors at a dosing that will be determined by PK studies (e.g., 10 mg/kg twice daily). Groups will include; 1) *P. aeruginosa* infected and inhibitor treatment; 2) *P. aeruginosa* infected and vehicle treatment (control); 3) Uninfected and inhibitor treatment (control); and 4) Uninfected and vehicle treatment (control). During the 15-day assessment period, body weight, body temperature, and clinical score will be measured. Macroscopic examination of lungs, ex vivo lung bioluminescence (IVIS imaging system, Perkin Elmer) and CFUs from lungs, trachea, and blood will be assessed upon sacrifice 15 days post infection by homogenization and plating of excised tissues. From infected tissues leukocytes cells will be measured flow cytometry, cytokines analysis (IL-1β, 17a, INF-γ, TNF-α, CINC-1) will be measured by ELISA, and histopathology will be analyzed.

Example 13. Thigh Infection Studies

Thigh infection studies were performed using Compounds 54 and 72. The resulting data indicated that these inhibitors reduced bacterial CFUs. Significant reductions in bacterial load were observed at the site of infection in both thigh (FIG. 5A) and lung (FIG. 5D) respectively in monotherapy, or in combination with ciprofloxacin. Further, Compound 72 potentiated ciprofloxacin efficacy in reducing PA cells dissemination in spleen and liver, a significant problem in human *P. aeruginosa* infections, as shown in FIGS. 5B-5C).

Example 14. Animal Burn Experiments

All mice were anesthetized using one 500 µL intraperitoneal (IP) injection of ketamine (87 mg/kg) and xylazine (13 mg/kg) in normal saline and the dorsal fur was subsequently removed with an electric clipper. A 30% total body surface area (TBSA) dorsal burn was induced by immersion in 90° C. water for 8 seconds, using a polystyrene foam template, as in the well-established burn model, with some modifications (see e.g., Walker & Mason, *J. Trauma*, 1968, 8(6):1049-1051).

Spinal protection from the thermal injury was achieved by a dorsal subcutaneous injection of 500 µL Normal Saline (N/S), prior to the induction of the burn injury. Fluid resuscitation and pain prevention following burn were achieved by a 100 µL subcutaneous injection of buprenorphine in N/S (0.3 mg/mL), in a non-burnt area. Sham animals underwent all procedures except for the thermal injury.

Immediately after burn, 100 µL of 10 mM MgSO$_4$ containing approximately 5×10⁵ CFUs of *P. aeruginosa* clinical isolate PA14 culture, or isogenic mvfR mutant culture, were intradermally injected at the burn eschar of mice in the burn plus infection (BI) group. Mice in the sham and burn alone groups received an equivalent injection of 100 µL phosphate-buffered saline (PBS). After the experiment, all animals were returned to their cages to allow recovery from anesthesia. During this period, all cages were kept on heating pads to prevent hypothermia. Food and hydrogel on the cage floor were provided ad libitum.

Example 15. In Vivo Intestinal Permeability Assay

For the assessment of the intestinal barrier function, 4 hours prior to euthanasia, mice were gavaged with 0.2 mL of Fluorescein Isothiocyanate-Dextran (FITC-Dextran) (Sigma, 3-5 kDa, product number: FD4, FIG. 7, or Sigma, 20 kDa, product number FD20S, FIG. 8) in PBS, so that a dose of 440 mg/kg body weight was achieved. 18-20 hours post BI, mice were once again anesthetized with an IP injection of 500 μL of ketamine/xylazine in normal saline as above and were euthanized by cervical dislocation. Aseptic cardiac puncture was performed to obtain blood samples. The collected blood was kept on ice and then centrifuged at 15,000 RPM for 10 minutes. The serum was removed and was used to assess the FITC levels with fluorescent spectrophotometry (excitation: 480 nm and emission: 520 nm). Mice used to assess the intestinal permeability changes over time were sacrificed with the same procedure at 4, 10 and 18 hours post BI (see FIG. 7).

Figure 7:
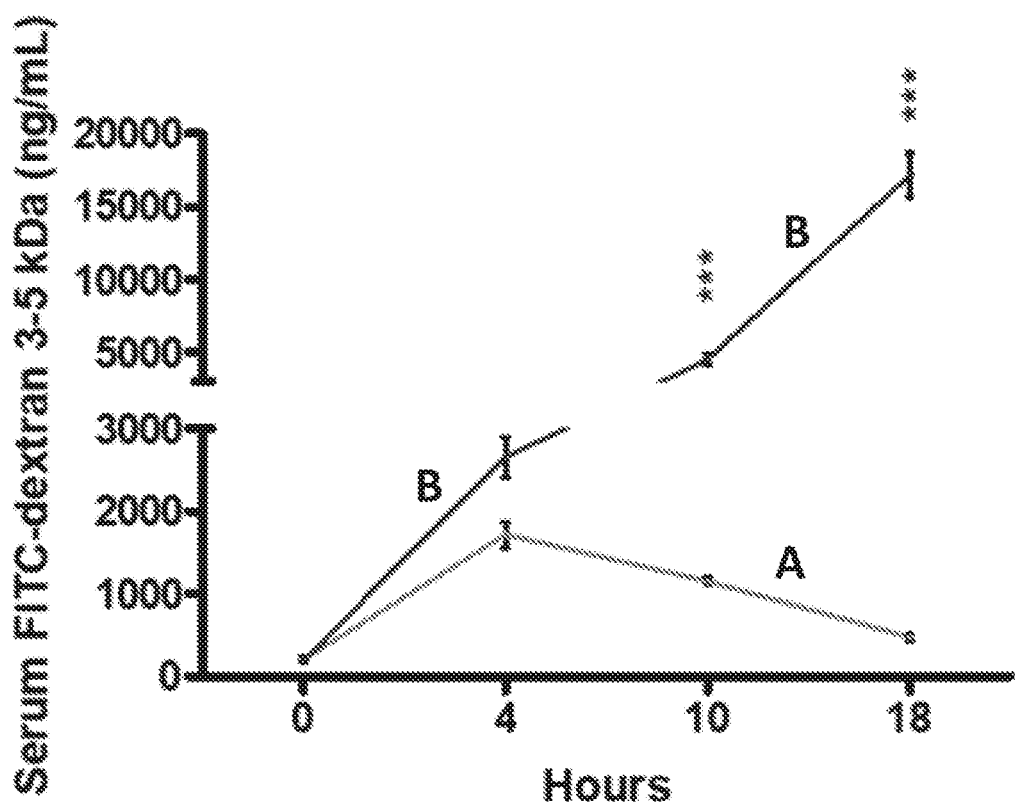
FIG. 7 shows that P. aeruginosa infection increases intestinal permeability following burn and infection. Mice were burnt ("A"-trace) or burnt and infected with P. aeruginosa strain PA14 ("B"-trace). FITC-dextran 3-5 kDa flow from the intestinal lumen to the systemic circulation increased following burn alone, with a peak at 4 hours, reaching 1,700 ng/mL and a gradual drop thereafter. FITC levels following burn plus infection (BI) showed a continuous rise and reached a concentration of over 17,000 ng/mL at 18 hours following insult. The difference between the two groups became statistically significant at 10 hours (P<0.001) and further increased at 18 hours (P<0.001). PA14 burn-site infection was induced by intradermal administration of $5 \times 10^5$ CFUs/animal. FITC-dextran 3-5 kDa levels were assessed in the serum with fluorescent spectrophotometry (excitation: 480 nm and emission: 520 nm). Data show the average+/−SEM (n=5). Statistical significance was assessed using two-way ANOVA+Bonferroni correction. FITC-dextran=Fluorescein Isothiocyanate-Dextran.

Using a burn mouse model, the intestinal permeability of mice following burn, or burn plus *P. aeruginosa* infection (burn-infection, BI), at several time points, by assessing FITC-dextran 3-5 kDa flux from the intestinal lumen to the systemic circulation was assessed. FIG. 7 shows that gut permeability increased over time, reaching a peak of 1,714 ng/mL at 4 hours following the induction of thermal injury, and then gradually returns to almost sham levels (472 ng/mL) by 18 hours. However, mice that underwent post-burn infection with the *P. aeruginosa* clinical isolate PA14 exhibited a dramatically increased intestinal permeability compared to burn alone, thus, allowing larger volumes of FITC to flow out of the intestine (4,539 ng/mL in BI versus 1,151 ng/mL in burn alone at 10 hours following injury; P<0.001). Furthermore, BI mice exhibited a prolonged rise in gut permeability levels over time, with FITC concentration reaching 17,166 ng/mL by 18 hours, indicating the strong impact of infection on the intestinal barrier dysfunction.

Figure 8:
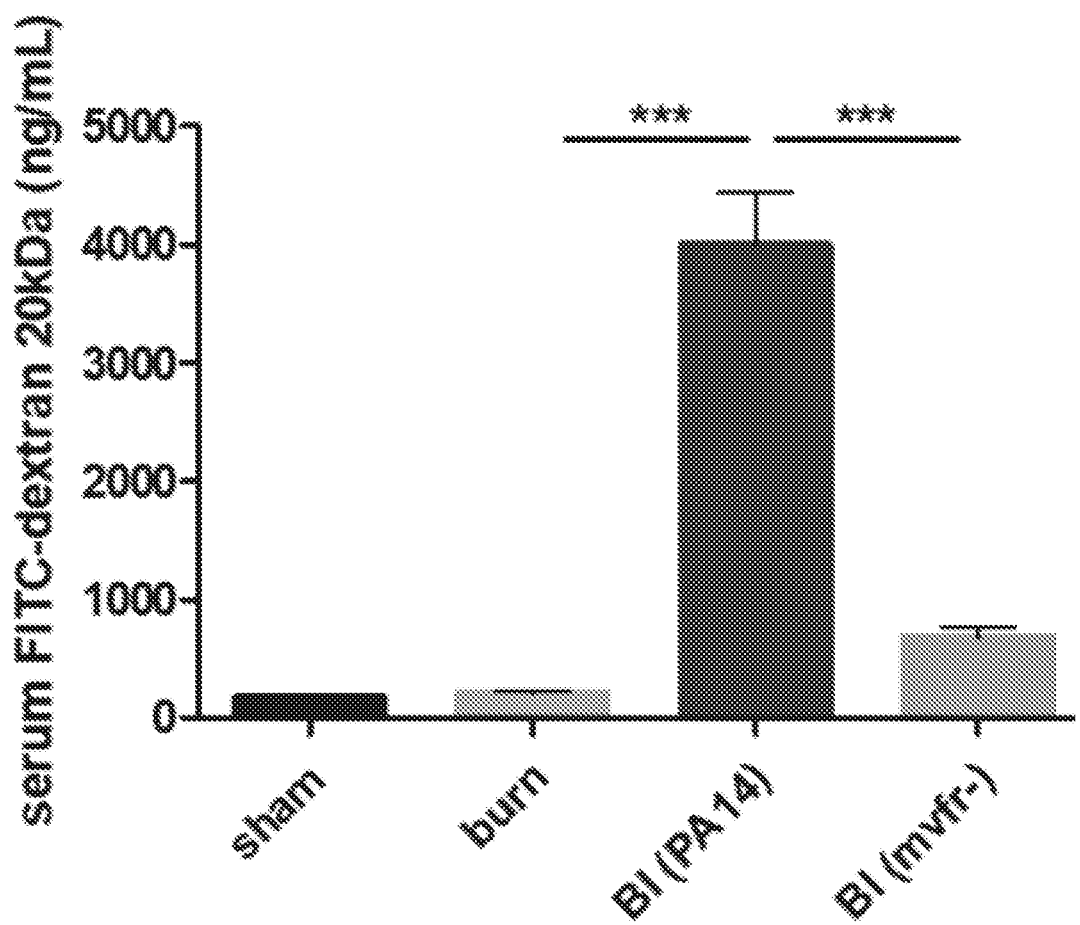
FIG. 8 shows that MvfR contributes to intestinal barrier dysfunction and increases the flow from the intestinal lumen to the systemic circulation. FITC-dextran flux out of the intestine was significantly increased in PA14 burn-site infected animals at 18 hours post burn and infection (BI), compared to sham and burn groups. MvfR isogenic mutant administration exerts reduced virulence functions and failed to substantially disrupt the intestinal barrier integrity, thus exhibiting a significantly lower level of FITC flow into the systemic circulation. FITC-dextran 20 kDa levels were assessed in the serum with fluorescent spectrophotometry (excitation: 480 nm and emission: 520 nm). PA14 burn-site infection was induced by intradermal administration of $5 \times 10^5$ CFUs/animal; Isogenic mvfr-mutant burn-site infection was induced by intradermal administration of $5 \times 10^5$ CFUs/animal. Data show the average+/−SEM (n=5). Statistical significance was assessed using one-way ANOVA+Tukey's post-hoc test. FITC-dextran=Fluorescein Isothiocyanate-Dextran.

To determine the effect of the MvfR function on the intestinal integrity, mice were infected with PA14 or the isogenic mvfR mutant, which have previously reported exerts reduced virulence (see e.g., Deziel et al, *Mol. Microbiol.* 2005, 55(4):998-1014). The FITC flux out of the intestine was assessed at 18-20 hours, when the burn impact on gut permeability largely returned to the level of the sham animals, as shown in FIG. 7. To assess the impact of MvfR function in a more robust manner, FITC-dextran of a higher molecular weight (MW; 20 kDa) was utilized, making it less likely to cross the intestinal barrier. FIG. 8 shows that despite the high MW of FITC, PA14 burn wound infection dramatically increased the intestinal permeability compared to burn alone (mean FITC concentration was 3992 ng/mL for BI with PA14; mean FITC concentration was 213 ng/mL for burn alone; P<0.001). In contrast, mice infected with the mvfR mutant exhibited considerably reduced FITC flux outside the intestinal lumen (685 ng/mL), compared to that promoted by the isogenic parental strain (3992 ng/mL; P<0.001). This finding indicates that MvfR significantly contributed to intestinal barrier dysfunction following *Pseudomonas* burn-site infection.

Example 16. N-Aryl Malonamide (NAM) Agents

Figure 12A:
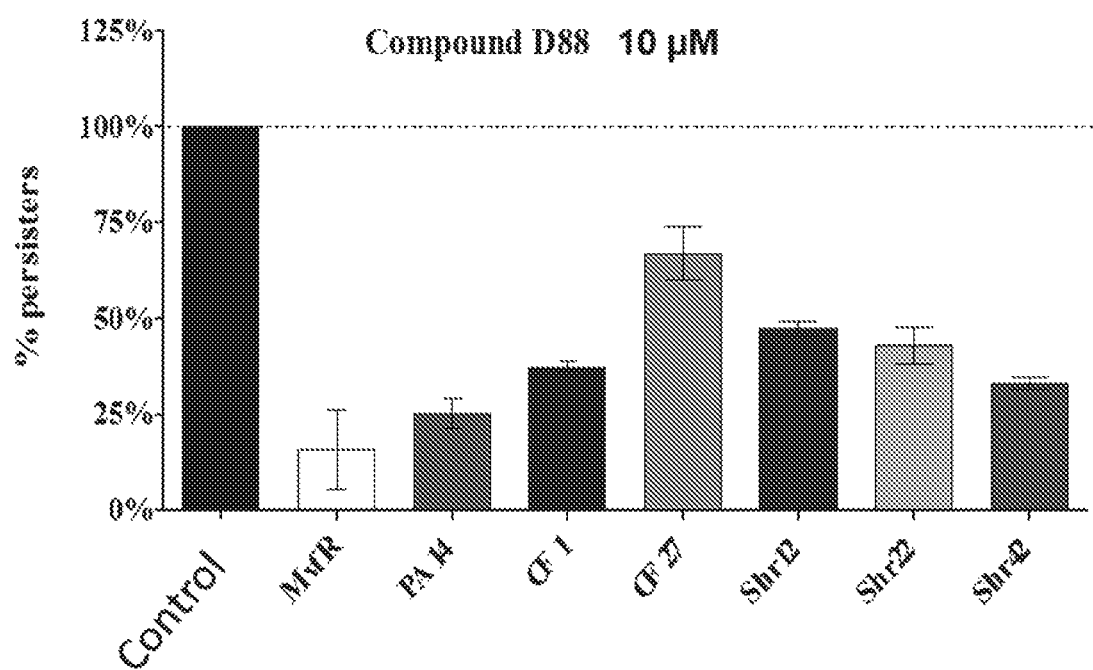
FIGS. 12A-12B show that compound D88 at 10 µM is highly active against antibiotic tolerant/persister cell formation of multiple of *P. aeruginosa* MDR clinical isolates including mucoid strain from CF patients (FIG. 12A) and biofilm formation (FIG. 12B) against PA clinical isolate PA14. Statistical significance to the control was assessed using one-way ANOVA+Dunnett's post-test. P<0.001-0.005.
Figure 12B:
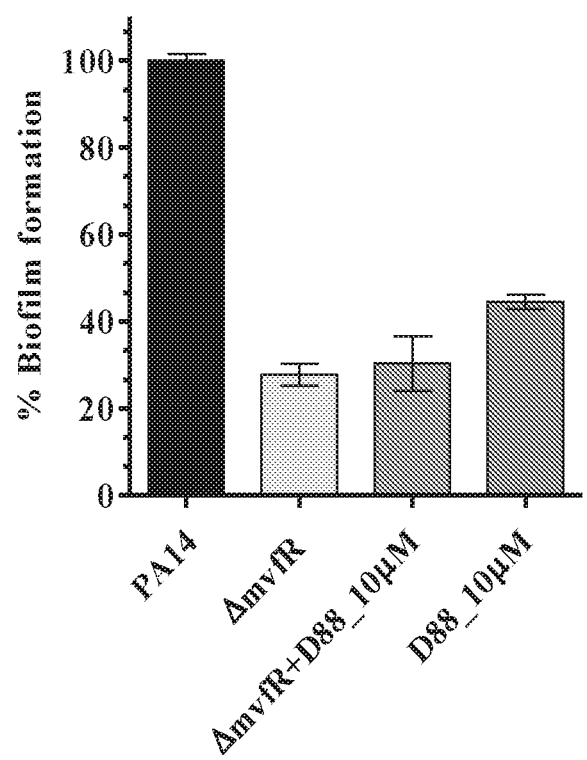

For the SAR and "de-risking" studies, about 100 NAMs were prepared. Table 4 provides a representative list of the NAMs prepared, and which exhibited the most potent $IC_{50}$ (see e.g., FIGS. 12A-12B). Of these NAM agents, compounds D41, D42, D43, D57, D67, D68, D69, D71, D77, D80, D88, D95, and D100 bear no substituents incompatible with in vivo use.

TABLE 4

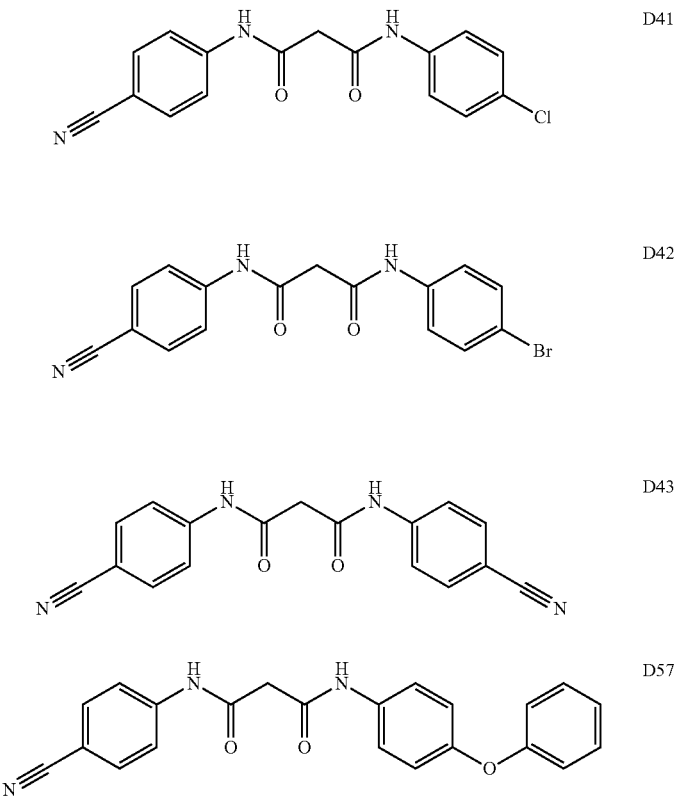

TABLE 4-continued
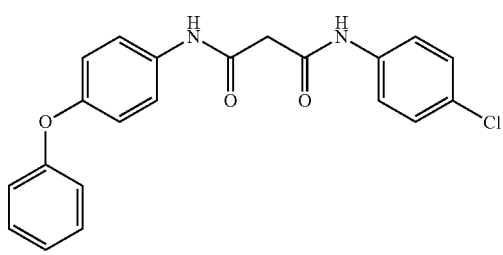 [SMILES: O=C(CC(=O)Nc1ccc(Oc2ccccc2)cc1)Nc1ccc(Cl)cc1]
D67
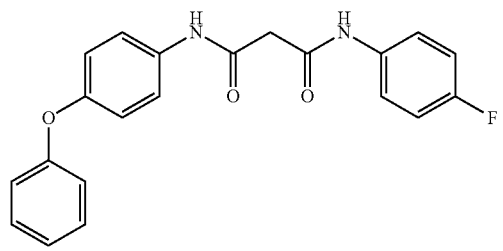 [SMILES: O=C(CC(=O)Nc1ccc(Oc2ccccc2)cc1)Nc1ccc(F)cc1]
D68
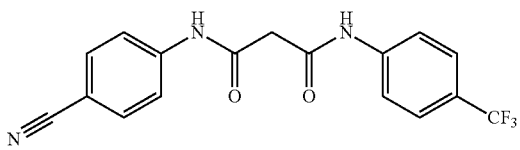 [SMILES: N#Cc1ccc(NC(=O)CC(=O)Nc2ccc(C(F)(F)F)cc2)cc1]
D69
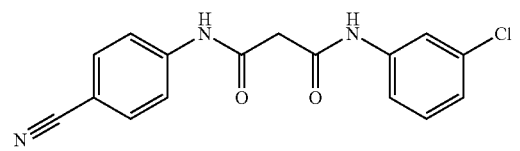 [SMILES: N#Cc1ccc(NC(=O)CC(=O)Nc2cccc(Cl)c2)cc1]
D71
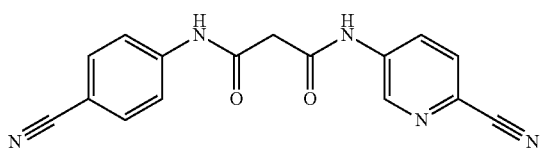 [SMILES: N#Cc1ccc(NC(=O)CC(=O)Nc2ccc(C#N)nc2)cc1]
D77
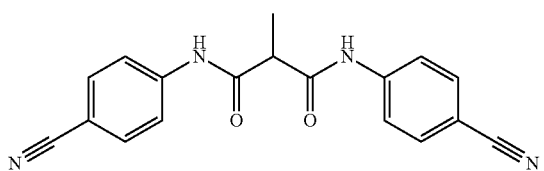 [SMILES: CC(C(=O)Nc1ccc(C#N)cc1)C(=O)Nc1ccc(C#N)cc1]
D80
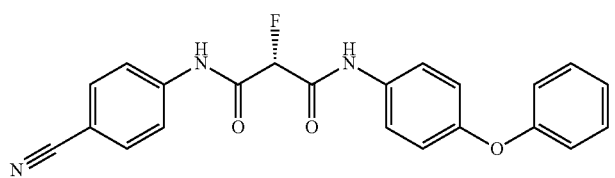
D88
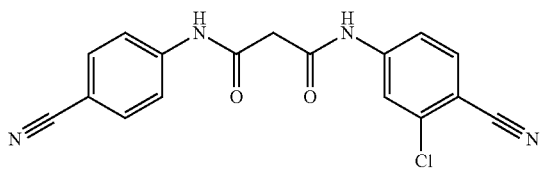 [SMILES: N#Cc1ccc(NC(=O)CC(=O)Nc2ccc(C#N)c(Cl)c2)cc1]
D95

TABLE 4-continued

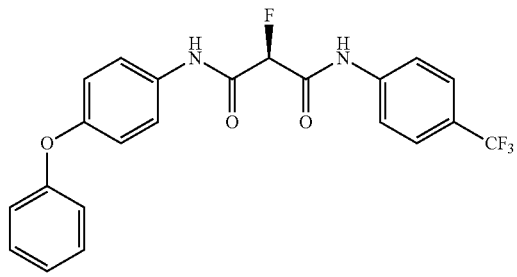 [SMILES: O=C(Nc1ccc(Oc2ccccc2)cc1)[C@@H](F)C(=O)Nc1ccc(C(F)(F)F)cc1]

D100

Figures 9A, 9B:
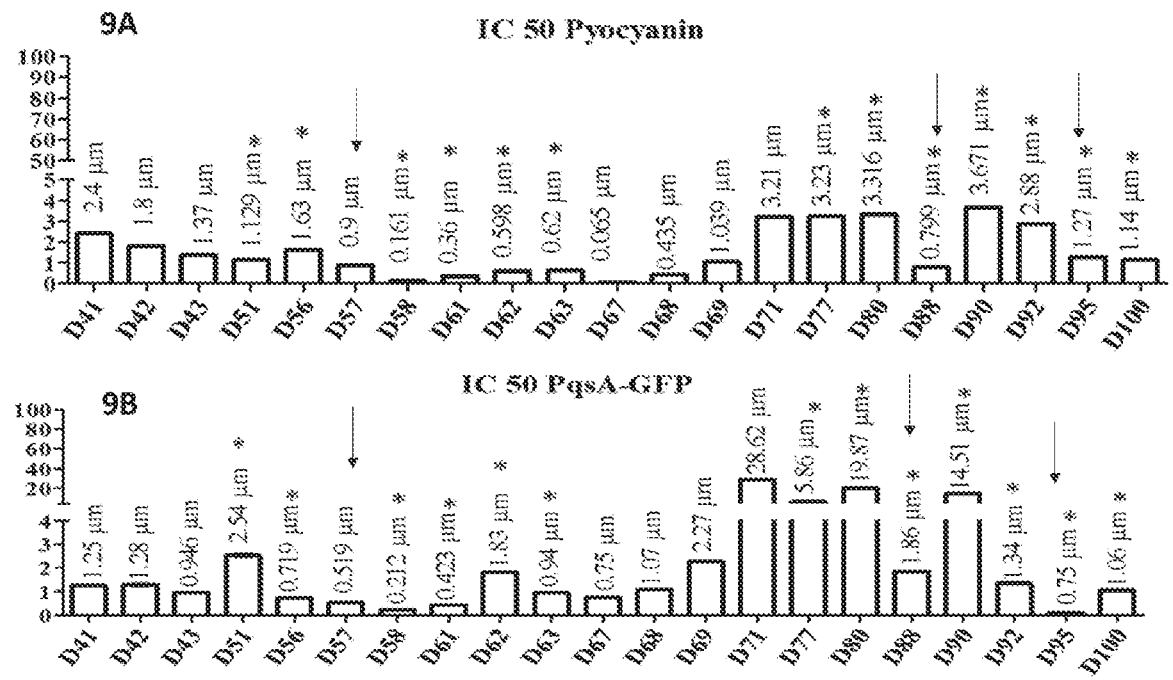
FIGS. 9A-9B show results of $IC_{50}$ assessment showing that NAMs of Example 16 exhibit strong inhibitory activity against MvfR-regulated functions at nanomolar levels.
Figure 9C:
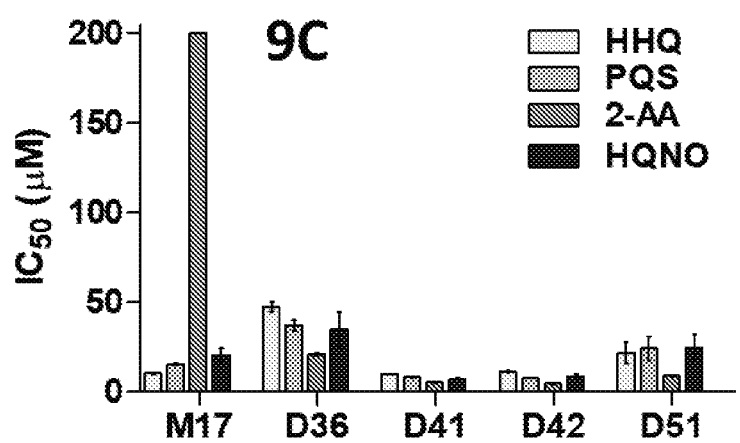
FIG. 9C shows HHQ, PQS, 2-AA, and DHQ levels measured by LC/MS in PA14 wild type strain in the presence or absence of NAMs.
Figure 10:
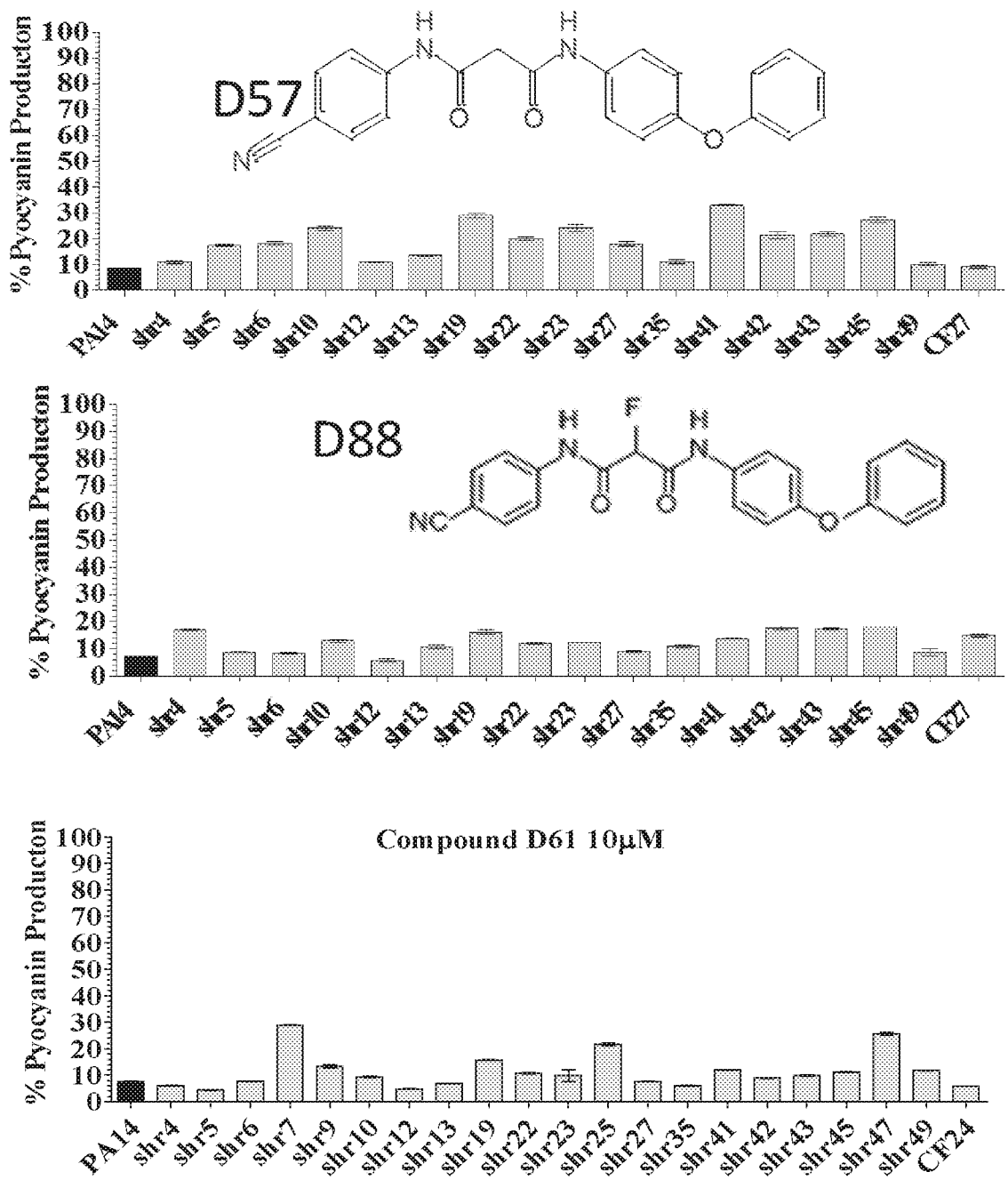
FIG. 10 shows that compounds D57, D61, D62, D63, and D88 at 10 µM are highly active against multiple *Pseudomonas aeruginosa* MDR clinical isolates. Percentage of pyocyanin production is presented in presence of 10 µM of D57 or D88 compounds. Tukey's multiple comparisons test p<0.0001.
Figure 10:
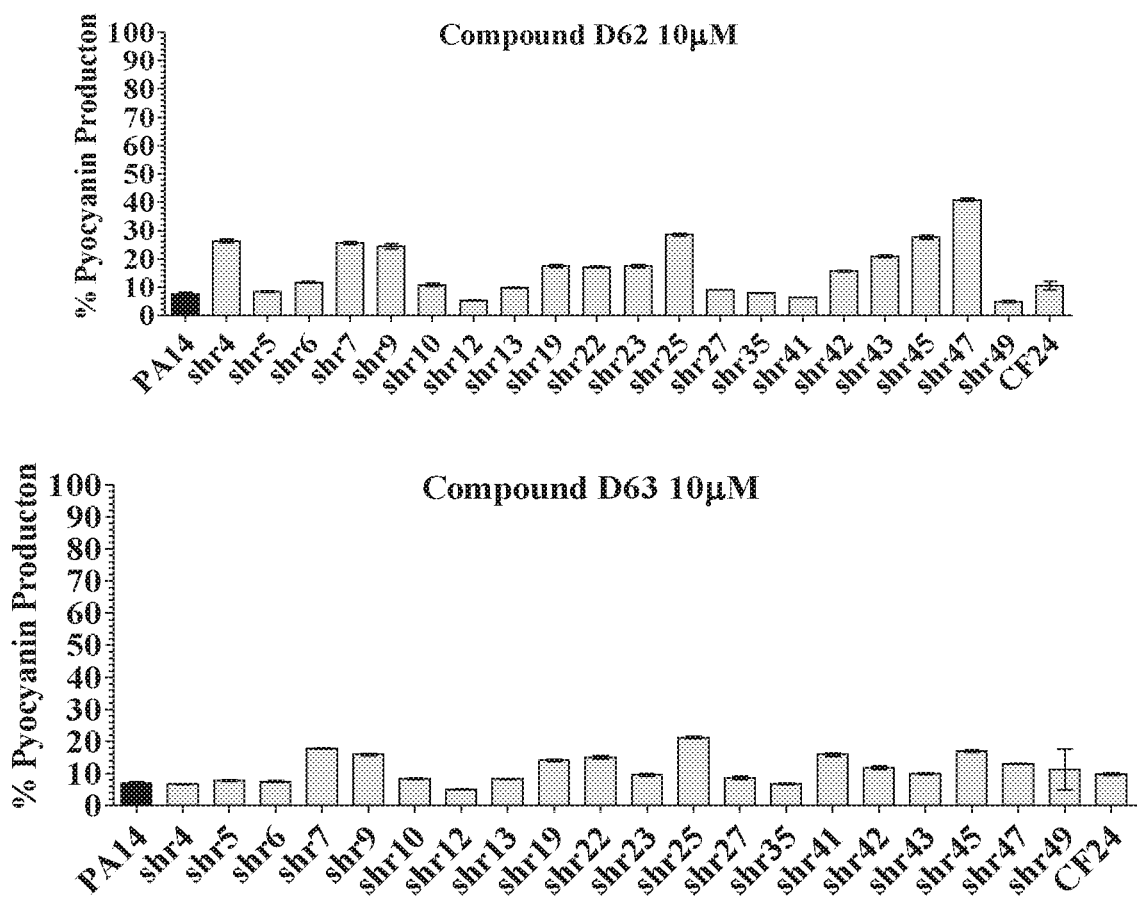
Figures 11A, 11B:
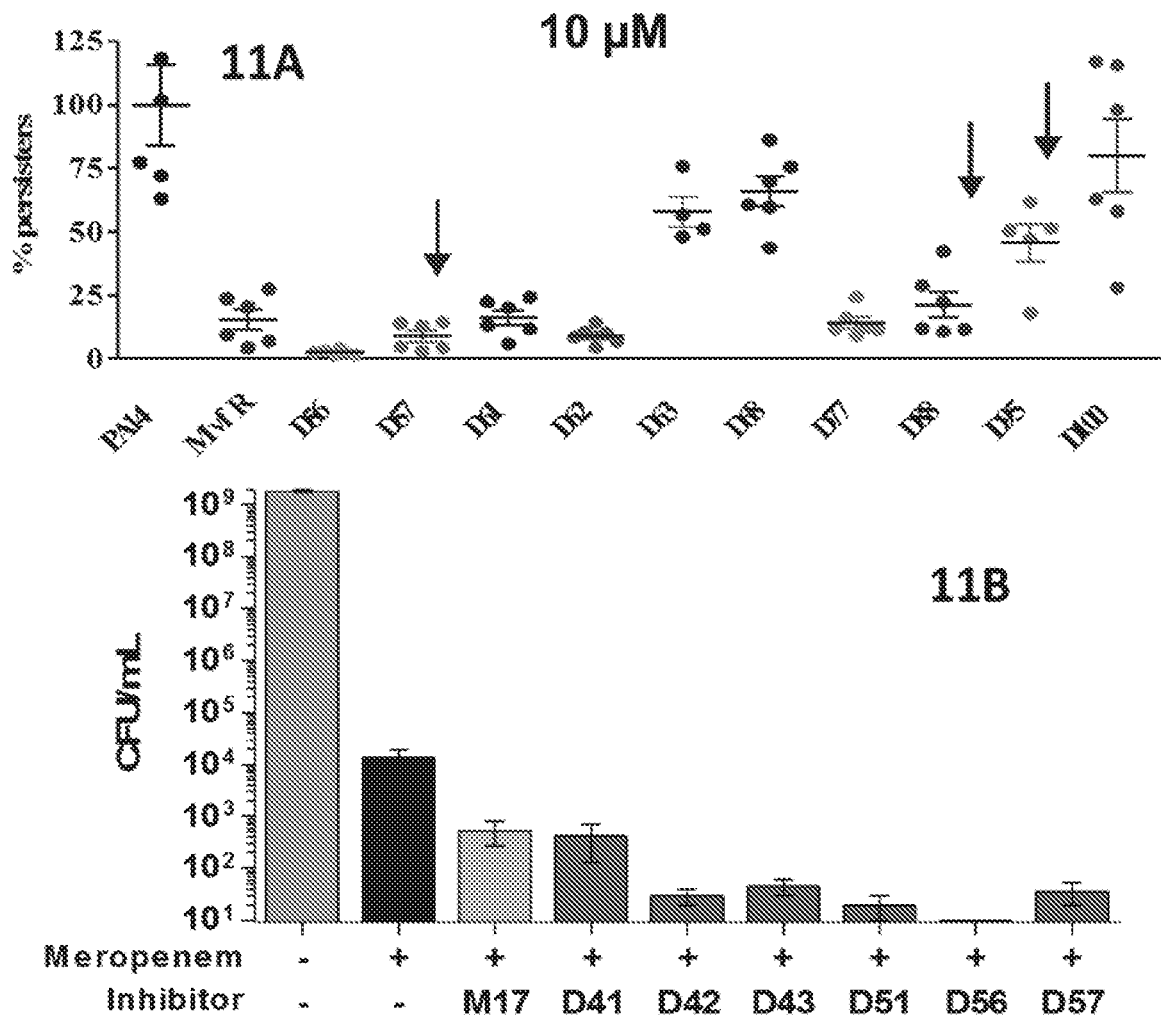
FIG. 11A shows that representative NAM compounds of Example 16, at 10 µM, inhibit the formation of AT/P cells (data presented as % persistence) of the PA clinical isolate PA14.
FIG. 11B shows tolerance to the Meropenem in the presence or absence of inhibitors at 10 µM (data presented in CFU/mL). Results show the average SEM of at least three independent replicates. Statistical significance to the control was assessed using one-way ANOVA+Dunnett's post-test P<0.001-0.005.

Nanomolar levels of most of these MvfR antagonists impeded the activity of MvfR and in consequence the MvfR virulence regulated ACRP functions, including: (1) the production of the important pro-acute P. aeruginosa virulence factor pyocyanin (see e.g., FIG. 9A) the efficacy of two of these potent inhibitors, D57 and D88, was also confirmed by testing many different MDR P. aeruginosa clinical isolates (see e.g., FIG. 11A-11B), providing further confidence of their inhibitory potency; (2) the expression of the genes that encode the enzymes catalyzing the synthesis of both pro-acute and pro-persistence MvfR-regulated virulence molecules, 4-hydroxyl-2-alkyl-quinolines (HAQs) and 2-aminoacetophenon (2-AA), as assessed by pqsAGFP reporter gene expression (see e.g., FIG. 9B) and HAQ production showing the levels of MvfR inducers/ligands HHQ and PQS as well as of the molecules critical for biofilm and Antibiotic tolerant/persiters cells formation HQNO and 2-AA (see e.g., FIG. 9C); (3) AT/P cell formation (see e.g., FIGS. 11A, 12A); (4) biofilm formation (see e.g., FIG. 12B); and (5) biofilm dispersal of preformed biofilm by potentiating antibiotic action (see e.g., FIG. 11B).

The binding affinity to MvfR protein of the most potent MvfR antagonists was also assessed and is shown in Table 4. Plasmon resonance studies with all 12 compounds showed that compounds D41, D42, D57, D88, and D95 exhibited a mean $K_D$ value of 0.25 μM, thus bind and physically interact with high affinity with the MvfR protein. These five compounds were selected to be further de-risked and prioritized based on PK and ADME studies.

Initial solubility studies show that D88 is highly soluble (solubility 490 μM, 0.190 mg/mL; MW 389.0) and initial PK studies show that NAMs D41 and D42 are highly stable in vivo, suggesting that these compounds bear no substituents incompatible with in vivo use.

Additional preliminary results indicate that these compounds, and specifically compound D88, are also potent against other bacterial pathogens, such as Acenitobacter baumanii and adhesive intestinal E. coli.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound selected from any one of the following compounds:

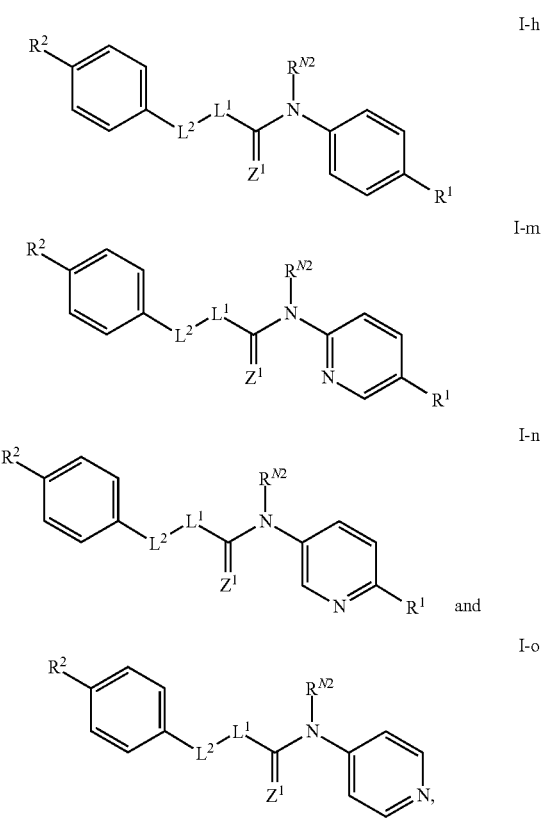

or a pharmaceutically acceptable salt thereof, wherein:

$Z^1$ is selected from the group consisting of O and S;

$L^1$ is selected from the group consisting of methylene, methylmethylene, fluoromethylmethylene, fluoromethylene, difluoromethylene, and aminomethylene;

$L^2$ is selected from the group consisting of $NR^{N1}C(O)$ and $NR^{N1}C(S)$;

$R^{N1}$ and $R^{N2}$ are each independently selected from the group consisting of H and $C_{1-4}$ alkyl;

each $R^1$ is independently selected from the group consisting of $C_{1-4}$ haloalkyl, halo, CN, $NO_2$, $NH_2$, —COOH, —$CONH_2$, and OH; and each $R^2$ is independently selected from the group consisting of halo, CN, $NH_2$, —COOH, —$CONH_2$, —C(O)$C_{1-4}$ haloalkyl, —NHC(O)$C_{1-4}$ haloalkyl, —$NHSO_2$-$C_{1-4}$ alkyl, and phenoxy;

wherein either R¹ is CN or R² is CN or phenoxy; and wherein the compound of Formula I is not:

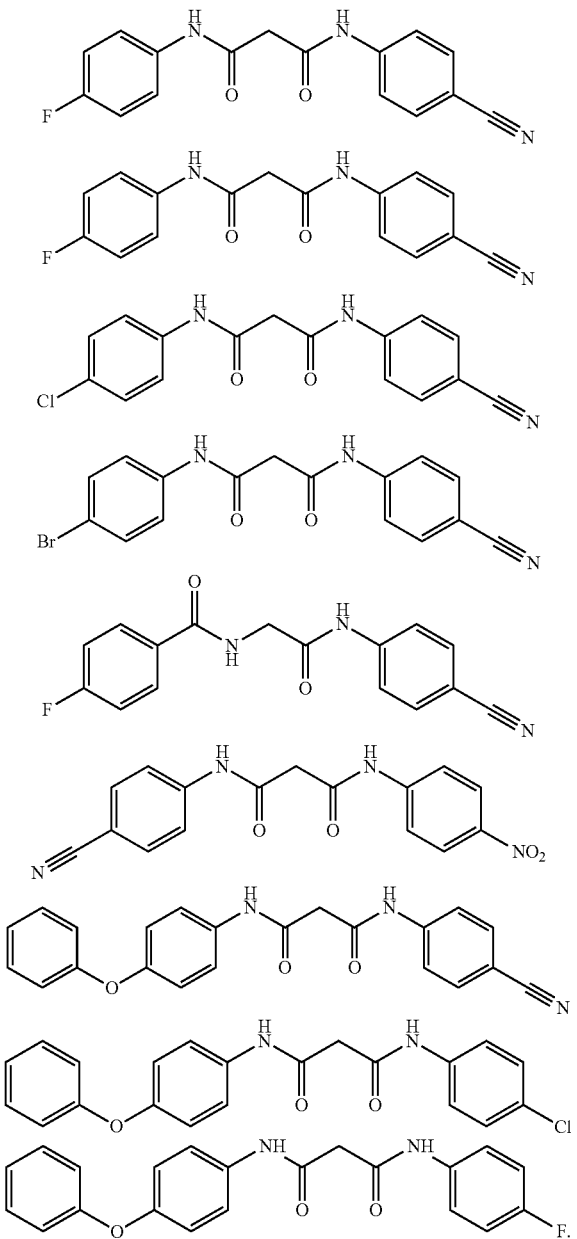

2. The compound of claim 1, or a pharmaceutically acceptable salt thereof, wherein $Z^1$ is O.

3. The compound of claim 1, or a pharmaceutically acceptable salt thereof, wherein $Z^1$ is S.

4. The compound of claim 1, or a pharmaceutically acceptable salt thereof, wherein $L^1$ is methylene.

5. The compound of claim 1, or a pharmaceutically acceptable salt thereof, wherein $L^2$ is $NR^{N1}C(O)$.

6. The compound of claim 1, or a pharmaceutically acceptable salt thereof, wherein each $R^1$ is independently selected from the group consisting of trifluoromethyl, halo, CN, $NO_2$, $NH_2$, and OH.

7. The compound of claim 1, or a pharmaceutically acceptable salt thereof, wherein each $R^2$ is independently selected from the group consisting of fluoro, iodo, CN, $NH_2$, $-C(O)CF_3$, $-NHC(O)CF_3$, $-NHSO_2CH_2CH_3$, and phenoxy.

8. The compound of claim 1, or a pharmaceutically acceptable salt thereof, wherein:
   $Z^1$ is selected from the group consisting of O and S;
   $L^1$ is selected from the group consisting of methylene, methylmethylene, fluoromethylmethylene, and fluoromethylene;
   $L^2$ is selected from the group consisting of $NR^{N1}C(O)$ and $NR^{N1}C(S)$;
   $R^{N1}$ is selected from the group consisting of H and methyl;
   $R^{N2}$ is selected from the group consisting of H and methyl;
   each $R^1$ is independently selected from the group consisting of trifluoromethyl, halo, CN, $NO_2$, $NH_2$, and OH; and
   each $R^2$ is independently selected from the group consisting of fluoro, iodo, CN, $NH_2$, $-C(O)CF_3$, $-NHC(O)CF_3$, $-NHSO_2CH_2CH_3$, and phenoxy.

9. The compound of claim 1, or a pharmaceutically acceptable salt thereof, wherein:
   $Z^1$ is O;
   $L^1$ is selected from the group consisting of methylene, methylmethylene, fluoromethylmethylene, and fluoromethylene;
   $L^2$ is $NR^{N1}C(O)$;
   $R^{N1}$ is selected from the group consisting of H and methyl;
   $R^{N2}$ is selected from the group consisting of H and methyl;
   each $R^1$ is independently selected from the group consisting of trifluoromethyl, halo, CN, $NO_2$, $NH_2$, and OH; and
   each $R^2$ is independently selected from the group consisting of fluoro, iodo, CN, $NH_2$, $-C(O)CF_3$, $-NHC(O)CF_3$, $-NHSO_2CH_2CH_3$, and phenoxy.

10. The compound of claim 1, or a pharmaceutically acceptable salt thereof, wherein the compound is selected from the group consisting of:

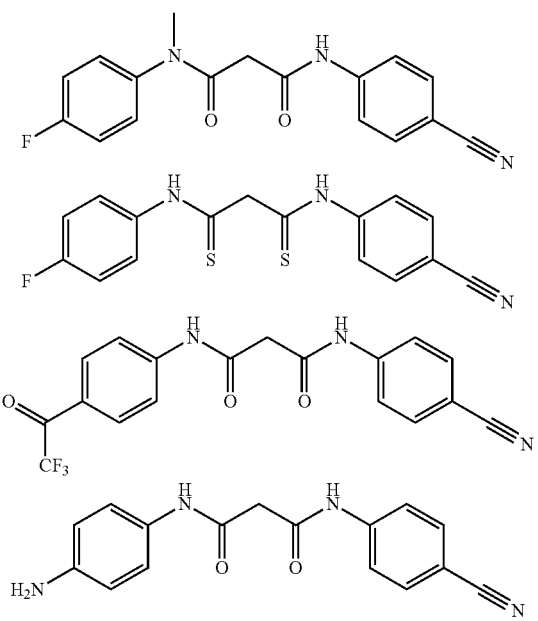

-continued
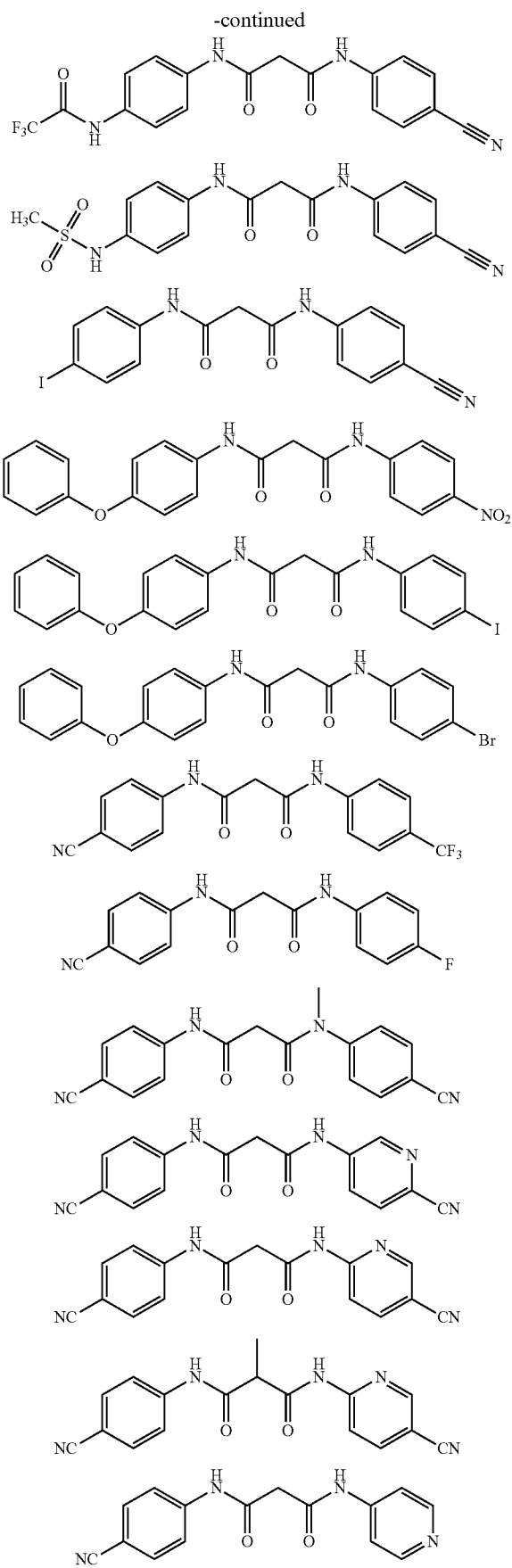
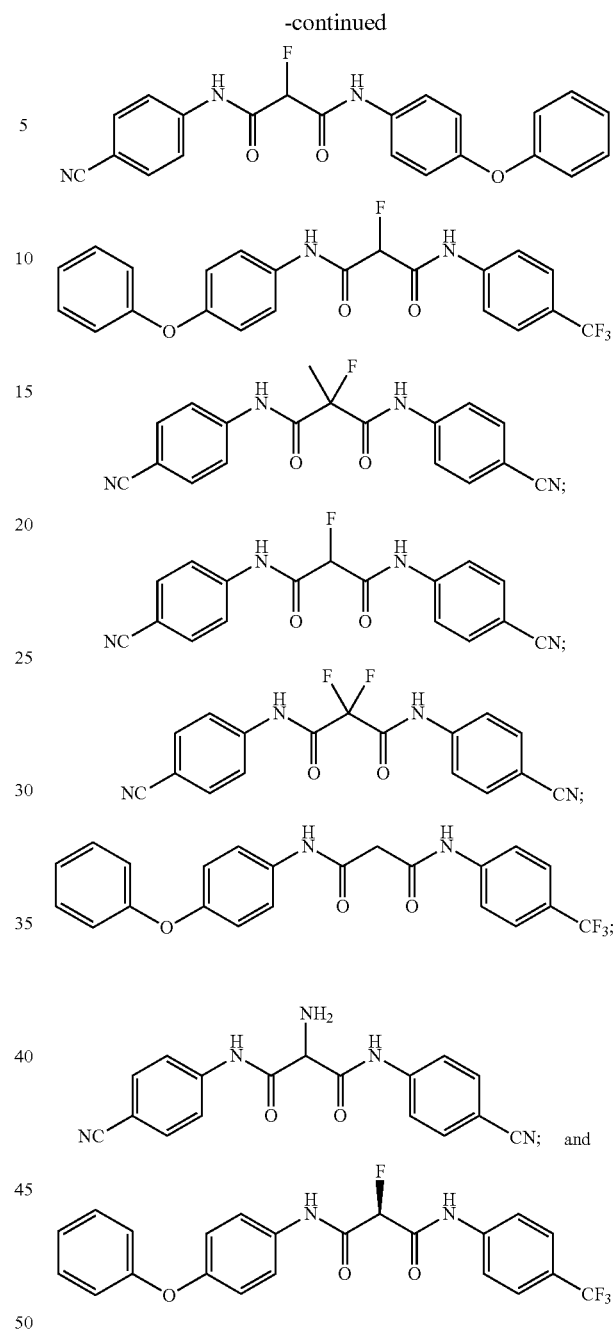
or a pharmaceutically acceptable salt thereof.
11. A pharmaceutical composition, comprising a compound of claim 1, or a pharmaceutically acceptable salt thereof, and a pharmaceutically acceptable carrier.
12. A compound of formula:
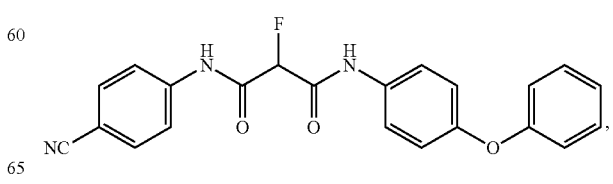
or a pharmaceutically acceptable salt thereof.

13. A compound selected from:
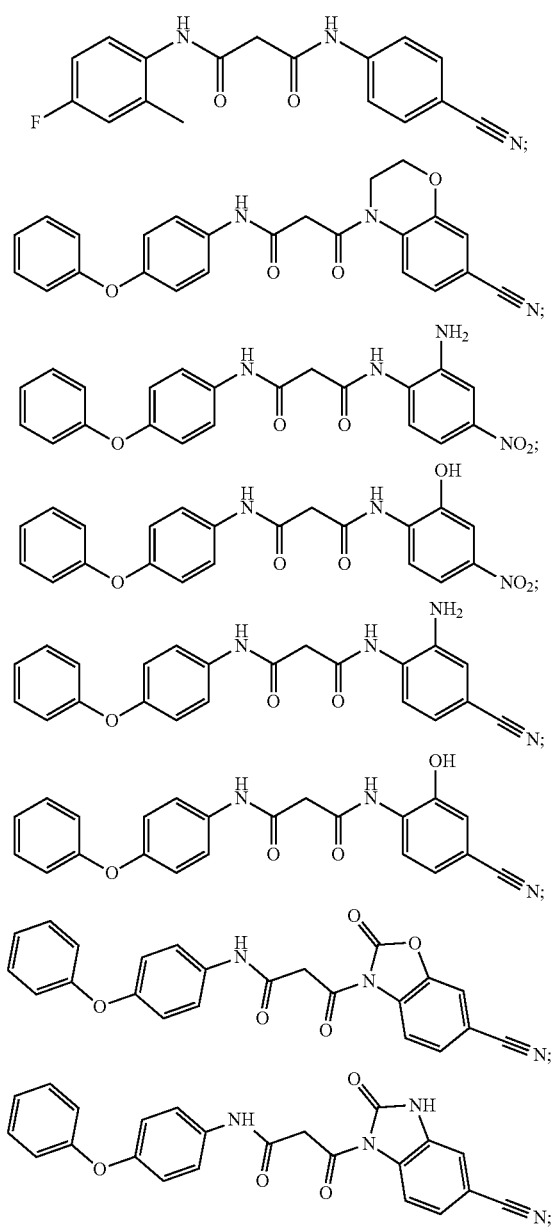
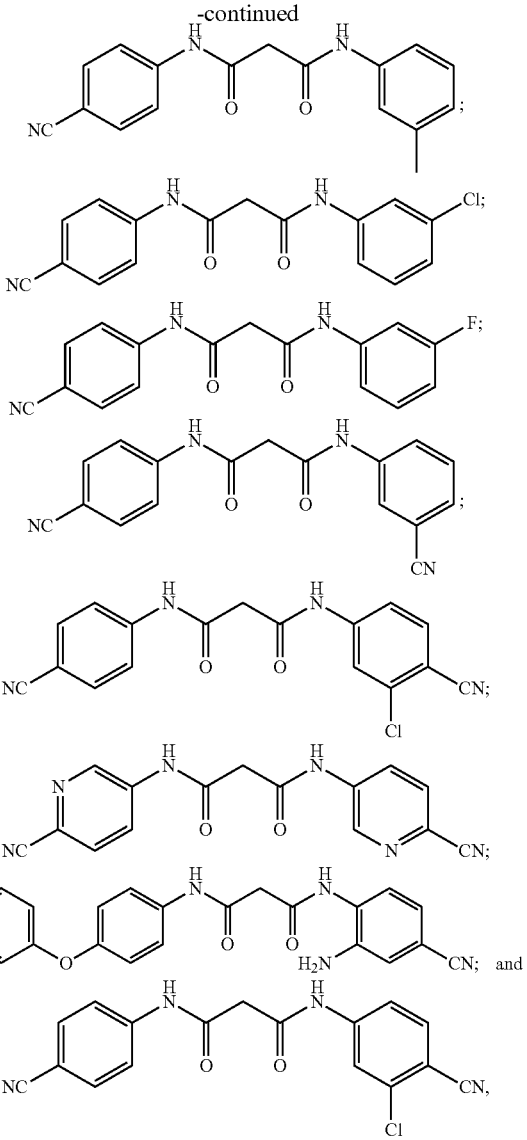
or a pharmaceutically acceptable salt thereof.
14. A pharmaceutical composition, comprising a compound of claim 13, or a pharmaceutically acceptable salt thereof, and a pharmaceutically acceptable carrier.
* * * * *

UNITED STATES PATENT AND TRADEMARK OFFICE
CERTIFICATE OF CORRECTION

PATENT NO. : 11,731,946 B2
APPLICATION NO. : 16/757096
DATED : August 22, 2023
INVENTOR(S) : Laurence Rahme et al.

Page 1 of 1

It is certified that error appears in the above-identified patent and that said Letters Patent is hereby corrected as shown below:

In the Specification

In Column 1, Line 9, delete "No." and insert -- Nos. --

In the Claims

In Column 131, Lines 5-9 (approx.), Claim 1, delete

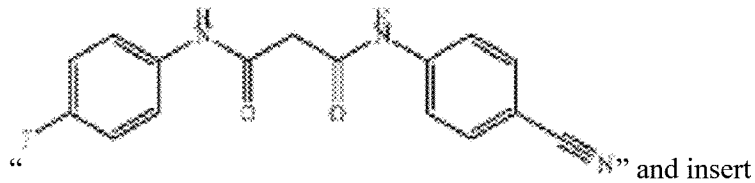 " and insert

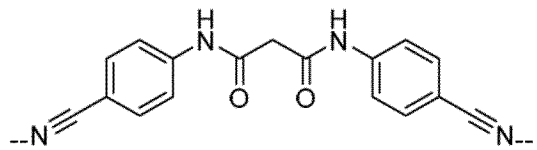

In Column 133, Lines 57-62 (approx.), Claim 10, delete

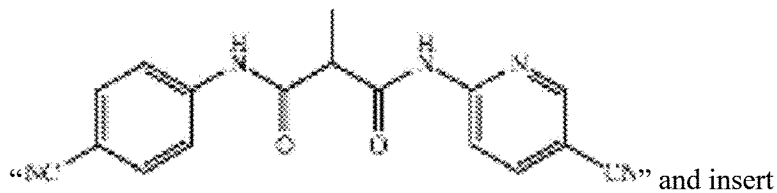 " and insert

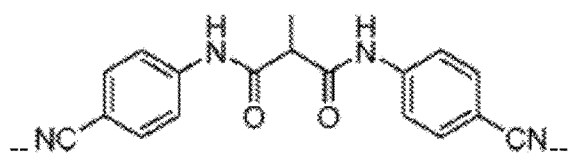

Signed and Sealed this
Twentieth Day of January, 2026

John A. Squires
*Director of the United States Patent and Trademark Office*